(12) United States Patent
Roeder et al.

(10) Patent No.: US 6,248,520 B1
(45) Date of Patent: Jun. 19, 2001

(54) NUCLEIC ACID MOLECULES ENCODING NUCLEAR HORMONE RECEPTOR COACTIVATORS AND USES THEREOF

(75) Inventors: Robert G. Roeder, New York, NY (US); Joseph D. Fondell, Baltimore, MD (US); Chao Xingyuan; Mitsuhiro Ito, both of New York, NY (US)

(73) Assignee: The Rockefeller University, New York, NY (US)

( * ) Notice: Subject to any disclaimer, the term of this patent is extended or adjusted under 35 U.S.C. 154(b) by 0 days.

(21) Appl. No.: 09/110,517

(22) Filed: Jul. 6, 1998

(Under 37 CFR 1.47)

(51) Int. Cl.$^7$ ...................................................... C12Q 1/68
(52) U.S. Cl. ............................ 435/6; 435/91.1; 435/91.2; 435/91.21; 435/91.51; 514/44
(58) Field of Search ................................. 514/44; 435/6, 435/91.1, 91.2, 91.21, 91.51

(56) References Cited

FOREIGN PATENT DOCUMENTS

| WO94/10338 | 5/1994 | (WO) . |
| WO99/31231 | 6/1999 | (WO) . |

OTHER PUBLICATIONS

Yuan et al. Proc. Nat'l Acad. Sci., vol. 95 (14) pp. 7939–7944, Jul. 7, 1998.*
Rachez et al., 1998, Genes & Dev. 12:1787–1800.
Brun et al., (1997) J. Endocrinol. 155, 217–218.
Burley et al.,. (1996) Annu. Rev. Biochem. 65, 769–799.
Chang et al.,(1997) Proc. Natl. Acad. Sci. USA 94, 9040–9045.
Chen et al.,. (1997) Cell 90, 569–580.
Glass et al., (1997) Curr. Opin. Cell Biol. 9, 222–232.
Goldman et al., (1997) Recent Prog. Horm. Res. 52, 103–119.
Gu et al., (1997) Cell 90, 595–606.
Heinzel et al., 1997) Nature 387, 43–48.
Kaiser et al., (1996) Trends Biochem. Sci. 21, 342–345.
Katz et al., (1994) J. Biol. Chem. 269, 18915–18920.
Kwok et al., (1994) Nature 370, 223–226.
Lee et al.,(1995) Mol. Endocrinol. 9, 243–254.
Lemon et al.,(1997) Mol. Cell. Biol. 17, 1923–1937.
Luo et al.,(1992) Cell 71, 231–241.
Mangelsdorf et al., (1995) Cell 83, 841–850.
Meyer et al., (1989) Cell 57, 433–442.
Monden et al.,(1997) J. Biol. Chem. 272, 29834–29841.
Myers et al.,. (1998) Genes Dev. 12, 45–54.
Nagase et al., (1995) DNA Res. 2, 167–174.
Nagy et al.,(1997) Cell 89, 373–380.
Ogryzko et al.,(1996) Cell 87, 953–959.
Ozono et al.,. (1990) J. Biol. Chem. 265, 21881–21888.
Rees et al., (1996) BioTechniques 20, 102–110.
Roeder,. (1996) Trends Biochem. Sci. 21, 327–335.
Shibata et al., (1997) Recent Prog. Horm. Res. 52, 141–164.
Spencer et al., 1997) Nature 389, 194–198.
Voegel et al.,(1998) EMBO J. 17, 507–519.
Wu,. (1997) J. Biol. Chem. 272, 28171–28174.
Yuan et al.,(1997) Cell Stress & Chaperones 2, 263–275.
International Search Report for Application PCT/US99/15052.
Drane et al., 1997, Oncogene 15:3013–24.
EMBL Database hum3 Sequence ID Hsdkg10 Human mRNA for KIAA0130 gene, complete CDS.
Zhu et al., 1997, J. Biol. Chem. 272, 25500–25506.
Fondell et al., 1996, PNAS USA 93:8329–8333.
Yuan et al., 1998, PNAS USA 95:7030–7044.

* cited by examiner

Primary Examiner—W. Gary Jones
Assistant Examiner—Janell E. Taylor
(74) Attorney, Agent, or Firm—Klauber & Jackson

(57) ABSTRACT

Isolated nucleic acid molecules encoding Thyroid Receptor-Associated Proteins (TRAPS) are provided. TRAPS are members of protein complexes that bind to nuclear hormone receptors in a ligand-dependent manner so that the receptor, upon activation by a corresponding hormone, regulates the transcription of a particular gene. Also provided are methods of replicating and expressing such isolated nucleic acid molecules, pharmaceutical compositions comprising TRAPS, and methods of modulating gene expression via administration of therapeutically effective amounts of such pharmaceutical compositions.

56 Claims, 17 Drawing Sheets

FIG. 1A

```
  1  cggacaggcg cacacgacgc ctcgagcacc cttctcttct tgccgccggg gacttcagat
 61  tgatccttcc cgggaagagt aggactgct ggtgccctgc gtcccggat cccagccaa
121  cttgtttcct ccgttagtgg tggggaaggg cttatccttt tgtggcggat ctagcttctc
181  ctcgccttca ggatgaaagc tcaggggggaa accgaggagt cagaaaagct gagtaagatg
241  agttctctcc tggaacggct ccatgcaaaa tttaaccaaa atagaccctg gagtgaaacc
301  attaagcttg tgcgtcaagt catggagaag agggttgtga tgagttctgg agggcatcaa
361  catttggtca gctgtttgga gacattgcag aagctctca aagtaacatc tttaccagca
421  atgactgatc gtttggagtc catagcaaga cagaatggac tgggctctca tctcagtgcc
481  agtggcactg aatgttacat cacgtcagat atgttctatg tggaagtgca gttagatcct
541  gcaggacagc tttgtgatgt aaaagtggct caccatgggg agaatcctgt gagctgtccg
601  gagcttgtac agcagctaag ggaaaaaaat tttgatgaat tttctaagca ccttaaggc
661  cttgttaatc tgtataacct tccaggggac aacaaactga agactaaaat gtacttgct
721  ctccaatcct tagaacaaga tctttctaaa atggcaatta tgtactgaa agcaactaat
781  gctggtccct tggataagat tcttcatgga agtgttggct atctcacacc aaggagtggg
841  ggtcatttaa tgaacctgaa gtactatgtc tctccttctg acctactgga tgacaagact
```

FIG. 1B

```
 901  gcatctccca tcatttgca tgagaataat gtttctcgat ctttgggcat gaatgcatca
 961  gtgacaattg aaggaacatc tgctgtgtac aaactcccaa ttgcaccatt aattatgggg
1021  tcacatccag ttgacaataa atggacccct tccttctcct caatcaccag tgccaacagt
1081  gttgatcttc ctgcctgttt cttcttgaaa tttccccagc caatcccagt atctagagca
1141  tttgttcaga aactgcagaa ctgcacagga attccattgt ttgaaactca accaacttat
1201  gcaccccctgt atgaactgat cactcagttt gagctatcaa aggaccctga ccccatacct
1261  ttgaatcaca acatgagatt ttatgctgct cttcctggtc agcagcactg ctatttcctc
1321  aacaaggatg ctcctctttcc agatggccga agtctacagg gaacccttgt tagcaaaatc
1381  acctttcagc accctggccg agttcctctt atcctaaatc tgatcagaca ccaagtggcc
1441  tataacaccc tcattggaag ctgtgtcaaa agaactattc tgaaagaaga ttctcctggg
1501  cttctccaat ttgaagtgtg tcctctctca gagtctcgtt tcagcgtatc ttttcagcac
1561  cctgtgaatg actccctggt gtgtgggta atggatgtgc aggactcaac acatgtgagc
1621  tgtaaactct acaaagggct gtcggatgca ctgatctgca cagatgactt cattgccaaa
1681  gttgttcaaa gatgtatgtc catccctgtg acgatgaggg ctattcggag gaaagctgaa
```

FIG. 1C

```
1741 accattcaag ccgacacccc agcactgtcc ctcattgcag agacagttga agacatggtg
1801 aaaaagaacc tgccccgct agcaggccca gggtatggca tgaccacagg caacaaccca
1861 atgagtggta ccactacacc aaccaacacc tttccggggg gtcccattac caccttgttt
1921 aatatgagca tgagcatcaa agatcggcat gagtcggtgg gccatgggga ggacttcagc
1981 aaggtgtctc agaacccaat tcttaccagt ttgttgcaaa tcacagggaa cggggggtct
2041 accattggct cgagtccgac ccctcctcat cacacgccgc cacctgtctc ttcgatggcc
2101 ggcaacacca agaaccaccc gatgctcatg aaccttctta aagataatcc tgcccaggat
2161 ttctcaaccc tttatgaag cagccctta gaaaggcaga actcctcttc cggctcaccc
2221 cgcatggaaa tatgctcggg gagcaacaag accaagaaaa agaagtcatc aagattacca
2281 cctgagaaac caaagcacca gactgaagat gactttcaga gggagctatt ttcaatggat
2341 gttgactcac agaagcctat ctttgatgtc aacatgacag ctgacacact ggatacgcca
2401 cacatcactc cagctccaag ccagtgtagc actcccccaa caacttaccc acaaccagta
2461 cctcaccccc aaccagtat tcaaaggatg gtccgactat ccagttcaga cttctaaact tcccagcact
2521 ccagatgtaa ctgacatcct ttcagacatt gcagaagaag cttctaaact tcccagcact
2581 agtgatgatt gcccagccat tggcacccct cttcgagatt cttcaagctc tgggcattct
```

FIG. 1D

```
2641  cagagtaccc tgtttgactc tgatgtcttt caaactaaca ataatgaaaa tccatacact
2701  gatccagctg atcttattgc agatgctgct ggaagcccca gtagtgactc tcctaccaat
2761  catttttttc atgatggagt agatttcaat cctgatttat tgaacagcca gagccaaagt
2821  ggttttggag aagaatattt tgatgaaagc agccaaagtg gggataatga tgatttcaaa
2881  ggatttgcat ctcaggcact aaatactttg ggggtgccaa tgcttggagg tgataatggg
2941  gagaccaagt ttaagggcaa taaccaagcc gacacagttg atttcagtat tatttcagta
3001  gccggcaaag ctttagctcc tgcagatctt atggagcatc acagtggtag tcaggtcct
3061  ttactgacca ctgggggactt agggaaagaa aagactcaaa agagggtaaa ggaaggcaat
3121  ggcaccagta atagtactct ctcggggccc ggattagaca gcaaaccagg gaagcgcagt
3181  cggacccctt ctaatgatgg gaaaagcaaa gataagcctc caaagcggaa gaaggcagac
3241  actgagggaa agtctccatc tcatagttct tctaacagac cttttacccc acctaccagt
3301  acaggtggat ctaaatcgcc aggcagtgca ggaagatctc agactccccc agtgttgcc
3361  acaccaccca ttcccaaaat cactattcag attcctaagg gaacagtgat ggtgggcaag
3421  ccttcctctc acagtcagta taccagcagt ggttctgtgt cttcctcagg cagcaaaagc
```

FIG. 1E

```
3481  caccatagcc attcttcctc ctcttcctca tctgttcca cctcagggaa gatgaaagc
3541  agtaaatcag aaggttcatc aagttccaag ttaagtagca gtatgtattc tagccagggg
3601  tcttctggat ctagccagtc caaaaattca tcccagtctg gggggaagcc aggctcctct
3661  cccataacca agcatggact gagcagtggc tctagcagca ccaagatgaa acctcaagga
3721  aagccatcat cacttatgaa tccttcttta agtaaaccaa acatatcccc ttctcattca
3781  aggccacctg gaggctctga caagcttgcc tctccaatga agcctgttcc tggaactcct
3841  ccatcctcta aagccaagtc ccctatcagt tcaggttctg gtggttctca tatgtctgga
3901  actagttcaa gctctggcat gaagtcatct tcagggttag gatcctcagg ctcgttgtcc
3961  cagaaaactc cccatcatc taattcctgt acggcatctt cctcctcctt ttcctcaagt
4021  ggctcttcca tgtcatcctc tcagaaccag catgggagtt ctaaaggaaa atctcccagc
4081  agaaacaaga agccgtcctt gacagctgtc atagataaac tgaagcatgg ggttgtcacc
4141  agtggccctg ggggtgaaga cccactggac ggccagatgg gggtgagcac aaattcttcc
4201  agccatccta tgtcctccaa acataacatg tcaggaggag agtttcaggg caagcgtgag
4261  aaaagtgata aagacaaatc aaaggtttcc acctccggga gttcagtgga ttcttctaag
4321  aagacctcag agtcaaaaaa tgtggggagc acaagtgtgg caaaaattat catcagtaag
```

FIG. 1F

```
4381 catgatggag gctcccctag cattaaagcc aaagtgactt tgcagaaacc tggggaaagt
4441 agtggagaag ggcttaggcc tcaaatggct tcttctaaaa actatggctc tccactcatc
4501 agtggttcca ctccaaagca tgagcgtggc tctcccagcc atagtaagtc accagcatat
4561 accccccaga atctggacag tgaaagtgag tcaggctcct ccatagcaga gaaatcttat
4621 cagaatagtc ccagctcaga cgatggtatc cgaccacttc cagaatacag cacagagaaa
4681 cataagaagc acaaaaagga aagaagaaa gtaaaagaca aagataggga ccgagaccgg
4741 gacaaagacc gagacaagaa aaaatctcat agcatcaagc cagagagttg gtccaaatca
4801 cccatctctt cagaccagtc cttgtctatg acaagtaaca caatcttatc tgcagacaga
4861 ccctcaaggc tcagcccaga ctttatgatt ggggaggaag atgatgatct tatggatgtg
4921 gccctgattg ggaattagga accttatttc ctaaaagaaa caggcccaga ggaaaaaaaa
4981 ctattgataa gtttataggc aaaccacc
```

FIG. 2

```
/codon_start=1
/product="TRAP220"
/translation="MKAQGETEESEKLSKMSSLLERLHAKFNQNRPWSETIKLVRQVM
EKRVVMSSGGHQHLVSCLETLQKALKVTSLPAMTDRLESIARQNGLGSHLSASGTECY
ITSDMFYVEVQLDPAGQLCDVKVAHHGENPVSCPELVQQLREKNFDEFSKHLKGLVNL
YNLPGDNKLKTKMYLALQSLEQDLSKMAIMYWKATNAGPLDKILHGSVGYLTPRSGGH
LMNLKYYVSPSDLLDDKTASPIILHENNVSRSLGMNASVTIEGTSAVYKLPIAPLIMG
SHPVDNKWTPSFSSITSANSVDLPACFFLKFPQPIPVSRAFVQKLQNCTGIPLFETQP
TYAPLYELITQFELSKDPDPIPLNHNMRFYAALPGQQHCYFLNKDAPLPDGRSLQGTL
VSKITFQHPGRVPLILNLIRHQVAYNTLIGSCVKRTILKEDSPGLLQFEVCPLSESRF
SVSFQHPVNDSLVCVVMDVQDSTHVSCKLYKGLSDALICTDDFIAKVVQRCMSIPVTM
RAIRRKAETIQADTPALSLIAETVEDMVKKNLPPLAGPGYGMTTGNNPMSGTTTPTNT
FPGGPITTLFNMSMSIKDRHESVGHGEDFSKVSQNPILTSLLQITGNGGSTIGSSPTP
PHHTPPPVSSMAGNTKNHPMLMNLLKDNPAQDFSTLYGSSPLERQNSSSGSPRMEICS
GSNKTKKKKSSRLPPEKPKHQTEDDFQRELFSMDVDSQKPIFDVNMTADTLDTPHITP
APSQCSTPPTTYPQPVPHPQPSIQRMVRLSSSDSIGPDVTDILSDIAEEASKLPSTSD
DCPAIGTPLRDSSSSGHSQSTLFDSDVFQTNNNENPYTDPADLIADAAGSPSSDSPTN
HFFHDGVDFNPDLLNSQSQSGFGEEYFDESSQSGDNDDFKGFASQALNTLGVPMLGGD
NGETKFKGNNQADTVDFSIISVAGKALAPADLMEHHSGSQGPLLTTGDLGKEKTQKRV
KEGNGTSNSTLSGPGLDSKPGKRSRTPSNDGKSKDKPPKRKKADTEGKSPSHSSSNRP
FTPPTSTGGSKSPGSAGRSQTPPGVATPPIPKITIQIPKGTVMVGKPSSHSQYTSSGS
VSSSGSKSHHSHSSSSSSASTSGKMKSSKSEGSSSSKLSSSMYSSQGSSGSSQSKNS
SQSGGKPGSSPITKHGLSSGSSSTKMKPQGKPSSLMNPSLSKPNISPSHSRPPGGSDK
LASPMKPVPGTPPSSKAKSPISSGSGGSHMSGTSSSSGMKSSSGLGSSGSLSQKTPPS
SNSCTASSSFSSSGSSMSSSQNQHGSSKGKSPSRNKKPSLTAVIDKLKHGVVTSGPG
GEDPLDGQMGVSTNSSHPMSSKHNMSGGEFQGKREKSDKDKSKVSTSGSSVDSSKKT
SESKNVGSTSVAKIIISKHDGGSPSIKAKVTLQKPGESSGEGLRPQMASSKNYGSPLI
SGSTPKHERGSPSHSKSPAYTPQNLDSESESGSSIAEKSYQNSPSSDDGIRPLPEYST
EKHKKHKKEKKKVKDKDRDRDRDKDRDKKKSHSIKPESWSKSPISSDQSLSMTSNTIL
SADRPSRLSPDFMIGEEDDDLMDVALIGN"
```

FIG. 3A

```
   1 atgaaggtgg tcaacctgaa gcaagccatt ttgcaagcct ggaaggagcg ctggagtgac
  61 taccaatggg caatcaacat gaagaaattc tttcctaaag agccacctg ggatattctc
 121 aacctggcag atgcgttact agagcaggcc atgattggac catccccaa tcctctcatc
 181 ttgtcctacc tgaagtatgc cattagttcc cagatggtgt cctactcttc tgtcctcaca
 241 gccatcagta agtttgatga cttttctcgg gacctgtgtg tccaggcatt gctggacatc
 301 atggacatgt tttgtgaccg tctgagctgt cacggcaaag cagaagaatg catcggactg
 361 tgccgagccc ttcttagcgc cctccactgg ctgctgcgct gcacggcagc ctctgcagaa
 421 cggctgcggg aagggctgga agccggcact ccagccgctg gggagaagca gcttgccatg
 481 tgccttcagc gcctggagaa aaccctcagc agcaccaaga accgggccct gctgcacatc
 541 gccaaactag aggaggcctc ttcttggact gccatcgagc attctctctt gaaacttgga
 601 gagatcctgg ccaatctcag caacccgcag ctccggagtc aggccgagca gtgtgcacc
 661 ctcattagga gcatccccac gatgctgtct gtgcatgcgg agcagatgca caagaccggc
 721 ttcccccactg tccacgccgt gatcctgctc gagggcacca tgaacctgac aggcgagacg
 781 cagtccctgg tggagcagct gacgatggtg aagcgcatgc agcatatccc caccccactt
 841 tttgtcctgg agatctgaa agcttgcttc gtggggctca ttgagtctcc cgagggtacg
 901 gaggagctca agtggacagc tttcactttc tcaagattc cacaggtttt ggtgaagttg
 961 aagaagtact ctcatggaga caaggacttc actgaggatg tcaactgtgc tttgagttc
1021 ctgctgaagc tcaccccctt gttggacaaa gctgaccagc gctgcaactg tgactgtaca
1081 aacttcctgc tccaagaatg tggcaagcag gggcttctgt ctgaggccag cgtcaacaac
1141 cttatggcta agccaaagc ggaccgagag cacgcacccc agcagaaatc gggagagaat
1201 gccaacatcc agccaacat ccagctgatc ctccgggcgg agcccactgt cacaaacatc
1261 ctcaagacga tggatgcaga ccactctaag tcaccggagg gactgctggg agtcctggc
1321 cacatgctgt cgggaagag tctgacttg ctgctgctg cgccgccgc cactggaaag
1381 ctgaaatcct tcgcccgaa attcatcaat ttgaatgaat tcacaaccta tgcagcgaa
1441 gaaagcacca aaccgcctc cgtccgggcc ctgctgtttg acatctcctt cctcatgctg
1501 tgccatgtgg ccagaccta tggttcagag tgattctgt ccgagtcgcg ccaggagct
1561 gaggtgccct tcttcgagac ctggatgcag acctgcatgc ctgaggaggg caagatcctg
```

FIG. 3B

```
1621  aaccctgacc  acccctgctt  ccgcccgac  tccaccaaag  tggagtccct  ggtggccctg
1681  ctcaacaact  cctcggagat  gaagctagtg  cagatgaagt  ggcatgaggc  ctgtctcagc
1741  atctcagccg  ccatcttgga  aatcctcaat  gcctgggaga  atggggtcct  ggccttcgag
1801  tccatccaga  aaatcactga  taacatcaaa  gggaaggtat  gcagtctggc  ggtgtgtgct
1861  gtggcttggc  ttgtggccca  cgtccggatg  ctggggctgg  atgagcgtga  gaagtcgctg
1921  cagatgatcc  gccagctggc  agggccactg  tttagtgaga  acaccctgca  gttctacaat
1981  gagagggtgg  tgatcatgaa  ctcgatcctg  gagcgcatgt  gtgccgacgt  gctgcagcag
2041  acagccacgc  agatcaagtt  tccctccacc  ggggtggaca  caatgcccta  ctggaacctg
2101  ctgccccca  agcggcccat  tcccctgaca  ctctttgaca  tcttttgccaa  ggtgctggag
2161  aagggctggg  tggacagccg  ctccaacaca  cctgattaag  ccctgctgca  catgggcggc
2221  gtctactggt  tctgcaacaa  cagtggagct  gctctactcc  aggagacgcg  gaaggagcac
2281  acgctgcggg  cagtgcgggt  tgggccacat  atcttctgcc  tggacatgca  gcaagtgacc
2341  ctgcctccgc  tggccacat  cctacctgcc  ctgctcactg  actcctccaa  gtggcacacag
2401  ctcatggacc  ccccgggcac  tgctcttgcc  aagctgccgg  tgtggtgtgc  cctcagttcc
2461  tactcctccc  acaagggaca  ggcgtccacc  cgccagaaga  agagacaccg  cgaagacatt
2521  gaggattata  tcagcctctt  ccccctggac  gatgcgagc  cttcgaagtt  gatgcgactg
2581  ctgagctcta  atgaggacga  tgccaacatc  ctttcgagcc  ccacagaccg  atccatgagc
2641  agctccctct  cagcctctca  gctcacacg  gtcaacatgc  gggaccctct  gaaccgagtc
2701  ctgccaaac  tgttcctgct  catctcctcc  atcctgggt  ctcgcaccgc  tggccccac
2761  accagttcg  tgcagtgtt  catgaggag  tgtgtggact  gcctggagca  gggtggccgt
2821  ggcagcgtcc  tgcagttcat  gcccttcacc  accgtgtcgg  aactggtgaa  ggtgtcagcc
2881  atgtccagcc  ccaaggtggt  tctgccatc  tctgcccatc  acggacctca  gcctgcccct  gggccgccag
2941  gtggctgcta  aagccattgc  tgcactctga
```

FIG. 4

/translation="MKVVNLKQAILQAWKERWSDYQWAINMKKFFPKGATWDILNLAD
ALLEQAMIGPSPNPLILSYLKYAISSQMVSYSSVLTAISKFDDFSRDLCVQALLDIMD
MFCDRLSCHGKAEECIGLCRALLSALHWLLRCTAASAERLREGLEAGTPAAGEKQLAM
CLQRLEKTLSSTKNRALLHIAKLEEASSWTAIEHSLLKLGEILANLSNPQLRSQAEQC
GTLIRSIPTMLSVHAEQMHKTGFPTVHAVILLEGTMNLTGETQSLVEQLTMVKRMQHI
PTPLFVLEIWKACFVGLIESPEGTEELKWTAFTFLKIPQVLVKLKKYSHGDKDFTEDV
NCAFEFLLKLTPLLDKADQRCNCDCTNFLLQECGKQGLLSEASVNNLMAKRKADREHA
PQQKSGENANIQPNIQLILRAEPTVTNILKTMDADHSKSPEGLLGVLGHMLSGKSLDL
LLAAAAATGKLKSFARKFINLNEFTTYGSEESTKPASVRALLFDISFLMLCHVAQTYG
SEVILSESRTGAEVPFFETWMQTCMPEEGKILNPDHPCFRPDSTKVESLVALLNNSSE
MKLVQMKWHEACLSISAAILEILNAWENGVLAFESIQKITDNIKGKVCSLAVCAVAWL
VAHVRMLGLDEREKSLQMIRQLAGPLFSENTLQFYNERVVIMNSILERMCADVLQQTA
TQIKFPSTGVDTMPYWNLLPPKRPIKEVLTDIFAKVLEKGWVDSRSIHIFDTLLHMGG
VYWFCNNLIKELLKETRKEHTLRAVELLYSIFCLDMQQVTLVLLGHILPGLLTDSSKW
HSLMDPPGTALAKLAVWCALSSYSSHKGQASTRQKKRHREDIEDYISLFPLDDVQPSK
LMRLLSSNEDDANILSSPTDRSMSSSLSASQLHTVNMRDPLNRVLANLFLLISSILGS
RTAGPHTQFVQWFMEECVDCLEQGGRGSVLQFMPFTTVSELVKVSAMSSPKVVLAITD
LSLPLGRQVAAKAIAAL"

FIG. 5A

TRAP220

```
MKAQGETEESEKLSKMSSLLERLHAKFNQNRPWSETIKLVRQVMEKRVVMSSGGHQHLVS    60
CLETLQKALKVTSLPAMTDRLESIARQNGLGSHLSASGTECYITSDMFYVEVQLDPAGQL   120
CDVKVAHHGENPVSCPELVQQLREKNFDEFSKHLKGLVNLYNLPGDNKLKTKMYLALQSL   180
EQDLSKMAIMYWKATNAGPLDKILHGSVGYLTPRSQGHLMNLKYYVSPSDLLDDKTASPI   240
ILHENNVSRSLGMNASVTIEGTSAVYKLPIAPLIMGSHPVDNKWTPSFSSITSANSVDLP   300
ACFFLKFPQPIPVSRAFVQKLQNCTGIPLFETQPTYAPLYELITQFELSKDPDPIPLNHN   360
MRFYAALPGQQHCYFLNKDAPLPDGRSLQGTLVSKITFQHPGRVPLILNLIRHQVAYNTL   420
IGSCVKRTILKEDSPGLLQFEVCPLSESRFSVSFQHPVNDSLVCVVMDVQDSTHVSCKLY   480
KGLSDALICTDDFIAKVVQRCMSIPVTMRAIRRKAETIQADTPALSLIAETVEDMVKKNL   540
PPLAGPGYGMTTGNNPMSGTTTPTNTFPGGPITTLFNMSMSIKDRHESVGHGEDFSKVSQ   600
NPILTSLLQITGNGGSTIGSSPTPPHHTPPPVSSMAGNTKNHPMLMNLLKDNPAQDFSTL   660
YGSSPLERQNSSSGSPRMEICSGSNKTKKKKSSRLPPEKPKHQTEDDFQRELFSMDVDSQ   720
KPIFDVNMTADTLDTPHITPAPSQCSTPPTTYPQPVPHPQPSIQRMVRLSSSDSIGPDVT   780
DILSDIAEEASKLPSTSDDCPAIGTPLRDSSSSGHSQSTLFDSDVFQTNNNENPYTDPAD   840
LIADAAGSPSSDSPTNHFFHDGVDFNPDLLNSQSQSGFGEEYFDESSQSGDNDDFKGFAS   900
QALNTLGVPMLGGDNGETKFKGNNQADTVDFSIISVAGKALAPADLMEHHSGSQGPLLTT   960
GDLGKEKTQKRVKEGNGTSNSTLSGPGLDSKPGKRSRTPSNDGKSKDKPPKRKKADTEGK  1020
SPSHSSSNRPFTPPPTSTGGSKSPGSAGRSQTPPGVATPPIPKITIQIPKGTVMVGKPSSH 1080
SQYTSSGSVSSSGSKSHHSHSSSSSASTSGKMKSSKSEGSSSSKLSSSMYSSQGSSGS   1140
SQSKNSSQSGGKPGSSPITKHGLSSGSSSTKMKPQGKPSSLMNPSLSKPNISPSHSRPPG  1200
GSDKLASPMKPVPGTPPSSKAKSPISSGSGGSHMSGTSSSSGMKSSSGLGSSGSLSQKTP  1260
PSSNSCTASSSSFSSSGSSMSSSQNQHGSSKGKSPSRNKKPSLTAVIDKLKHGVVTSGPG  1320
GEDPLDGQMGVSTNSSSHPMSSKHNMSGGEFQGKREKSDKDKSKVSTSGSSVDSSKKTSE  1380
SKNVGSTSVAKIIISKHDGGSPSIKAKVTLQKPGESSGEGLRPQMASSKNYGSPLISGST  1440
PKHERGSPSHSKSPAYTPQNLDSESESGSSIAEKSYQNSPSSDDGIRPLPEYSTEKHKKH  1500
KKEKKKVKDKDRDRDRDKDRDKKKSHSIKPESWSKSPISSDQSLSMTSNTILSADRPSRL  1560
SPDFMIGEEDDDLMDVALIGN
```

TRAP100

```
MKVVNLKQAILQAWKERWSDYQWAINMKKFFPKGATWDILNLADALLEQAMIGPSPNPLI    60
LSYLKYAISSQMVSYSSVLTAISKFDDFSRDLCVQALLDIMDMFCDRLSCHGKAEECIGL   120
CRALLSALHWLLRCTAASAERLREGLEAGTPAAGEKQLAMCLQRLEKTLSSTKNRALLHI   180
AKLEEASSWTAIEHSLLKLGEILANLSNPQLRSQAEQCGTLIRSIPTMLSVHAEQMHKTG   240
FPTVHAVILLEGTMNLTGETQSLVEQLTMVKRMQHIPTPLFVLEIWKACFVGLIESPEGT   300
EELKWTAFTFLKIPQVLVKLKKYSHGKDFTEDVNCAFEFLLKLTPLLDKADQRCNCDCT   360
NFLLQECGKQGLLSEASVNNLMAKRKADREHAPQQKSGENANIQPNIQLILRAEPTVTNI   420
LKTMDADHSKSPEGLLGVLGHMLSGKSLDLLIAAAAATGKLKSFARKFINLNEFTTYGSE   480
ESTKPASVRALLFDISFLMLCHVAQTYGSEVILSESRTGAEVPFFETWMQTCMPEEGKIL   540
NPDHPCFRPDSTKVESLVALLNNSSEMKLVQMKWHEACLSISAAILEILNAWENGVLAFE   600
SIQKITDNIKGKVCSLAVCAVAWLVAHVRMLGLDEREKSLQMIRQLAGPLFSENTLQFYN   660
ERVVIMNSILERMCADVLQQTATQIKFPSTGVDTMPYWNLLPPKRPIKEVLTDIFAKVLE   720
KGWVDSRSIHIFDTLLHMGGVYWFCNNLIKELLKETRKEHTLRAVELLYSIFCLDMQQVT   780
LVLLGHILPGLLTDSSKWHSLMDPPGTALAKLAVWCALSSYSSHKGQASTRQKKRHREDI   840
EDYISLFPLDDVQPSKLMRLLSSNEDDANILSSPTDRSMSSSLSASQLHTVNMRDPLNRV   900
LANLFLLISSILGSRTAGPHTQFVQWFMEECVDCLEQGGRGSVLQFMPFTTVSELVKVSA   960
MSSPKVVLAITDLSLPLGRQVAAKAIAAL
```

FIG. 6A
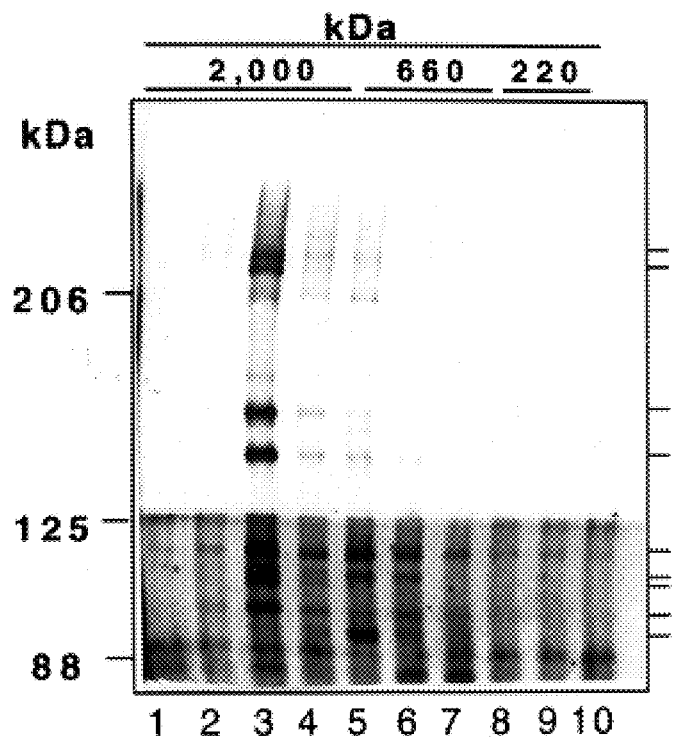
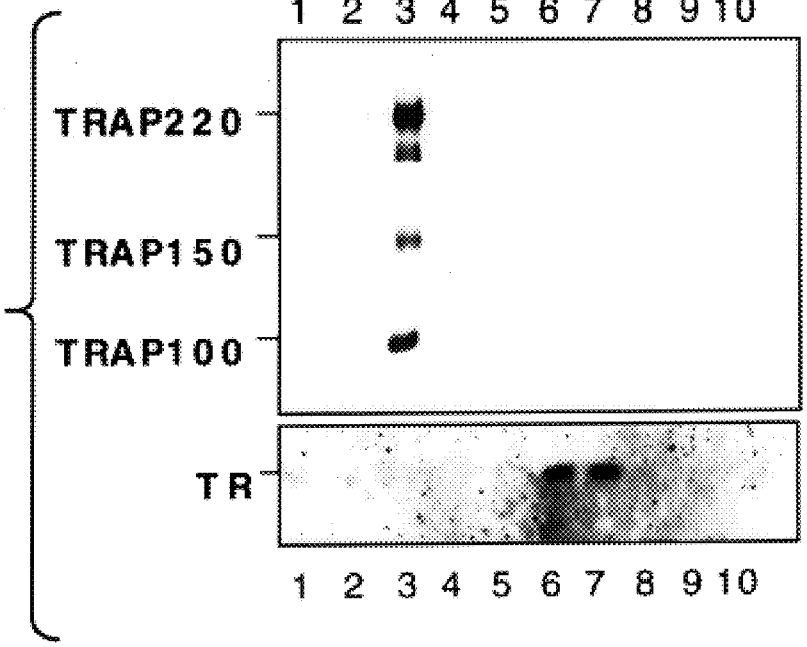
FIG. 6B

SEQUENCE LISTING

```
<160> NUMBER OF SEQ ID NOS: 51

<210> SEQ ID NO: 1
<211> LENGTH: 5008
<212> TYPE: DNA
<213> ORGANISM: Homo sapiens
<220> FEATURE:
<221> NAME/KEY: CDS
<222> LOCATION: (193)..(4938)

<400> SEQUENCE: 1
cggacaggcg cacacgacgc ctcgagcacc cttctcttct tgccgccggg gacttcagat      60
tgatccttcc cgggaagagt agggactgct ggtgccctgc gtcccgggat cccgagccaa     120
cttgtttcct ccgttagtgg tggggaaggg cttatccttt tgtggcggat ctagcttctc     180
ctcgccttca gg atg aaa gct cag ggg gaa acc gag gag tca gaa aag ctg    231
              Met Lys Ala Gln Gly Glu Thr Glu Glu Ser Glu Lys Leu
                1               5                  10 agt aag atg agt tct ctc ctg gaa cgg ctc cat gca aaa ttt aac caa       279
Ser Lys Met Ser Ser Leu Leu Glu Arg Leu His Ala Lys Phe Asn Gln
 15                  20                  25 aat aga ccc tgg agt gaa acc att aag ctt gtg cgt caa gtc atg gag       327
Asn Arg Pro Trp Ser Glu Thr Ile Lys Leu Val Arg Gln Val Met Glu
 30                  35                  40                  45 aag agg gtt gtg atg agt tct gga ggg cat caa cat ttg gtc agc tgt       375
Lys Arg Val Val Met Ser Ser Gly Gly His Gln His Leu Val Ser Cys
                 50                  55                  60 ttg gag aca ttg cag aag gct ctc aaa gta aca tct tta cca gca atg       423
Leu Glu Thr Leu Gln Lys Ala Leu Lys Val Thr Ser Leu Pro Ala Met
                 65                  70                  75 act gat cgt ttg gag tcc ata gca aga cag aat gga ctg ggc tct cat       471
Thr Asp Arg Leu Glu Ser Ile Ala Arg Gln Asn Gly Leu Gly Ser His
             80                  85                  90 ctc agt gcc agt ggc act gaa tgt tac atc acg tca gat atg ttc tat       519
Leu Ser Ala Ser Gly Thr Glu Cys Tyr Ile Thr Ser Asp Met Phe Tyr
             95                 100                 105 gtg gaa gtg cag tta gat cct gca gga cag ctt tgt gat gta aaa gtg       567
Val Glu Val Gln Leu Asp Pro Ala Gly Gln Leu Cys Asp Val Lys Val
110                 115                 120                 125 gct cac cat ggg gag aat cct gtg agc tgt ccg gag ctt gta cag cag       615
Ala His His Gly Glu Asn Pro Val Ser Cys Pro Glu Leu Val Gln Gln
                130                 135                 140 cta agg gaa aaa aat ttt gat gaa ttt tct aag cac ctt aag ggc ctt       663
Leu Arg Glu Lys Asn Phe Asp Glu Phe Ser Lys His Leu Lys Gly Leu
                145                 150                 155
```

-continued

```
gtt aat ctg tat aac ctt cca ggg gac aac aaa ctg aag act aaa atg      711
Val Asn Leu Tyr Asn Leu Pro Gly Asp Asn Lys Leu Lys Thr Lys Met
        160                 165                 170 tac ttg gct ctc caa tcc tta gaa caa gat ctt tct aaa atg gca att      759
Tyr Leu Ala Leu Gln Ser Leu Glu Gln Asp Leu Ser Lys Met Ala Ile
175                 180                 185 atg tac tgg aaa gca act aat gct ggt ccc ttg gat aag att ctt cat      807
Met Tyr Trp Lys Ala Thr Asn Ala Gly Pro Leu Asp Lys Ile Leu His
190                 195                 200                 205 gga agt gtt ggc tat ctc aca cca agg agt ggg ggt cat tta atg aac      855
Gly Ser Val Gly Tyr Leu Thr Pro Arg Ser Gly Gly His Leu Met Asn
            210                 215                 220 ctg aag tac tat gtc tct cct tct gac cta ctg gat gac aag act gca      903
Leu Lys Tyr Tyr Val Ser Pro Ser Asp Leu Leu Asp Asp Lys Thr Ala
                225                 230                 235 tct ccc atc att ttg cat gag aat aat gtt tct cga tct ttg ggc atg      951
Ser Pro Ile Ile Leu His Glu Asn Asn Val Ser Arg Ser Leu Gly Met
        240                 245                 250 aat gca tca gtg aca att gaa gga aca tct gct gtg tac aaa ctc cca      999
Asn Ala Ser Val Thr Ile Glu Gly Thr Ser Ala Val Tyr Lys Leu Pro
255                 260                 265 att gca cca tta att atg ggg tca cat cca gtt gac aat aaa tgg acc     1047
Ile Ala Pro Leu Ile Met Gly Ser His Pro Val Asp Asn Lys Trp Thr
270                 275                 280                 285 cct tcc ttc tcc tca atc acc agt gcc aac agt gtt gat ctt cct gcc     1095
Pro Ser Phe Ser Ser Ile Thr Ser Ala Asn Ser Val Asp Leu Pro Ala
            290                 295                 300 tgt ttc ttc ttg aaa ttt ccc cag cca atc cca gta tct aga gca ttt     1143
Cys Phe Phe Leu Lys Phe Pro Gln Pro Ile Pro Val Ser Arg Ala Phe
                305                 310                 315 gtt cag aaa ctg cag aac tgc aca gga att cca ttg ttt gaa act caa     1191
Val Gln Lys Leu Gln Asn Cys Thr Gly Ile Pro Leu Phe Glu Thr Gln
        320                 325                 330 cca act tat gca ccc ctg tat gaa ctg atc act cag ttt gag cta tca     1239
Pro Thr Tyr Ala Pro Leu Tyr Glu Leu Ile Thr Gln Phe Glu Leu Ser
335                 340                 345 aag gac cct gac ccc ata cct ttg aat cac aac atg aga ttt tat gct     1287
Lys Asp Pro Asp Pro Ile Pro Leu Asn His Asn Met Arg Phe Tyr Ala
350                 355                 360                 365 gct ctt cct ggt cag cag cac tgc tat ttc ctc aac aag gat gct cct     1335
Ala Leu Pro Gly Gln Gln His Cys Tyr Phe Leu Asn Lys Asp Ala Pro
            370                 375                 380 ctt cca gat ggc cga agt cta cag gga acc ctt gtt agc aaa atc acc     1383
Leu Pro Asp Gly Arg Ser Leu Gln Gly Thr Leu Val Ser Lys Ile Thr
                385                 390                 395 ttt cag cac cct ggc cga gtt cct ctt atc cta aat ctg atc aga cac     1431
Phe Gln His Pro Gly Arg Val Pro Leu Ile Leu Asn Leu Ile Arg His
        400                 405                 410 caa gtg gcc tat aac acc ctc att gga agc tgt gtc aaa aga act att     1479
Gln Val Ala Tyr Asn Thr Leu Ile Gly Ser Cys Val Lys Arg Thr Ile
415                 420                 425 ctg aaa gaa gat tct cct ggg ctt ctc caa ttt gaa gtg tgt cct ctc     1527
Leu Lys Glu Asp Ser Pro Gly Leu Leu Gln Phe Glu Val Cys Pro Leu
430                 435                 440                 445 tca gag tct cgt ttc agc gta tct ttt cag cac cct gtg aat gac tcc     1575
Ser Glu Ser Arg Phe Ser Val Ser Phe Gln His Pro Val Asn Asp Ser
            450                 455                 460 ctg gtg tgt gtg gta atg gat gtg cag gac tca aca cat gtg agc tgt     1623
Leu Val Cys Val Val Met Asp Val Gln Asp Ser Thr His Val Ser Cys
```

```
                        465                     470                     475
aaa ctc tac aaa ggg ctg tcg gat gca ctg atc tgc aca gat gac ttc       1671
Lys Leu Tyr Lys Gly Leu Ser Asp Ala Leu Ile Cys Thr Asp Asp Phe
                480                     485                     490 att gcc aaa gtt gtt caa aga tgt atg tcc atc cct gtg acg atg agg       1719
Ile Ala Lys Val Val Gln Arg Cys Met Ser Ile Pro Val Thr Met Arg
        495                     500                     505 gct att cgg agg aaa gct gaa acc att caa gcc gac acc cca gca ctg       1767
Ala Ile Arg Arg Lys Ala Glu Thr Ile Gln Ala Asp Thr Pro Ala Leu
510                     515                     520                     525 tcc ctc att gca gag aca gtt gaa gac atg gtg aaa aag aac ctg ccc       1815
Ser Leu Ile Ala Glu Thr Val Glu Asp Met Val Lys Lys Asn Leu Pro
                530                     535                     540 ccg cta gca ggc cca ggg tat ggc atg acc aca ggc aac aac cca atg       1863
Pro Leu Ala Gly Pro Gly Tyr Gly Met Thr Thr Gly Asn Asn Pro Met
        545                     550                     555 agt ggt acc act aca cca acc aac acc ttt ccg ggg ggt ccc att acc       1911
Ser Gly Thr Thr Thr Pro Thr Asn Thr Phe Pro Gly Gly Pro Ile Thr
            560                     565                     570 acc ttg ttt aat atg agc atg agc atc aaa gat cgg cat gag tcg gtg       1959
Thr Leu Phe Asn Met Ser Met Ser Ile Lys Asp Arg His Glu Ser Val
        575                     580                     585 ggc cat ggg gag gac ttc agc aag gtg tct cag aac cca att ctt acc       2007
Gly His Gly Glu Asp Phe Ser Lys Val Ser Gln Asn Pro Ile Leu Thr
590                     595                     600                     605 agt ttg ttg caa atc aca ggg aac ggg ggg tct acc att ggc tcg agt       2055
Ser Leu Leu Gln Ile Thr Gly Asn Gly Gly Ser Thr Ile Gly Ser Ser
                610                     615                     620 ccg acc cct cct cat cac acg ccg cca cct gtc tct tcg atg gcc ggc       2103
Pro Thr Pro Pro His His Thr Pro Pro Pro Val Ser Ser Met Ala Gly
        625                     630                     635 aac acc aag aac cac ccg atg ctc atg aac ctt ctt aaa gat aat cct       2151
Asn Thr Lys Asn His Pro Met Leu Met Asn Leu Leu Lys Asp Asn Pro
640                     645                     650 gcc cag gat ttc tca acc ctt tat gga agc agc cct tta gaa agg cag       2199
Ala Gln Asp Phe Ser Thr Leu Tyr Gly Ser Ser Pro Leu Glu Arg Gln
        655                     660                     665 aac tcc tct tcc ggc tca ccc cgc atg gaa ata tgc tcg ggg agc aac       2247
Asn Ser Ser Ser Gly Ser Pro Arg Met Glu Ile Cys Ser Gly Ser Asn
670                     675                     680                     685 aag acc aag aaa aag aag tca tca aga tta cca cct gag aaa cca aag       2295
Lys Thr Lys Lys Lys Lys Ser Ser Arg Leu Pro Pro Glu Lys Pro Lys
                690                     695                     700 cac cag act gaa gat gac ttt cag agg gag cta ttt tca atg gat gtt       2343
His Gln Thr Glu Asp Asp Phe Gln Arg Glu Leu Phe Ser Met Asp Val
        705                     710                     715 gac tca cag aag cct atc ttt gat gtc aac atg aca gct gac aca ctg       2391
Asp Ser Gln Lys Pro Ile Phe Asp Val Asn Met Thr Ala Asp Thr Leu
        720                     725                     730 gat acg cca cac atc act cca gct cca agc cag tgt agc act ccc cca       2439
Asp Thr Pro His Ile Thr Pro Ala Pro Ser Gln Cys Ser Thr Pro Pro
        735                     740                     745 aca act tac cca caa cca gta cct cac ccc caa ccc agt att caa agg       2487
Thr Thr Tyr Pro Gln Pro Val Pro His Pro Gln Pro Ser Ile Gln Arg
750                     755                     760                     765 atg gtc cga cta tcc agt tca gac agc att ggc cca gat gta act gac       2535
Met Val Arg Leu Ser Ser Ser Asp Ser Ile Gly Pro Asp Val Thr Asp
                770                     775                     780 atc ctt tca gac att gca gaa gaa gct tct aaa ctt ccc agc act agt       2583
```

-continued

```
                Ile Leu Ser Asp Ile Ala Glu Glu Ala Ser Lys Leu Pro Ser Thr Ser
                            785                 790                 795 gat gat tgc cca gcc att ggc acc cct ctt cga gat tct tca agc tct            2631
Asp Asp Cys Pro Ala Ile Gly Thr Pro Leu Arg Asp Ser Ser Ser Ser
            800                 805                 810 ggg cat tct cag agt acc ctg ttt gac tct gat gtc ttt caa act aac            2679
Gly His Ser Gln Ser Thr Leu Phe Asp Ser Asp Val Phe Gln Thr Asn
815                 820                 825 aat aat gaa aat cca tac act gat cca gct gat ctt att gca gat gct            2727
Asn Asn Glu Asn Pro Tyr Thr Asp Pro Ala Asp Leu Ile Ala Asp Ala
830                 835                 840                 845 gct gga agc ccc agt agt gac tct cct acc aat cat ttt ttt cat gat            2775
Ala Gly Ser Pro Ser Ser Asp Ser Pro Thr Asn His Phe Phe His Asp
            850                 855                 860 gga gta gat ttc aat cct gat tta ttg aac agc cag agc caa agt ggt            2823
Gly Val Asp Phe Asn Pro Asp Leu Leu Asn Ser Gln Ser Gln Ser Gly
            865                 870                 875 ttt gga gaa gaa tat ttt gat gaa agc agc caa agt ggg gat aat gat            2871
Phe Gly Glu Glu Tyr Phe Asp Glu Ser Ser Gln Ser Gly Asp Asn Asp
            880                 885                 890 gat ttc aaa gga ttt gca tct cag gca cta aat act ttg ggg gtg cca            2919
Asp Phe Lys Gly Phe Ala Ser Gln Ala Leu Asn Thr Leu Gly Val Pro
895                 900                 905 atg ctt gga ggt gat aat ggg gag acc aag ttt aag ggc aat aac caa            2967
Met Leu Gly Gly Asp Asn Gly Glu Thr Lys Phe Lys Gly Asn Asn Gln
910                 915                 920                 925 gcc gac aca gtt gat ttc agt att att tca gta gcc ggc aaa gct tta            3015
Ala Asp Thr Val Asp Phe Ser Ile Ile Ser Val Ala Gly Lys Ala Leu
            930                 935                 940 gct cct gca gat ctt atg gag cat cac agt ggt agt cag ggt cct tta            3063
Ala Pro Ala Asp Leu Met Glu His His Ser Gly Ser Gln Gly Pro Leu
            945                 950                 955 ctg acc act ggg gac tta ggg aaa gaa aag act caa aag agg gta aag            3111
Leu Thr Thr Gly Asp Leu Gly Lys Glu Lys Thr Gln Lys Arg Val Lys
            960                 965                 970 gaa ggc aat ggc acc agt aat agt act ctc tcg ggg ccc gga tta gac            3159
Glu Gly Asn Gly Thr Ser Asn Ser Thr Leu Ser Gly Pro Gly Leu Asp
975                 980                 985 agc aaa cca ggg aag cgc agt cgg acc cct tct aat gat ggg aaa agc            3207
Ser Lys Pro Gly Lys Arg Ser Arg Thr Pro Ser Asn Asp Gly Lys Ser
990                 995                 1000                1005 aaa gat aag cct cca aag cgg aag aag gca gac act gag gga aag tct            3255
Lys Asp Lys Pro Pro Lys Arg Lys Lys Ala Asp Thr Glu Gly Lys Ser
            1010                1015                1020 cca tct cat agt tct tct aac aga cct ttt acc cca cct acc agt aca            3303
Pro Ser His Ser Ser Ser Asn Arg Pro Phe Thr Pro Pro Thr Ser Thr
            1025                1030                1035 ggt gga tct aaa tcg cca ggc agt gca gga aga tct cag act ccc cca            3351
Gly Gly Ser Lys Ser Pro Gly Ser Ala Gly Arg Ser Gln Thr Pro Pro
            1040                1045                1050 ggt gtt gcc aca cca ccc att ccc aaa atc act att cag att cct aag            3399
Gly Val Ala Thr Pro Pro Ile Pro Lys Ile Thr Ile Gln Ile Pro Lys
            1055                1060                1065 gga aca gtg atg gtg ggc aag cct tcc tct cac agt cag tat acc agc            3447
Gly Thr Val Met Val Gly Lys Pro Ser Ser His Ser Gln Tyr Thr Ser
1070                1075                1080                1085 agt ggt tct gtg tct tcc tca ggc agc aaa agc cac cat agc cat tct            3495
Ser Gly Ser Val Ser Ser Ser Gly Ser Lys Ser His His Ser His Ser
            1090                1095                1100
```

```
tcc tcc tct tcc tca tct gct tcc acc tca ggg aag atg aaa agc agt      3543
Ser Ser Ser Ser Ser Ser Ala Ser Thr Ser Gly Lys Met Lys Ser Ser
        1105                1110                1115 aaa tca gaa ggt tca tca agt tcc aag tta agt agc agt atg tat tct      3591
Lys Ser Glu Gly Ser Ser Ser Lys Leu Ser Ser Ser Met Tyr Ser
    1120                1125                1130 agc cag ggg tct tct gga tct agc cag tcc aaa aat tca tcc cag tct      3639
Ser Gln Gly Ser Ser Gly Ser Ser Gln Ser Lys Asn Ser Ser Gln Ser
        1135                1140                1145 ggg ggg aag cca ggc tcc tct ccc ata acc aag cat gga ctg agc agt      3687
Gly Gly Lys Pro Gly Ser Ser Pro Ile Thr Lys His Gly Leu Ser Ser
1150                1155                1160                1165 ggc tct agc agc acc aag atg aaa cct caa gga aag cca tca tca ctt      3735
Gly Ser Ser Ser Thr Lys Met Lys Pro Gln Gly Lys Pro Ser Ser Leu
        1170                1175                1180 atg aat cct tct tta agt aaa cca aac ata tcc cct tct cat tca agg      3783
Met Asn Pro Ser Leu Ser Lys Pro Asn Ile Ser Pro Ser His Ser Arg
        1185                1190                1195 cca cct gga ggc tct gac aag ctt gcc tct cca atg aag cct gtt cct      3831
Pro Pro Gly Gly Ser Asp Lys Leu Ala Ser Pro Met Lys Pro Val Pro
        1200                1205                1210 gga act cct cca tcc tct aaa gcc aag tcc cct atc agt tca ggt tct      3879
Gly Thr Pro Pro Ser Ser Lys Ala Lys Ser Pro Ile Ser Ser Gly Ser
    1215                1220                1225 ggt ggt tct cat atg tct gga act agt tca agc tct ggc atg aag tca      3927
Gly Gly Ser His Met Ser Gly Thr Ser Ser Ser Ser Gly Met Lys Ser
1230                1235                1240                1245 tct tca ggg tta gga tcc tca ggc tcg ttg tcc cag aaa act ccc cca      3975
Ser Ser Gly Leu Gly Ser Ser Gly Ser Leu Ser Gln Lys Thr Pro Pro
        1250                1255                1260 tca tct aat tcc tgt acg gca tct tcc tcc tcc ttt tcc tca agt ggc      4023
Ser Ser Asn Ser Cys Thr Ala Ser Ser Ser Ser Phe Ser Ser Ser Gly
        1265                1270                1275 tct tcc atg tca tcc tct cag aac cag cat ggg agt tct aaa gga aaa      4071
Ser Ser Met Ser Ser Ser Gln Asn Gln His Gly Ser Ser Lys Gly Lys
        1280                1285                1290 tct ccc agc aga aac aag aag ccg tcc ttg aca gct gtc ata gat aaa      4119
Ser Pro Ser Arg Asn Lys Lys Pro Ser Leu Thr Ala Val Ile Asp Lys
    1295                1300                1305 ctg aag cat ggg gtt gtc acc agt ggc cct ggg ggt gaa gac cca ctg      4167
Leu Lys His Gly Val Val Thr Ser Gly Pro Gly Gly Glu Asp Pro Leu
1310                1315                1320                1325 gac ggc cag atg ggg gtg agc aca aat tct tcc agc cat cct atg tcc      4215
Asp Gly Gln Met Gly Val Ser Thr Asn Ser Ser Ser His Pro Met Ser
        1330                1335                1340 tcc aaa cat aac atg tca gga gga gag ttt cag ggc aag cgt gag aaa      4263
Ser Lys His Asn Met Ser Gly Gly Glu Phe Gln Gly Lys Arg Glu Lys
        1345                1350                1355 agt gat aaa gac aaa tca aag gtt tcc acc tcc ggg agt tca gtg gat      4311
Ser Asp Lys Asp Lys Ser Lys Val Ser Thr Ser Gly Ser Ser Val Asp
        1360                1365                1370 tct tct aag aag acc tca gag tca aaa aat gtg ggg agc aca agt gtg      4359
Ser Ser Lys Lys Thr Ser Glu Ser Lys Asn Val Gly Ser Thr Ser Val
    1375                1380                1385 gca aaa att atc atc agt aag cat gat gga ggc tcc cct agc att aaa      4407
Ala Lys Ile Ile Ile Ser Lys His Asp Gly Gly Ser Pro Ser Ile Lys
1390                1395                1400                1405 gcc aaa gtg act ttg cag aaa cct ggg gaa agt agt gga gaa ggg ctt      4455
Ala Lys Val Thr Leu Gln Lys Pro Gly Glu Ser Ser Gly Glu Gly Leu
        1410                1415                1420
```

-continued

```
agg cct caa atg gct tct tct aaa aac tat ggc tct cca ctc atc agt      4503
Arg Pro Gln Met Ala Ser Ser Lys Asn Tyr Gly Ser Pro Leu Ile Ser
        1425                1430                1435 ggt tcc act cca aag cat gag cgt ggc tct ccc agc cat agt aag tca      4551
Gly Ser Thr Pro Lys His Glu Arg Gly Ser Pro Ser His Ser Lys Ser
    1440                1445                1450 cca gca tat acc ccc cag aat ctg gac agt gaa agt gag tca ggc tcc      4599
Pro Ala Tyr Thr Pro Gln Asn Leu Asp Ser Glu Ser Glu Ser Gly Ser
1455                1460                1465 tcc ata gca gag aaa tct tat cag aat agt ccc agc tca gac gat ggt      4647
Ser Ile Ala Glu Lys Ser Tyr Gln Asn Ser Pro Ser Ser Asp Asp Gly
1470                1475                1480                1485 atc cga cca ctt cca gaa tac agc aca gag aaa cat aag aag cac aaa      4695
Ile Arg Pro Leu Pro Glu Tyr Ser Thr Glu Lys His Lys Lys His Lys
            1490                1495                1500 aag gaa aag aag aaa gta aaa gac aaa gat agg gac cga gac cgg gac      4743
Lys Glu Lys Lys Lys Val Lys Asp Lys Asp Arg Asp Arg Asp Arg Asp
        1505                1510                1515 aaa gac cga gac aag aaa aaa tct cat agc atc aag cca gag agt tgg      4791
Lys Asp Arg Asp Lys Lys Lys Ser His Ser Ile Lys Pro Glu Ser Trp
    1520                1525                1530 tcc aaa tca ccc atc tct tca gac cag tcc ttg tct atg aca agt aac      4839
Ser Lys Ser Pro Ile Ser Ser Asp Gln Ser Leu Ser Met Thr Ser Asn
1535                1540                1545 aca atc tta tct gca gac aga ccc tca agg ctc agc cca gac ttt atg      4887
Thr Ile Leu Ser Ala Asp Arg Pro Ser Arg Leu Ser Pro Asp Phe Met
1550                1555                1560                1565 att ggg gag gaa gat gat gat ctt atg gat gtg gcc ctg att ggg aat      4935
Ile Gly Glu Glu Asp Asp Asp Leu Met Asp Val Ala Leu Ile Gly Asn
            1570                1575                1580 tag gaaccttatt tcctaaaaga aacagggcca gaggaaaaaa aactattgat           4988
aagtttatag gcaaaccacc                                                5008

<210> SEQ ID NO: 2
<211> LENGTH: 1581
<212> TYPE: PRT
<213> ORGANISM: Homo sapiens

<400> SEQUENCE: 2

Met Lys Ala Gln Gly Glu Thr Glu Glu Ser Glu Lys Leu Ser Lys Met
1               5                   10                  15

Ser Ser Leu Leu Glu Arg Leu His Ala Lys Phe Asn Gln Asn Arg Pro
            20                  25                  30

Trp Ser Glu Thr Ile Lys Leu Val Arg Gln Val Met Glu Lys Arg Val
        35                  40                  45

Val Met Ser Ser Gly Gly His Gln His Leu Val Ser Cys Leu Glu Thr
    50                  55                  60

Leu Gln Lys Ala Leu Lys Val Thr Ser Leu Pro Ala Met Thr Asp Arg
65                  70                  75                  80

Leu Glu Ser Ile Ala Arg Gln Asn Gly Leu Gly Ser His Leu Ser Ala
                85                  90                  95

Ser Gly Thr Glu Cys Tyr Ile Ser Asp Met Phe Tyr Val Glu Val
            100                 105                 110

Gln Leu Asp Pro Ala Gly Gln Leu Cys Asp Val Lys Val Ala His His
        115                 120                 125

Gly Glu Asn Pro Val Ser Cys Pro Glu Leu Val Gln Gln Leu Arg Glu
    130                 135                 140
```

```
Lys Asn Phe Asp Glu Phe Ser Lys His Leu Lys Gly Leu Val Asn Leu
145                 150                 155                 160

Tyr Asn Leu Pro Gly Asp Asn Lys Leu Lys Thr Lys Met Tyr Leu Ala
            165                 170                 175

Leu Gln Ser Leu Glu Gln Asp Leu Ser Lys Met Ala Ile Met Tyr Trp
        180                 185                 190

Lys Ala Thr Asn Ala Gly Pro Leu Asp Lys Ile Leu His Gly Ser Val
    195                 200                 205

Gly Tyr Leu Thr Pro Arg Ser Gly His Leu Met Asn Leu Lys Tyr
    210                 215                 220

Tyr Val Ser Pro Ser Asp Leu Leu Asp Lys Thr Ala Ser Pro Ile
225                 230                 235                 240

Ile Leu His Glu Asn Asn Val Ser Arg Ser Leu Gly Met Asn Ala Ser
                245                 250                 255

Val Thr Ile Glu Gly Thr Ser Ala Val Tyr Lys Leu Pro Ile Ala Pro
            260                 265                 270

Leu Ile Met Gly Ser His Pro Val Asp Asn Lys Trp Thr Pro Ser Phe
        275                 280                 285

Ser Ser Ile Thr Ser Ala Asn Ser Val Asp Leu Pro Ala Cys Phe Phe
    290                 295                 300

Leu Lys Phe Pro Gln Pro Ile Pro Val Ser Arg Ala Phe Val Gln Lys
305                 310                 315                 320

Leu Gln Asn Cys Thr Gly Ile Pro Leu Phe Glu Thr Gln Pro Thr Tyr
                325                 330                 335

Ala Pro Leu Tyr Glu Leu Ile Thr Gln Phe Glu Leu Ser Lys Asp Pro
            340                 345                 350

Asp Pro Ile Pro Leu Asn His Asn Met Arg Phe Tyr Ala Ala Leu Pro
        355                 360                 365

Gly Gln Gln His Cys Tyr Phe Leu Asn Lys Asp Ala Pro Leu Pro Asp
    370                 375                 380

Gly Arg Ser Leu Gln Gly Thr Leu Val Ser Lys Ile Thr Phe Gln His
385                 390                 395                 400

Pro Gly Arg Val Pro Leu Ile Leu Asn Leu Ile Arg His Gln Val Ala
                405                 410                 415

Tyr Asn Thr Leu Ile Gly Ser Cys Val Lys Arg Thr Ile Leu Lys Glu
            420                 425                 430

Asp Ser Pro Gly Leu Leu Gln Phe Glu Val Cys Pro Leu Ser Glu Ser
        435                 440                 445

Arg Phe Ser Val Ser Phe Gln His Pro Val Asn Asp Ser Leu Val Cys
    450                 455                 460

Val Val Met Asp Val Gln Asp Ser Thr His Val Ser Cys Lys Leu Tyr
465                 470                 475                 480

Lys Gly Leu Ser Asp Ala Leu Ile Cys Thr Asp Asp Phe Ile Ala Lys
                485                 490                 495

Val Val Gln Arg Cys Met Ser Ile Pro Val Thr Met Arg Ala Ile Arg
            500                 505                 510

Arg Lys Ala Glu Thr Ile Gln Ala Asp Thr Pro Ala Leu Ser Leu Ile
        515                 520                 525

Ala Glu Thr Val Glu Asp Met Val Lys Lys Asn Leu Pro Pro Leu Ala
    530                 535                 540

Gly Pro Gly Tyr Gly Met Thr Thr Gly Asn Asn Pro Met Ser Gly Thr
545                 550                 555                 560
```

-continued

```
Thr Thr Pro Thr Asn Thr Phe Pro Gly Gly Pro Ile Thr Thr Leu Phe
            565                 570                 575
Asn Met Ser Met Ser Ile Lys Asp Arg His Glu Ser Val Gly His Gly
            580                 585                 590
Glu Asp Phe Ser Lys Val Ser Gln Asn Pro Ile Leu Thr Ser Leu Leu
        595                 600                 605
Gln Ile Thr Gly Asn Gly Gly Ser Thr Ile Gly Ser Ser Pro Thr Pro
    610                 615                 620
Pro His His Thr Pro Pro Val Ser Ser Met Ala Gly Asn Thr Lys
625                 630                 635                 640
Asn His Pro Met Leu Met Asn Leu Leu Lys Asp Asn Pro Ala Gln Asp
            645                 650                 655
Phe Ser Thr Leu Tyr Gly Ser Ser Pro Leu Glu Arg Gln Asn Ser Ser
            660                 665                 670
Ser Gly Ser Pro Arg Met Glu Ile Cys Ser Gly Ser Asn Lys Thr Lys
        675                 680                 685
Lys Lys Lys Ser Ser Arg Leu Pro Pro Glu Lys Pro Lys His Gln Thr
    690                 695                 700
Glu Asp Asp Phe Gln Arg Glu Leu Phe Ser Met Asp Val Asp Ser Gln
705                 710                 715                 720
Lys Pro Ile Phe Asp Val Asn Met Thr Ala Asp Thr Leu Asp Thr Pro
            725                 730                 735
His Ile Thr Pro Ala Pro Ser Gln Cys Ser Thr Pro Thr Thr Tyr
            740                 745                 750
Pro Gln Pro Val Pro His Pro Gln Pro Ser Ile Gln Arg Met Val Arg
        755                 760                 765
Leu Ser Ser Asp Ser Ile Gly Pro Asp Val Thr Asp Ile Leu Ser
    770                 775                 780
Asp Ile Ala Glu Ala Ser Lys Leu Pro Ser Thr Ser Asp Asp Cys
785                 790                 795                 800
Pro Ala Ile Gly Thr Pro Leu Arg Asp Ser Ser Ser Gly His Ser
            805                 810                 815
Gln Ser Thr Leu Phe Asp Ser Asp Val Phe Gln Thr Asn Asn Asn Glu
            820                 825                 830
Asn Pro Tyr Thr Asp Pro Ala Asp Leu Ile Ala Asp Ala Ala Gly Ser
        835                 840                 845
Pro Ser Ser Asp Ser Pro Thr Asn His Phe Phe His Asp Gly Val Asp
    850                 855                 860
Phe Asn Pro Asp Leu Leu Asn Ser Gln Ser Gln Ser Gly Phe Gly Glu
865                 870                 875                 880
Glu Tyr Phe Asp Glu Ser Ser Gln Ser Gly Asp Asn Asp Asp Phe Lys
            885                 890                 895
Gly Phe Ala Ser Gln Ala Leu Asn Thr Leu Gly Val Pro Met Leu Gly
            900                 905                 910
Gly Asp Asn Gly Glu Thr Lys Phe Lys Gly Asn Asn Gln Ala Asp Thr
        915                 920                 925
Val Asp Phe Ser Ile Ile Ser Val Ala Gly Lys Ala Leu Ala Pro Ala
    930                 935                 940
Asp Leu Met Glu His His Ser Gly Ser Gln Gly Pro Leu Leu Thr Thr
945                 950                 955                 960
Gly Asp Leu Gly Lys Glu Lys Thr Gln Lys Arg Val Lys Glu Gly Asn
            965                 970                 975
Gly Thr Ser Asn Ser Thr Leu Ser Gly Pro Gly Leu Asp Ser Lys Pro
```

-continued

```
                    980                 985                 990
Gly Lys Arg Ser Arg Thr Pro Ser Asn Asp Gly Lys Ser Lys Asp Lys
            995                1000                1005
Pro Pro Lys Arg Lys Lys Ala Asp Thr Glu Gly Lys Ser Pro Ser His
   1010                1015                1020
Ser Ser Ser Asn Arg Pro Phe Thr Pro Pro Thr Ser Thr Gly Gly Ser
025                1030                1035                1040
Lys Ser Pro Gly Ser Ala Gly Arg Ser Gln Thr Pro Pro Gly Val Ala
           1045                1050                1055
Thr Pro Pro Ile Pro Lys Ile Thr Ile Gln Ile Pro Lys Gly Thr Val
               1060                1065                1070
Met Val Gly Lys Pro Ser Ser His Ser Gln Tyr Thr Ser Ser Gly Ser
   1075                1080                1085
Val Ser Ser Ser Gly Ser Lys Ser His His Ser His Ser Ser Ser Ser
   1090                1095                1100
Ser Ser Ser Ala Ser Thr Ser Gly Lys Met Lys Ser Ser Lys Ser Glu
105                1110                1115                1120
Gly Ser Ser Ser Ser Lys Leu Ser Ser Ser Met Tyr Ser Ser Gln Gly
           1125                1130                1135
Ser Ser Gly Ser Ser Gln Ser Lys Asn Ser Ser Gln Ser Gly Gly Lys
           1140                1145                1150
Pro Gly Ser Ser Pro Ile Thr Lys His Gly Leu Ser Ser Gly Ser Ser
           1155                1160                1165
Ser Thr Lys Met Lys Pro Gln Gly Lys Pro Ser Ser Leu Met Asn Pro
   1170                1175                1180
Ser Leu Ser Lys Pro Asn Ile Ser Pro Ser His Ser Arg Pro Pro Gly
185                1190                1195                1200
Gly Ser Asp Lys Leu Ala Ser Pro Met Lys Pro Val Pro Gly Thr Pro
           1205                1210                1215
Pro Ser Ser Lys Ala Lys Ser Pro Ile Ser Ser Gly Ser Gly Gly Ser
           1220                1225                1230
His Met Ser Gly Thr Ser Ser Ser Gly Met Lys Ser Ser Ser Ser Gly
           1235                1240                1245
Leu Gly Ser Ser Gly Ser Leu Ser Gln Lys Thr Pro Pro Ser Ser Asn
   1250                1255                1260
Ser Cys Thr Ala Ser Ser Ser Ser Phe Ser Ser Ser Gly Ser Ser Met
265                1270                1275                1280
Ser Ser Ser Gln Asn Gln His Gly Ser Ser Lys Gly Lys Ser Pro Ser
               1285                1290                1295
Arg Asn Lys Lys Pro Ser Leu Thr Ala Val Ile Asp Lys Leu Lys His
               1300                1305                1310
Gly Val Val Thr Ser Gly Pro Gly Gly Glu Asp Pro Leu Asp Gly Gln
           1315                1320                1325
Met Gly Val Ser Thr Asn Ser Ser Ser His Pro Met Ser Ser Lys His
   1330                1335                1340
Asn Met Ser Gly Gly Glu Phe Gln Gly Lys Arg Glu Lys Ser Asp Lys
345                1350                1355                1360
Asp Lys Ser Lys Val Ser Thr Ser Gly Ser Ser Val Asp Ser Ser Lys
           1365                1370                1375
Lys Thr Ser Glu Ser Lys Asn Val Gly Ser Thr Ser Val Ala Lys Ile
               1380                1385                1390
Ile Ile Ser Lys His Asp Gly Gly Ser Pro Ser Ile Lys Ala Lys Val
           1395                1400                1405
```

```
Thr Leu Gln Lys Pro Gly Glu Ser Ser Gly Glu Gly Leu Arg Pro Gln
    1410                1415                1420

Met Ala Ser Ser Lys Asn Tyr Gly Ser Pro Leu Ile Ser Gly Ser Thr
425                 1430                1435                1440

Pro Lys His Glu Arg Gly Ser Pro Ser His Ser Lys Ser Pro Ala Tyr
                1445                1450                1455

Thr Pro Gln Asn Leu Asp Ser Glu Ser Glu Ser Gly Ser Ser Ile Ala
            1460                1465                1470

Glu Lys Ser Tyr Gln Asn Ser Pro Ser Ser Asp Asp Gly Ile Arg Pro
        1475                1480                1485

Leu Pro Glu Tyr Ser Thr Glu Lys His Lys Lys His Lys Lys Glu Lys
    1490                1495                1500

Lys Lys Val Lys Asp Lys Asp Arg Asp Arg Asp Arg Asp Lys Asp Arg
505                 1510                1515                1520

Asp Lys Lys Lys Ser His Ser Ile Lys Pro Glu Ser Trp Ser Lys Ser
                1525                1530                1535

Pro Ile Ser Ser Asp Gln Ser Leu Ser Met Thr Ser Asn Thr Ile Leu
            1540                1545                1550

Ser Ala Asp Arg Pro Ser Arg Leu Ser Pro Asp Phe Met Ile Gly Glu
        1555                1560                1565

Glu Asp Asp Asp Leu Met Asp Val Ala Leu Ile Gly Asn
    1570                1575                1580

<210> SEQ ID NO: 3
<211> LENGTH: 2970
<212> TYPE: DNA
<213> ORGANISM: Homo sapiens
<220> FEATURE:
<221> NAME/KEY: CDS
<222> LOCATION: (1)..(2970)

<400> SEQUENCE: 3 atg aag gtg gtc aac ctg aag caa gcc att ttg caa gcc tgg aag gag      48
Met Lys Val Val Asn Leu Lys Gln Ala Ile Leu Gln Ala Trp Lys Glu
  1               5                  10                  15 cgc tgg agt gac tac caa tgg gca atc aac atg aag aaa ttc ttt cct      96
Arg Trp Ser Asp Tyr Gln Trp Ala Ile Asn Met Lys Lys Phe Phe Pro
             20                  25                  30 aaa gga gcc acc tgg gat att ctc aac ctg gca gat gcg tta cta gag     144
Lys Gly Ala Thr Trp Asp Ile Leu Asn Leu Ala Asp Ala Leu Leu Glu
         35                  40                  45 cag gcc atg att gga cca tcc ccc aat cct ctc atc ttg tcc tac ctg     192
Gln Ala Met Ile Gly Pro Ser Pro Asn Pro Leu Ile Leu Ser Tyr Leu
     50                  55                  60 aag tat gcc att agt tcc cag atg gtg tcc tac tct tct gtc ctc aca     240
Lys Tyr Ala Ile Ser Ser Gln Met Val Ser Tyr Ser Ser Val Leu Thr
 65                  70                  75                  80 gcc atc agt aag ttt gat gac ttt tct cgg gac ctg tgt gtc cag gca     288
Ala Ile Ser Lys Phe Asp Asp Phe Ser Arg Asp Leu Cys Val Gln Ala
                 85                  90                  95 ttg ctg gac atc atg gac atg ttt tgt gac cgt ctg agc tgt cac ggc     336
Leu Leu Asp Ile Met Asp Met Phe Cys Asp Arg Leu Ser Cys His Gly
            100                 105                 110 aaa gca gaa gaa tgc atc gga ctg tgc cga gcc ctt ctt agc gcc ctc     384
Lys Ala Glu Glu Cys Ile Gly Leu Cys Arg Ala Leu Leu Ser Ala Leu
        115                 120                 125 cac tgg ctg ctg cgc tgc acg gca gcc tct gca gaa cgg ctg cgg gaa     432
His Trp Leu Leu Arg Cys Thr Ala Ala Ser Ala Glu Arg Leu Arg Glu
```

```
                130               135               140
ggg ctg gaa gcc ggc act cca gcc gct ggg gag aag cag ctt gcc atg      480
Gly Leu Glu Ala Gly Thr Pro Ala Ala Gly Glu Lys Gln Leu Ala Met
145                 150               155               160 tgc ctt cag cgc ctg gag aaa acc ctc agc agc acc aag aac cgg gcc      528
Cys Leu Gln Arg Leu Glu Lys Thr Leu Ser Ser Thr Lys Asn Arg Ala
                165               170               175 ctg ctg cac atc gcc aaa cta gag gag gcc tct tct tgg act gcc atc      576
Leu Leu His Ile Ala Lys Leu Glu Glu Ala Ser Ser Trp Thr Ala Ile
            180               185               190 gag cat tct ctc ttg aaa ctt gga gag atc ctg gcc aat ctc agc aac      624
Glu His Ser Leu Leu Lys Leu Gly Glu Ile Leu Ala Asn Leu Ser Asn
        195               200               205 ccg cag ctc cgg agt cag gcc gag cag tgt ggc acc ctc att agg agc      672
Pro Gln Leu Arg Ser Gln Ala Glu Gln Cys Gly Thr Leu Ile Arg Ser
    210               215               220 atc ccc acg atg ctg tct gtg cat gcg gag cag atg cac aag acc ggc      720
Ile Pro Thr Met Leu Ser Val His Ala Glu Gln Met His Lys Thr Gly
225               230               235               240 ttc ccc act gtc cac gcc gtg atc ctg ctc gag ggc acc atg aac ctg      768
Phe Pro Thr Val His Ala Val Ile Leu Leu Glu Gly Thr Met Asn Leu
                245               250               255 aca ggc gag acg cag tcc ctg gtg gag cag ctg acg atg gtg aag cgc      816
Thr Gly Glu Thr Gln Ser Leu Val Glu Gln Leu Thr Met Val Lys Arg
            260               265               270 atg cag cat atc ccc acc cca ctt ttt gtc ctg gag atc tgg aaa gct      864
Met Gln His Ile Pro Thr Pro Leu Phe Val Leu Glu Ile Trp Lys Ala
        275               280               285 tgc ttc gtg ggg ctc att gag tct ccc gag ggt acg gag gag ctc aag      912
Cys Phe Val Gly Leu Ile Glu Ser Pro Glu Gly Thr Glu Glu Leu Lys
    290               295               300 tgg aca gct ttc act ttc ctc aag att cca cag gtt ttg gtg aag ttg      960
Trp Thr Ala Phe Thr Phe Leu Lys Ile Pro Gln Val Leu Val Lys Leu
305               310               315               320 aag aag tac tct cat gga gac aag gac ttc act gag gat gtc aac tgt     1008
Lys Lys Tyr Ser His Gly Asp Lys Asp Phe Thr Glu Asp Val Asn Cys
                325               330               335 gct ttt gag ttc ctg ctg aag ctc acc ccc ttg ttg gac aaa gct gac     1056
Ala Phe Glu Phe Leu Leu Lys Leu Thr Pro Leu Leu Asp Lys Ala Asp
            340               345               350 cag cgc tgc aac tgt gac tgt aca aac ttc ctc ctc caa gaa tgt ggc     1104
Gln Arg Cys Asn Cys Asp Cys Thr Asn Phe Leu Leu Gln Glu Cys Gly
        355               360               365 aag cag ggg ctt ctg tct gag gcc agc gtc aac aac ctt atg gct aag     1152
Lys Gln Gly Leu Leu Ser Glu Ala Ser Val Asn Asn Leu Met Ala Lys
    370               375               380 cgc aaa gcg gac cga gag cac gca ccc cag cag aaa tcg gga gag aat     1200
Arg Lys Ala Asp Arg Glu His Ala Pro Gln Gln Lys Ser Gly Glu Asn
385               390               395               400 gcc aac atc cag ccc aac atc cag ctg atc ctc cgg gcg gag ccc act     1248
Ala Asn Ile Gln Pro Asn Ile Gln Leu Ile Leu Arg Ala Glu Pro Thr
                405               410               415 gtc aca aac atc ctc aag acg atg gat gca gac cac tct aag tca ccg     1296
Val Thr Asn Ile Leu Lys Thr Met Asp Ala Asp His Ser Lys Ser Pro
            420               425               430 gag gga ctg ctg gga gtc ctg ggc cac atg ctg tcc ggg aag agt ctg     1344
Glu Gly Leu Leu Gly Val Leu Gly His Met Leu Ser Gly Lys Ser Leu
        435               440               445 gac ttg ctg ctg gct gcc gcc gcc gcc act gga aag ctg aaa tcc ttc     1392
```

```
                                                                 -continued

Asp Leu Leu Leu Ala Ala Ala Ala Thr Gly Lys Leu Lys Ser Phe
    450                 455                 460 gcc cgg aaa ttc atc aat ttg aat gaa ttc aca acc tat ggc agc gaa    1440
Ala Arg Lys Phe Ile Asn Leu Asn Glu Phe Thr Thr Tyr Gly Ser Glu
465                 470                 475                 480 gaa agc acc aaa ccg gcc tcc gtc cgg gcc ctg ctg ttt gac atc tcc    1488
Glu Ser Thr Lys Pro Ala Ser Val Arg Ala Leu Leu Phe Asp Ile Ser
                485                 490                 495 ttc ctc atg ctg tgc cat gtg gcc cag acc tat ggt tca gag gtg att    1536
Phe Leu Met Leu Cys His Val Ala Gln Thr Tyr Gly Ser Glu Val Ile
            500                 505                 510 ctg tcc gag tcg cgc aca gga gct gag gtg ccc ttc ttc gag acc tgg    1584
Leu Ser Glu Ser Arg Thr Gly Ala Glu Val Pro Phe Phe Glu Thr Trp
        515                 520                 525 atg cag acc tgc atg cct gag gag ggc aag atc ctg aac cct gac cac    1632
Met Gln Thr Cys Met Pro Glu Glu Gly Lys Ile Leu Asn Pro Asp His
    530                 535                 540 ccc tgc ttc cgc ccc gac tcc acc aaa gtg gag tcc ctg gtg gcc ctg    1680
Pro Cys Phe Arg Pro Asp Ser Thr Lys Val Glu Ser Leu Val Ala Leu
545                 550                 555                 560 ctc aac aac tcc tcg gag atg aag cta gtg cag atg aag tgg cat gag    1728
Leu Asn Asn Ser Ser Glu Met Lys Leu Val Gln Met Lys Trp His Glu
                565                 570                 575 gcc tgt ctc agc atc tca gcc gcc atc ttg gaa atc ctc aat gcc tgg    1776
Ala Cys Leu Ser Ile Ser Ala Ala Ile Leu Glu Ile Leu Asn Ala Trp
            580                 585                 590 gag aat ggg gtc ctg gcc ttc gag tcc atc cag aaa atc act gat aac    1824
Glu Asn Gly Val Leu Ala Phe Glu Ser Ile Gln Lys Ile Thr Asp Asn
        595                 600                 605 atc aaa ggg aag gta tgc agt ctg gcg gtg tgt gct gtg gct tgg ctt    1872
Ile Lys Gly Lys Val Cys Ser Leu Ala Val Cys Ala Val Ala Trp Leu
    610                 615                 620 gtg gcc cac gtc cgg atg ctg ggg ctg gat gag cgt gag aag tcg ctg    1920
Val Ala His Val Arg Met Leu Gly Leu Asp Glu Arg Glu Lys Ser Leu
625                 630                 635                 640 cag atg atc cgc cag ctg gca ggg cca ctg ttt agt gag aac acc ctg    1968
Gln Met Ile Arg Gln Leu Ala Gly Pro Leu Phe Ser Glu Asn Thr Leu
                645                 650                 655 cag ttc tac aat gag agg gtg gtg atc atg aac tcg atc ctg gag cgc    2016
Gln Phe Tyr Asn Glu Arg Val Val Ile Met Asn Ser Ile Leu Glu Arg
            660                 665                 670 atg tgt gcc gac gtg ctg cag cag aca gcc acg cag atc aag ttt ccc    2064
Met Cys Ala Asp Val Leu Gln Gln Thr Ala Thr Gln Ile Lys Phe Pro
        675                 680                 685 tcc acc ggg gtg gac aca atg ccc tac tgg aac ctg ctg ccc ccc aag    2112
Ser Thr Gly Val Asp Thr Met Pro Tyr Trp Asn Leu Leu Pro Pro Lys
    690                 695                 700 cgg ccc atc aaa gag gtg ctg acg gac att ttt gcc aag gtg ctg gag    2160
Arg Pro Ile Lys Glu Val Leu Thr Asp Ile Phe Ala Lys Val Leu Glu
705                 710                 715                 720 aag ggc tgg gtg gac agc cgc tcc atc cac atc ttt gac acc ctg ctg    2208
Lys Gly Trp Val Asp Ser Arg Ser Ile His Ile Phe Asp Thr Leu Leu
                725                 730                 735 cac atg ggc ggc gtc tac tgg ttc tgc aac aac ctg att aag gag ctg    2256
His Met Gly Gly Val Tyr Trp Phe Cys Asn Asn Leu Ile Lys Glu Leu
            740                 745                 750 ctg aag gag acg cgg aag gag cac acg ctg cgg gca gtg gag ctg ctc    2304
Leu Lys Glu Thr Arg Lys Glu His Thr Leu Arg Ala Val Glu Leu Leu
        755                 760                 765
```

-continued

| | | |
|---|---|---|
| tac tcc atc ttc tgc ctg gac atg cag caa gtg acc ctg gtc ctg ctg<br>Tyr Ser Ile Phe Cys Leu Asp Met Gln Gln Val Thr Leu Val Leu Leu<br>770                                775                      780 | | 2352 |
| ggc cac atc cta cct ggc ctg ctc act gac tcc tcc aag tgg cac agc<br>Gly His Ile Leu Pro Gly Leu Leu Thr Asp Ser Ser Lys Trp His Ser<br>785                                790                            795                      800 | | 2400 |
| ctc atg gac ccc ccg ggc act gct ctt gcc aag ctg gcc gtg tgg tgt<br>Leu Met Asp Pro Pro Gly Thr Ala Leu Ala Lys Leu Ala Val Trp Cys<br>805                                810                            815 | | 2448 |
| gcc ctc agt tcc tac tcc tcc cac aag gga cag gcg tcc acc cgc cag<br>Ala Leu Ser Ser Tyr Ser Ser His Lys Gly Gln Ala Ser Thr Arg Gln<br>                  820                            825                      830 | | 2496 |
| aag aag aga cac cgc gaa gac att gag gat tat atc agc ctc ttc ccc<br>Lys Lys Arg His Arg Glu Asp Ile Glu Asp Tyr Ile Ser Leu Phe Pro<br>                        835                            840                      845 | | 2544 |
| ctg gac gat gtg cag cct tcg aag ttg atg cga ctg ctg agc tct aat<br>Leu Asp Asp Val Gln Pro Ser Lys Leu Met Arg Leu Leu Ser Ser Asn<br>850                                855                            860 | | 2592 |
| gag gac gat gcc aac atc ctt tcg agc ccc aca gac cga tcc atg agc<br>Glu Asp Asp Ala Asn Ile Leu Ser Ser Pro Thr Asp Arg Ser Met Ser<br>865                                870                            875                      880 | | 2640 |
| agc tcc ctc tca gcc tct cag ctc cac acg gtc aac atg cgg gac cct<br>Ser Ser Leu Ser Ala Ser Gln Leu His Thr Val Asn Met Arg Asp Pro<br>                  885                            890                      895 | | 2688 |
| ctg aac cga gtc ctg gcc aac ctg ttc ctg ctc atc tcc tcc atc ctg<br>Leu Asn Arg Val Leu Ala Asn Leu Phe Leu Leu Ile Ser Ser Ile Leu<br>900                                905                            910 | | 2736 |
| ggg tct cgc acc gct ggc ccc cac acc cag ttc gtg cag tgg ttc atg<br>Gly Ser Arg Thr Ala Gly Pro His Thr Gln Phe Val Gln Trp Phe Met<br>                  915                            920                      925 | | 2784 |
| gag gag tgt gtg gac tgc ctg gag cag ggt ggc cgt ggc agc gtc ctg<br>Glu Glu Cys Val Asp Cys Leu Glu Gln Gly Gly Arg Gly Ser Val Leu<br>930                                935                            940 | | 2832 |
| cag ttc atg ccc ttc acc acc gtg tcg gaa ctg gtg aag gtg tca gcc<br>Gln Phe Met Pro Phe Thr Thr Val Ser Glu Leu Val Lys Val Ser Ala<br>945                                950                            955                      960 | | 2880 |
| atg tcc agc ccc aag gtg gtt ctg gcc atc acg gac ctc agc ctg ccc<br>Met Ser Ser Pro Lys Val Val Leu Ala Ile Thr Asp Leu Ser Leu Pro<br>                  965                            970                      975 | | 2928 |
| ctg ggc cgc cag gtg gct gct aaa gcc att gct gca ctc tga<br>Leu Gly Arg Gln Val Ala Ala Lys Ala Ile Ala Ala Leu<br>980                                985                            990 | | 2970 |

<210> SEQ ID NO: 4
<211> LENGTH: 989
<212> TYPE: PRT
<213> ORGANISM: Homo sapiens

<400> SEQUENCE: 4

Met Lys Val Val Asn Leu Lys Gln Ala Ile Leu Gln Ala Trp Lys Glu
1                  5                       10                       15

Arg Trp Ser Asp Tyr Gln Trp Ala Ile Asn Met Lys Lys Phe Phe Pro
                  20                       25                       30

Lys Gly Ala Thr Trp Asp Ile Leu Asn Leu Ala Asp Ala Leu Leu Glu
              35                       40                       45

Gln Ala Met Ile Gly Pro Ser Pro Asn Pro Leu Ile Leu Ser Tyr Leu
      50                       55                       60

Lys Tyr Ala Ile Ser Ser Gln Met Val Ser Tyr Ser Ser Val Leu Thr
65                  70                       75                       80

-continued

```
Ala Ile Ser Lys Phe Asp Asp Phe Ser Arg Asp Leu Cys Val Gln Ala
             85                  90                  95

Leu Leu Asp Ile Met Asp Met Phe Cys Asp Arg Leu Ser Cys His Gly
            100                 105                 110

Lys Ala Glu Glu Cys Ile Gly Leu Cys Arg Ala Leu Leu Ser Ala Leu
            115                 120                 125

His Trp Leu Leu Arg Cys Thr Ala Ala Ser Ala Glu Arg Leu Arg Glu
130                 135                 140

Gly Leu Glu Ala Gly Thr Pro Ala Ala Gly Glu Lys Gln Leu Ala Met
145                 150                 155                 160

Cys Leu Gln Arg Leu Glu Lys Thr Leu Ser Ser Thr Lys Asn Arg Ala
                165                 170                 175

Leu Leu His Ile Ala Lys Leu Glu Glu Ala Ser Ser Trp Thr Ala Ile
            180                 185                 190

Glu His Ser Leu Leu Lys Leu Gly Glu Ile Leu Ala Asn Leu Ser Asn
            195                 200                 205

Pro Gln Leu Arg Ser Gln Ala Glu Gln Cys Gly Thr Leu Ile Arg Ser
            210                 215                 220

Ile Pro Thr Met Leu Ser Val His Ala Glu Gln Met His Lys Thr Gly
225                 230                 235                 240

Phe Pro Thr Val His Ala Val Ile Leu Leu Gly Thr Met Asn Leu
                245                 250                 255

Thr Gly Glu Thr Gln Ser Leu Val Glu Gln Leu Thr Met Val Lys Arg
            260                 265                 270

Met Gln His Ile Pro Thr Pro Leu Phe Val Leu Glu Ile Trp Lys Ala
            275                 280                 285

Cys Phe Val Gly Leu Ile Glu Ser Pro Glu Gly Thr Glu Glu Leu Lys
            290                 295                 300

Trp Thr Ala Phe Thr Phe Leu Lys Ile Pro Gln Val Leu Val Lys Leu
305                 310                 315                 320

Lys Lys Tyr Ser His Gly Asp Lys Asp Phe Thr Glu Asp Val Asn Cys
                325                 330                 335

Ala Phe Glu Phe Leu Leu Lys Leu Thr Pro Leu Leu Asp Lys Ala Asp
            340                 345                 350

Gln Arg Cys Asn Cys Asp Cys Thr Asn Phe Leu Leu Gln Glu Cys Gly
            355                 360                 365

Lys Gln Gly Leu Leu Ser Glu Ala Ser Val Asn Asn Leu Met Ala Lys
            370                 375                 380

Arg Lys Ala Asp Arg Glu His Ala Pro Gln Gln Lys Ser Gly Glu Asn
385                 390                 395                 400

Ala Asn Ile Gln Pro Asn Ile Gln Leu Ile Leu Arg Ala Glu Pro Thr
                405                 410                 415

Val Thr Asn Ile Leu Lys Thr Met Asp Ala Asp His Ser Lys Ser Pro
            420                 425                 430

Glu Gly Leu Leu Gly Val Leu Gly His Met Leu Ser Gly Lys Ser Leu
            435                 440                 445

Asp Leu Leu Leu Ala Ala Ala Ala Thr Gly Lys Leu Lys Ser Phe
            450                 455                 460

Ala Arg Lys Phe Ile Asn Leu Asn Glu Phe Thr Thr Tyr Gly Ser Glu
465                 470                 475                 480

Glu Ser Thr Lys Pro Ala Ser Val Arg Ala Leu Leu Phe Asp Ile Ser
                485                 490                 495

Phe Leu Met Leu Cys His Val Ala Gln Thr Tyr Gly Ser Glu Val Ile
```

-continued

```
                500                 505                 510
Leu Ser Glu Ser Arg Thr Gly Ala Glu Val Pro Phe Glu Thr Trp
            515                 520                 525

Met Gln Thr Cys Met Pro Glu Gly Lys Ile Leu Asn Pro Asp His
        530                 535                 540

Pro Cys Phe Arg Pro Asp Ser Thr Lys Val Glu Ser Leu Val Ala Leu
545                 550                 555                 560

Leu Asn Asn Ser Ser Glu Met Lys Leu Val Gln Met Lys Trp His Glu
                565                 570                 575

Ala Cys Leu Ser Ile Ser Ala Ala Ile Leu Glu Ile Leu Asn Ala Trp
                580                 585                 590

Glu Asn Gly Val Leu Ala Phe Glu Ser Ile Gln Lys Ile Thr Asp Asn
            595                 600                 605

Ile Lys Gly Lys Val Cys Ser Leu Ala Val Cys Ala Val Ala Trp Leu
        610                 615                 620

Val Ala His Val Arg Met Leu Gly Leu Asp Glu Arg Glu Lys Ser Leu
625                 630                 635                 640

Gln Met Ile Arg Gln Leu Ala Gly Pro Leu Phe Ser Glu Asn Thr Leu
                645                 650                 655

Gln Phe Tyr Asn Glu Arg Val Val Ile Met Asn Ser Ile Leu Glu Arg
                660                 665                 670

Met Cys Ala Asp Val Leu Gln Gln Thr Ala Thr Gln Ile Lys Phe Pro
            675                 680                 685

Ser Thr Gly Val Asp Thr Met Pro Tyr Trp Asn Leu Leu Pro Pro Lys
        690                 695                 700

Arg Pro Ile Lys Glu Val Leu Thr Asp Ile Phe Ala Lys Val Leu Glu
705                 710                 715                 720

Lys Gly Trp Val Asp Ser Arg Ser Ile His Ile Phe Asp Thr Leu Leu
                725                 730                 735

His Met Gly Gly Val Tyr Trp Phe Cys Asn Asn Leu Ile Lys Glu Leu
            740                 745                 750

Leu Lys Glu Thr Arg Lys Glu His Thr Leu Arg Ala Val Glu Leu Leu
        755                 760                 765

Tyr Ser Ile Phe Cys Leu Asp Met Gln Gln Val Thr Leu Val Leu Leu
        770                 775                 780

Gly His Ile Leu Pro Gly Leu Leu Thr Asp Ser Ser Lys Trp His Ser
785                 790                 795                 800

Leu Met Asp Pro Pro Gly Thr Ala Leu Ala Lys Leu Ala Val Trp Cys
                805                 810                 815

Ala Leu Ser Ser Tyr Ser Ser His Lys Gly Gln Ala Ser Thr Arg Gln
            820                 825                 830

Lys Lys Arg His Arg Glu Asp Ile Glu Asp Tyr Ile Ser Leu Phe Pro
        835                 840                 845

Leu Asp Asp Val Gln Pro Ser Lys Leu Met Arg Leu Leu Ser Ser Asn
850                 855                 860

Glu Asp Asp Ala Asn Ile Leu Ser Ser Pro Thr Asp Arg Ser Met Ser
865                 870                 875                 880

Ser Ser Leu Ser Ala Ser Gln Leu His Thr Val Asn Met Arg Asp Pro
                885                 890                 895

Leu Asn Arg Val Leu Ala Asn Leu Phe Leu Leu Ile Ser Ser Ile Leu
            900                 905                 910

Gly Ser Arg Thr Ala Gly Pro His Thr Gln Phe Val Gln Trp Phe Met
        915                 920                 925
```

```
Glu Glu Cys Val Asp Cys Leu Glu Gln Gly Gly Arg Gly Ser Val Leu
    930                 935                 940

Gln Phe Met Pro Phe Thr Thr Val Ser Glu Leu Val Lys Val Ser Ala
945                 950                 955                 960

Met Ser Ser Pro Lys Val Val Leu Ala Ile Thr Asp Leu Ser Leu Pro
                965                 970                 975

Leu Gly Arg Gln Val Ala Ala Lys Ala Ile Ala Ala Leu
            980                 985

<210> SEQ ID NO: 5
<211> LENGTH: 29
<212> TYPE: DNA
<213> ORGANISM: Artificial Sequence
<220> FEATURE:
<223> OTHER INFORMATION: Description of Artificial Sequence: Primer

<400> SEQUENCE: 5
gcggatcccc tcttatccta aatctgatc                                          29

<210> SEQ ID NO: 6
<211> LENGTH: 29
<212> TYPE: DNA
<213> ORGANISM: Artificial Sequence
<220> FEATURE:
<223> OTHER INFORMATION: Description of Artificial Sequence: Primer

<400> SEQUENCE: 6
ggaattcatc gggtggttct tggtgttgc                                          29

<210> SEQ ID NO: 7
<211> LENGTH: 32
<212> TYPE: DNA
<213> ORGANISM: Artificial Sequence
<220> FEATURE:
<223> OTHER INFORMATION: Description of Artificial Sequence: Primer

<400> SEQUENCE: 7
gatacgtcga cgatggccgg caacaccaag aa                                      32

<210> SEQ ID NO: 8
<211> LENGTH: 32
<212> TYPE: DNA
<213> ORGANISM: Artificial Sequence
<220> FEATURE:
<223> OTHER INFORMATION: Description of Artificial Sequence: Primer

<400> SEQUENCE: 8
gatgcagatc ttctggtgct ttggtttctc ag                                      32

<210> SEQ ID NO: 9
<211> LENGTH: 33
<212> TYPE: DNA
<213> ORGANISM: Artificial Sequence
<220> FEATURE:
<223> OTHER INFORMATION: Description of Artificial Sequence: Primer

<400> SEQUENCE: 9
catgccatgg atggggagga cttcagcaag gtg                                     33

<210> SEQ ID NO: 10
<211> LENGTH: 34
<212> TYPE: DNA
<213> ORGANISM: Artificial Sequence
<220> FEATURE:
```

<223> OTHER INFORMATION: Description of Artificial Sequence: Primer

<400> SEQUENCE: 10
gcggatcctc actggtgctt tggtttctca ggtg                                34

<210> SEQ ID NO: 11
<211> LENGTH: 32
<212> TYPE: DNA
<213> ORGANISM: Artificial Sequence
<220> FEATURE:
<223> OTHER INFORMATION: Description of Artificial Sequence: Primer

<400> SEQUENCE: 11
ggaattccat atggtggaca cggaaagccc ac                                  32

<210> SEQ ID NO: 12
<211> LENGTH: 30
<212> TYPE: DNA
<213> ORGANISM: Artificial Sequence
<220> FEATURE:
<223> OTHER INFORMATION: Description of Artificial Sequence: Primer

<400> SEQUENCE: 12
gcggatcctc agtacatgtc cctgtagatc                                     30

<210> SEQ ID NO: 13
<211> LENGTH: 30
<212> TYPE: DNA
<213> ORGANISM: Artificial Sequence
<220> FEATURE:
<223> OTHER INFORMATION: Description of Artificial Sequence: Primer

<400> SEQUENCE: 13
ggaattccat atggaggcaa tggcggccag                                     30

<210> SEQ ID NO: 14
<211> LENGTH: 30
<212> TYPE: DNA
<213> ORGANISM: Artificial Sequence
<220> FEATURE:
<223> OTHER INFORMATION: Description of Artificial Sequence: Primer

<400> SEQUENCE: 14
gcggatcctc aggagatctc attgccaaac                                     30

<210> SEQ ID NO: 15
<211> LENGTH: 38
<212> TYPE: DNA
<213> ORGANISM: Artificial Sequence
<220> FEATURE:
<223> OTHER INFORMATION: Description of Artificial Sequence: Primer

<400> SEQUENCE: 15
ggaattccat atgaagaaga acagcctggc cttgtccc                             38

<210> SEQ ID NO: 16
<211> LENGTH: 35
<212> TYPE: DNA
<213> ORGANISM: Artificial Sequence
<220> FEATURE:
<223> OTHER INFORMATION: Description of Artificial Sequence: Primer

<400> SEQUENCE: 16
cgggatcctc agactgtggc agggaaaccc tctgc                                35

```
<210> SEQ ID NO: 17
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 17
ctagccaggt cacagcaggt cagc                                              24

<210> SEQ ID NO: 18
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 18
tcgagctgac ctgctgtgac ctgg                                              24

<210> SEQ ID NO: 19
<211> LENGTH: 31
<212> TYPE: DNA
<213> ORGANISM: Artificial Sequence
<220> FEATURE:
<223> OTHER INFORMATION: Description of Artificial Sequence: Primer

<400> SEQUENCE: 19
gactactcga gtcgccccgg gtgttcctga a                                      31

<210> SEQ ID NO: 20
<211> LENGTH: 30
<212> TYPE: DNA
<213> ORGANISM: Artificial Sequence
<220> FEATURE:
<223> OTHER INFORMATION: Description of Artificial Sequence: Primer

<400> SEQUENCE: 20
atgcaagctt cggggatgaa gatgataggg                                        30

<210> SEQ ID NO: 21
<211> LENGTH: 31
<212> TYPE: DNA
<213> ORGANISM: Artificial Sequence
<220> FEATURE:
<223> OTHER INFORMATION: Description of Artificial Sequence: Primer

<400> SEQUENCE: 21
atgcaagctt atgagagtga atgatgatag a                                      31

<210> SEQ ID NO: 22
<211> LENGTH: 54
<212> TYPE: DNA
<213> ORGANISM: Artificial Sequence
<220> FEATURE:
<223> OTHER INFORMATION: Description of Artificial Sequence: Primer

<400> SEQUENCE: 22
ctagcgagct cgggtgaacg ggggcagagc tcgggtgaac gggggcagag ctcc             54

<210> SEQ ID NO: 23
<211> LENGTH: 55
<212> TYPE: DNA
<213> ORGANISM: Artificial Sequence
<220> FEATURE:
<223> OTHER INFORMATION: Description of Artificial Sequence: Primer
```

<400> SEQUENCE: 23
tcgagggagc tctgccccg ttcacccgag ctctgccccc gttcacccga gctcg       55

<210> SEQ ID NO: 24
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 24
cgggtgaacg ggggcagagc t                                           21

<210> SEQ ID NO: 25
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 25
ctgcccccgt tcacccgagc t                                           21

<210> SEQ ID NO: 26
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 26
ccaggtcaca gcaggtcagg agct                                        24

<210> SEQ ID NO: 27
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 27
cctgacctgc tgtgacctgg agct                                        24

<210> SEQ ID NO: 28
<211> LENGTH: 33
<212> TYPE: DNA
<213> ORGANISM: Artificial Sequence
<220> FEATURE:
<223> OTHER INFORMATION: Description of Artificial Sequence: Primer

<400> SEQUENCE: 28
gactacgtcg accctcatgg acccccgggg cac                              33

<210> SEQ ID NO: 29
<211> LENGTH: 29
<212> TYPE: DNA
<213> ORGANISM: Artificial Sequence
<220> FEATURE:
<223> OTHER INFORMATION: Description of Artificial Sequence: Primer

<400> SEQUENCE: 29
tgcggatccg tccaggggga agaggctga                                   29

<210> SEQ ID NO: 30
<211> LENGTH: 20

```
<212> TYPE: DNA
<213> ORGANISM: Artificial Sequence
<220> FEATURE:
<223> OTHER INFORMATION: Description of Artificial Sequence: Primer

<400> SEQUENCE: 30
gccagctggc agggccactg                                                    20

<210> SEQ ID NO: 31
<211> LENGTH: 19
<212> TYPE: DNA
<213> ORGANISM: Artificial Sequence
<220> FEATURE:
<223> OTHER INFORMATION: Description of Artificial Sequence: Primer

<400> SEQUENCE: 31
ctccgggcgg agccactgt                                                     19

<210> SEQ ID NO: 32
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 32
cctccactgg ctgctgcgct                                                    20

<210> SEQ ID NO: 33
<211> LENGTH: 33
<212> TYPE: DNA
<213> ORGANISM: Artificial Sequence
<220> FEATURE:
<223> OTHER INFORMATION: Description of Artificial Sequence: Primer

<400> SEQUENCE: 33
gactacgtcg accaccctgc tgcacatggg cgg                                     33

<210> SEQ ID NO: 34
<211> LENGTH: 30
<212> TYPE: DNA
<213> ORGANISM: Artificial Sequence
<220> FEATURE:
<223> OTHER INFORMATION: Description of Artificial Sequence: Primer

<400> SEQUENCE: 34
tgcggatccg ccgcccatgt gcagcagggt                                         30

<210> SEQ ID NO: 35
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 35
ctgaaatcct tcgcccggaa                                                    20

<210> SEQ ID NO: 36
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 36
```
ccactgcggc catgccaagc                                           20

<210> SEQ ID NO: 37
<211> LENGTH: 29
<212> TYPE: DNA
<213> ORGANISM: Artificial Sequence
<220> FEATURE:
<223> OTHER INFORMATION: Description of Artificial Sequence: Primer

<400> SEQUENCE: 37
tgcggatccg gccggtttgg tgctttctt                                 29

<210> SEQ ID NO: 38
<211> LENGTH: 33
<212> TYPE: DNA
<213> ORGANISM: Artificial Sequence
<220> FEATURE:
<223> OTHER INFORMATION: Description of Artificial Sequence: Primer

<400> SEQUENCE: 38
gactacgtcg accaagaccg gcttccccac tgt                            33

<210> SEQ ID NO: 39
<211> LENGTH: 29
<212> TYPE: DNA
<213> ORGANISM: Artificial Sequence
<220> FEATURE:
<223> OTHER INFORMATION: Description of Artificial Sequence: Primer

<400> SEQUENCE: 39
tgcggatccg gtgccctcga gcaggatca                                 29

<210> SEQ ID NO: 40
<211> LENGTH: 33
<212> TYPE: DNA
<213> ORGANISM: Artificial Sequence
<220> FEATURE:
<223> OTHER INFORMATION: Description of Artificial Sequence: Primer

<400> SEQUENCE: 40
gactacgtcg accatgaagg tggtcaacct gaa                            33

<210> SEQ ID NO: 41
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 41
caagaccggc ttccccactg                                           20

<210> SEQ ID NO: 42
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 42
gaggccggtt tggtgctttc                                           20

<210> SEQ ID NO: 43
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 43
ttgaatgaat tcacaaccta                                          20

<210> SEQ ID NO: 44
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 44
tcagagtgca gcaatggctt                                          20

<210> SEQ ID NO: 45
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 45
atggaaggtg gtcaacctga a                                        21

<210> SEQ ID NO: 46
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 46
gatcctgctc gagggcacca                                          20

<210> SEQ ID NO: 47
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 47
tggtgccctc gagcaggatc                                          20

<210> SEQ ID NO: 48
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 48
taggttgtga attcattcaa                                          20

<210> SEQ ID NO: 49
<211> LENGTH: 16
<212> TYPE: DNA
<213> ORGANISM: Artificial Sequence
<220> FEATURE:
<223> OTHER INFORMATION: Description of Artificial Sequence: DNA binding
      element or portion thereof.

<400> SEQUENCE: 49
aggtcacagc aggtca                                              16

```
<210> SEQ ID NO: 50
<211> LENGTH: 5
<212> TYPE: PRT
<213> ORGANISM: Homo sapiens
<220> FEATURE:
<223> OTHER INFORMATION: Motif-containing region of TRAP 220.
<220> FEATURE:
<221> NAME/KEY: NON_CONS
<222> LOCATION: (2)..(3)
<223> OTHER INFORMATION: They could be any amino acids.

<400> SEQUENCE: 50

Leu Xaa Xaa Leu Leu
 1               5

<210> SEQ ID NO: 51
<211> LENGTH: 5
<212> TYPE: PRT
<213> ORGANISM: Homo sapiens
<220> FEATURE:
<223> OTHER INFORMATION: Mutation of Sequence ID 50.
<220> FEATURE:
<221> NAME/KEY: NON_CONS
<222> LOCATION: ()..(3)
<223> OTHER INFORMATION: They could be any amino acids.

<400> SEQUENCE: 51

Leu Xaa Xaa Ala Ala
 1               5
```

US 6,248,520 B1

NUCLEIC ACID MOLECULES ENCODING NUCLEAR HORMONE RECEPTOR COACTIVATORS AND USES THEREOF

GOVERNMENTAL SUPPORT

The research leading to the present invention was supported, at least in part, by a grant from The National Institutes of Health, Grant No. CA42567. Accordingly, the Government may have certain rights in the invention.

FIELD OF THE INVENTION

The present invention relates to isolated nucleic acid molecules which encode nuclear hormone receptor coactivators, conserved variants thereof, fragments thereof, or analogs or derivatives thereof, which have applications in modulating the expression of genes in the nucleus.

BACKGROUND OF THE INVENTION

Nuclear hormone receptors are intracellular receptors that play important roles in expression of genes involved in physiological processes that include cell growth and differentiation, development, and homeostasis. Broadly, these receptors are members of a superfamily of receptors, whose members recognize similar DNA sequences that contain two or more hexanucleotide DNA-binding half-sites arranged as direct repeats or inverted repeats. It is through this recognition that these receptors are able to regulate the expression of genes in the nucleus, and thereby regulate cell differentiation, development and homeostasis. The thyroid hormone receptor (TRα) is an example of such a receptor. Upon activation, this receptor is involved in the expression of specific genes encoding energy-related enzymes, increasing their synthesis and consequently increasing the basal metabolic rate of the animal. [Lehninger et al. *Principles of Biochemistry*, 2d Edition. Worth Publishers, New York, 1993, p. 752]. The thyroid hormone receptor also plays an important role in development and maintenance of various brain and muscle tissues including but not restricted to neuronal development in neonate, neuronal cell migration, axonal growth and myelination in brain, and keeping body temperatures in muscles. Moreover, TRα is identical with protooncogene c-ErbA. The viral oncoprotein v-ErbA as well as some mutant TRα causes hepaocellular carcinoma.

Another example of a nuclear hormone receptor is the estrogen receptor. Upon binding with its corresponding hormone, estradiol, and its activation, this receptor plays a crucial role in regulating the development of the secondary sexual characteristics of females, and the controlled differentiation of cells involved in such development.

Still another example of a nuclear hormone receptor is the androgen receptor, which upon binding with testosterone, its corresponding hormone, and activation, is intimately involved in the development of secondary sexual characteristics of males, and cellular differentiation needed to produce such secondary characteristics. Still another nuclear hormone receptor comprises the peroxisome proliferator activated receptors (PPARs), and isoforms thereof. Upon binding with a peroxisome proliferator such as clofibric acid, nafenopin, or Wy-14,683, as well as by some fatty acids, and activation, this receptor induces expression of a number of genes, including those that encode coenzyme A oxidase and CYP45 0 A6. Furthermore, PPARγ2, an isoform of PPAR, is involved in the regulation of the differentiation fat cells. Also included in this superfamily of nuclear hormone receptors are the trans-retinoic acid receptor (RAR), the 9-cis retinoic acid receptor (RXR), the vitamin D receptor (VDR), and the progesterone receptor, which plays a critical role in forming and shedding of the endometrium during the menstrual cycle of a mature female.

These nuclear hormone receptors, upon activation, are able to regulation expression of genes because they directly bind to specific DNA sequences called hormone response elements, which are located either downstream or up stream from a gene whose transcription is regulated by the receptor. Upon the ligand dependent binding of the hormone to the receptor, the receptor changes its conformation in a manner that activates or suppresses the transcription of the gene to which it binds, and ultimately regulates biological processes such as cell growth, differentiation, and homeostasis.

In order for these receptors to regulate gene expression, they must be activated by ligands and bound to DNA. It has been determined that hormones that are generally small and hydrophobic, and are able diffuse across a plasma membrane and cytoplasm of a cell, bind to these receptors, and are involved in their activation. Examples of such hormones include, steroid hormones, such as testosterone, β-estradiol, aldosterone, cortisol and progesterone, thyroid hormones such as thyroxine ($T_4$) and triiodothyroxine ($T_3$) and vitamin D (in vertebrates) along with hormones derived therefrom. These hormones, also generally referred to as ligands, bind to nuclear hormone receptors, which is crucial to the activation of these of these receptors, their regulation of gene expression and ultimately their mediation of cell differentiation and development of an organism. The thyroid receptor also plays an important role in development and maintenance of various brain and muscle tissues.

However, in order for a specific hormone to bind to a specific nuclear hormone receptor such that the transcription of a particular gene is regulated, additional proteins forming a complex must also bind to the receptor. These proteins, referred to herein as coactivators, are required for functional interactions between the receptor and the gene whose transcription is regulated. One type of coactivator, a complex of thyroid hormone receptor-associated proteins (TRAPS) operates in conjunction with thyroid hormone to activate thyroid receptors. Together, the thyroid hormone receptor and the associated coactivator activate transcription by the general transcription machinery of the genes in the nucleus to which thyroid receptor binds. This activation involves interactions of the thyroid hormone receptor-coactivator complex with components of the general transcriptional machinery, itself comprised of RNA polymerase II, associated general initiation factors (TFIIA, TFIIB, TFIID, TFIIE, TFIIF and TFIIH), and general activators in the upstream stimulatory activity (USA). The coactivator function of the TRAPS was demonstrated in a cell free system reconstituted with purified DNA templates and components of the general transcription machinery, indicated that they act more directly to facilitate preinitiation complex formation on function [Fondell, J. D., Ge, H. & Roeder, R. G. (1996) *Proc. Natl. Acad. Sci. USA* 93, 8329–8333, which is hereby incorporated by reference herein in its entirety].

Hence, what is needed is isolation of TRAPS, including nucleic acid molecules which encode TRAPS, and the amino acid sequences of such TRAPS, so that numerous pharmaceuticals can be developed and assayed for their ability to regulate transcription of genes in vivo.

What is also needed are pharmaceutical compositions that can modulate the activation of nuclear hormone receptors, and thereby modulate expression of genes in an organism. Since nuclear hormone receptors play a vital role in mediating gene expression, cell growth and differentiation, development of an organism, and homeostasis, such modulation provides a valuable tool for treating numerous cancers, which involve uncontrolled differentiation, particularly in tissues comprising the sexual and reproductive organs, and in brain, muscle or adipocyte tissue.

What is also need are pharmaceutical compositions that can increase expression of genes that for some inexplicit able reason, are not sufficiently expression in vivo, resulting in a handicap deformity, or illness to the organism.

SUMMARY OF THE INVENTION

The present invention relates to isolated nucleic acid molecules which encode Thyroid Receptor-Associated Proteins (TRAPS), which are coactivators that are included in protein complexes, and bind to nuclear hormone receptors in a ligand (hormone)-dependent manner so that the receptor regulates the transcription of a particular gene. Examples of nuclear hormone receptors to which TRAPS of the invention bind include, but are not limited to, α and β isoforms of thyroid hormone receptor (TR), having thyroid hormone as corresponding particular hormone, vitamin D receptor (VDR) having vitamin D as a corresponding hormone, isoforms α, β, and γ of retinoic acid receptor having trans-retinoic acid or 9-cis retinoic acid as a corresponding hormone, α, β, and γ isoforms of retinoid X receptor (RXR), having retinoids (compounds related to retinoate, the carboxylate form of vitamin $A_1$) as a corresponding hormone, α and β isoforms of estrogen receptor (ER), having estradiol or estriol as a corresponding hormone, progesterone receptor having progesterone as a corresponding hormone, androgen receptor having testosterone as a corresponding hormone, glucocorticoid receptor having cortisol as a corresponding hormone, mineralcorticoid receptor (MR) having aldosterone as a corresponding hormone, and α and γ isoforms of peroxisome proliferation-activated receptor (PPAR) having respectively Wy14643 and 15-deoxy-$D^{12,14}$-prostaglandin J2 as corresponding hormones.

Thus, the present invention extends to an isolated nucleic acid molecule which encodes a nuclear hormone receptor coactivator, conserved variants thereof, fragments thereof, or analogs or derivatives thereof, wherein the isolated nucleic acid molecule comprises a DNA sequence of FIG. 1 (SEQ ID NO:1), degenerate variants thereof, fragments thereof, or analogs or derivatives thereof.

Furthermore, the present invention extends to an isolated nucleic acid molecule which encodes a nuclear hormone receptor coactivator, conserved variants thereof, fragments thereof, or analogs or derivatives thereof, wherein the isolated nucleic acid molecule comprises a DNA sequence of FIG. 1 (SEQ ID NO:1), degenerate variants thereof, fragments thereof, or analogs or derivatives thereof, and is detectably labeled. Numerous detectable labels have applications in the present invention. Examples of such detectable labels include, but are not limited to a radioactive element, a chemical which fluoresces, or an enzyme.

Moreover, the present invention extends to an isolated nucleic acid molecule hybridizable under standard hybridization conditions to an isolated nucleic acid molecule comprising a DNA sequence of FIG. 1 (SEQ ID NO:1), degenerate variants thereof, fragments thereof, or analogs or derivatives thereof.

The present invention further extends to a detectably labeled isolated nucleic acid molecule hybridizable under standard hybridization conditions to an isolated nucleic acid comprising a DNA sequence of FIG. 1 (SEQ ID NO:1), degenerate variants thereof, fragments thereof, or analogs or derivatives thereof. As explained above, numerous detectable labels have applications in the present invention, including radioactive elements, chemicals which fluoresce, or an enzyme, to name only a few.

In addition, the present invention extends to an isolated nucleic acid which encodes a nuclear hormone receptor coactivator, conserved variants thereof, fragments thereof, or analogs or derivatives thereof, wherein the isolated nucleic acid molecule comprises a DNA sequence of FIG. 1 (SEQ ID NO:1), degenerate variants thereof, fragments thereof, or analogs or derivatives thereof, and the nuclear hormone receptor coactivator is TRAP 220, comprising an amino acid sequence of FIG. 2 (SEQ ID NO:2), conserved variants thereof, fragments thereof, or analogs or derivatives thereof.

Moreover, the present invention extends to an isolated nucleic acid molecule hybridizable under standard hybridization conditions to an isolated nucleic acid molecule comprising a DNA sequence of FIG. 1 (SEQ ID NO:1), degenerate variants thereof, fragments thereof, or analogs or derivatives thereof.

Naturally, the present invention extends to an isolated and homogenous nuclear hormone receptor coactivator, conserved variants thereof, fragments thereof, or analogs or erivatives thereof, wherein the isolated, homogenous coactivator comprises an amino acid sequence of FIG. 2 (SEQ ID NO:2), conserved variants thereof, fragments thereof, or analogs or derivatives thereof.

Furthermore, the present invention extends to antibodies having as an immunogen an isolated homogenous nuclear hormone receptor coactivator, conserved variants thereof, fragments thereof, or analogs or derivatives thereof, wherein the isolated homogeneous nuclear hormone receptor coactivator comprises an amino acid sequence of FIG. 2 (SEQ ID NO:2). conserved variants thereof, fragments thereof, or analogs or derivatives thereof. As a result, the present invention extends to antibodies having TRAP 220, conserved variants thereof, fragments thereof, or analogs or derivatives thereof, as an immunogen. Antibodies of the present invention can be monoclonal or polyclonal. Moreover, the present invention extends to antibodies which are "chimeric" in that they may comprise protein domains from anti-TRAP220 antibodies raised against TRAP220, conserved variants thereof, fragments thereof, or analogs or derivatives thereof, in different species.

In addition, the present invention an antibody having TRAP220, conserved variants thereof, fragments thereof, or analogs or derivatives thereof, as an immunogen, wherein the antibody is detectably labeled, so that its bonding to TRAP220, conserved variants thereof, fragments thereof, or analogs or derivatives thereof can be detected. Detectable labels having applications in an antibody of the present invention include enzymes, radioactive isotopes, or chemicals which fluoresce.

In another embodiment, the present invention extends to an isolated nucleic acid molecule which encodes a nuclear hormone receptor coactivator, conserved variants thereof, fragments thereof, or analogs or derivatives thereof, wherein the isolated nucleic acid molecule comprises a DNA sequence of FIG. 3 (SEQ ID NO:3), degenerate variants thereof, fragments thereof, or analogs or derivatives thereof.

Furthermore, the present invention extends to an isolated nucleic acid molecule which encodes a nuclear hormone receptor coactivator, conserved variants thereof, fragments thereof, or analogs or derivatives thereof, wherein the isolated nucleic acid molecule comprises a DNA sequence of FIG. 3 (SEQ ID NO:3), degenerate variants thereof, fragments thereof, or analogs or derivatives thereof, and is detectably labeled. Numerous detectable labels have applications in the present invention. Examples of such detectable labels include, but are not limited to a radioactive element, a chemical which fluoresces, or an enzyme.

Moreover, the present invention extends to an isolated nucleic acid molecule hybridizable under standard hybridization conditions to an isolated nucleic acid molecule comprising a DNA sequence of FIG. 3 (SEQ ID NO:3), degenerate variants thereof, fragments thereof, or analogs or derivatives thereof.

The present invention further extends to an isolated nucleic acid molecule hybridizable under standard hybridization conditions to an isolated nucleic acid molecule comprising a DNA sequence of FIG. 3 (SEQ ID NO:3), degenerate variants thereof, fragments thereof, or analogs or derivatives thereof, detectably labeled. As explained above, numerous detectable labels have applications in the present invention, including radioactive elements, chemicals which fluoresce, or an enzyme, to name only a few.

In addition, the present invention extends to an isolated nucleic acid which encodes a nuclear hormone receptor coactivator, conserved variants thereof, fragments thereof, or analogs or derivatives thereof, wherein the isolated nucleic acid molecule comprises a DNA sequence of FIG. 3 (SEQ ID NO:3), degenerate variants thereof, fragments thereof, or analogs or derivatives thereof, and the nuclear hormone receptor coactivator comprises an amino acid sequence of FIG. 4 (SEQ ID NO:4), conserved variants thereof, fragments thereof, or analogs or derivatives thereof.

Naturally, the present invention extends to an isolated and homogenous nuclear hormone receptor coactivator comprising an amino acid sequence of FIG. 4 (SEQ ID NO:4), conserved variants thereof, fragments thereof, or analogs or derivatives thereof.

Furthermore, the present invention to antibodies having as an immunogen an isolated homogenous nuclear receptor coactivator, conserved variants thereof, fragments thereof, or analogs or derivatives thereof, wherein the isolated homogeneous nuclear hormone receptor coactivator comprises an amino acid sequence of FIG. 4 (SEQ ID NO:4), conserved variants thereof, fragments thereof, or analogs or derivatives thereof. As a result, the present invention extends to antibodies having TRAP 100, conserved variants thereof, fragments thereof, or analogs or derivatives thereof, as an immunogen. Antibodies of the present invention can be monoclonal or polyclonal. Moreover, the present invention extends to antibodies which are "chimeric" in that they may comprise protein domains from anti-TRAP100 antibodies raised against TRAP100, conserved variants thereof, fragments thereof, or analogs or derivatives thereof, in different species.

Moreover, the present invention extends to an antibody having TRAP100, conserved variants thereof, fragments thereof, or analogs or derivatives thereof, as an immunogen, wherein the antibody is detectably labeled so that its binding to TRAP100, conserved variants thereof, fragments thereof, or analogs or derivatives thereof can be detected. Detectable labels having applications in an antibody of the present invention comprise enzymes, radioactive isotopes, or chemicals which fluoresce.

Furthermore, the present invention extends to a cloning vector comprising an isolated nucleic acid molecule of the invention comprising a DNA sequence of FIG. 1 (SEQ ID NO:1), degenerate variants thereof, fragments thereof, or analogs or derivatives thereof, and an origin of replication. Alternatively, a cloning vector of the invention may comprise an isolated nucleic acid molecule hybridizable under standard hybridization conditions to an isolated nucleic acid molecule comprising a DNA sequence of FIG. 1 (SEQ ID NO:1), degenerate variants thereof, fragments thereof, or analogs or derivatives thereof, and an origin of replication.

Moreover, the present invention also extends to a cloning vector comprising an isolated nucleic acid molecule comprising a DNA sequence of FIG. 3 (SEQ ID NO:3), degenerate variants thereof, fragments thereof, or analogs or derivatives thereof, and an origin of replication. Alternatively, a cloning vector of the invention may comprise an isolated nucleic acid molecule hybridizable under standard hybridization conditions to an isolated nucleic acid molecule comprising a DNA sequence of FIG. 3 (SEQ ID NO:3), degenerate variants thereof, fragments thereof, or analogs or derivatives thereof, and an origin of replication.

Numerous cloning vectors have applications in the instant invention for cloning isolated nucleic acid molecules of the invention. Examples of such cloning vectors include, but are not limited to *E. coli*, bacteriophages such as lambda derivatives, plasmids such as pBR322 derivatives, and pUC plasmid derivatives such as pGEX vectors, pmal-c or pFLAG.

Furthermore, the present invention extends to a unicellular host transformed or transfected with a cloning vector of the invention. Examples of unicellular hosts having applications in the present invention include, but are not limited to *E. coli*, Pseudonomas, Bacillus, Strepomyces, yeast, CHO, R1.1, B-W, L-M, COS1, COS7, BSC1, BSC40, BMT10, Sf9, and NIH 3T3 cells, to name only a few.

The present invention further extends to an expression vector comprising an isolated nucleic acid molecule comprising a DNA sequence of FIG. 1 (SEQ ID NO:1), degenerate variants thereof, fragments thereof, or analogs or derivatives thereof, operatively associated with a promoter.

Naturally, the present invention extends to an expression vector comprising an isolated nucleic acid molecule hybridizable under standard hybridization conditions to an isolated nucleic acid molecule comprising a DNA sequence of FIG. 1 (SEQ ID NO:1), degenerate variants thereof, fragments thereof, or analogs or derivatives thereof, operatively associated with a promoter.

Furthermore, the present invention extends to an expression vector comprising an isolated nucleic acid comprising a DNA sequence of FIG. 3 (SEQ ID NO:3), degenerate variants thereof, fragments thereof, or analogs or derivatives thereof, operatively associated with a promoter.

In addition, the present invention extends to an expression vector comprising an isolated nucleic acid hybridizable under standard hybridization conditions to an isolated nucleic acid molecule comprising a DNA sequence of FIG. 3 (SEQ ID NO:3), degenerate variants thereof, fragments thereof, or analogs or derivatives thereof, operatively associated with a promoter.

An expression vector of the present invention can employ numerous promoters to express an isolated nucleic acid molecule of the invention. Examples of promoters having applications herein include early promoters of hCMV, early promoters of SV40, early promoters of adenovirus, early promoters of vaccinia, early promoters of polyoma, late promoters of SV40, late promoters of adenovirus, late promoters of vaccinia, late promoters of polyoma, the lac the trp system, the TAC system, the TRC system, the major operator and promoter regions of phage lambda, control regions of fd coat protein, 3-phosphoglycerate kinase promoter, acid phosphatase promoter, or promoters of yeast α mating factor, to name only a few.

In addition, the present invention extends to a unicellular host transformed or transfected with an expression vector of the invention. Numerous types of unicellular hosts, have applications in the present invention. Examples include *E. coli.* Pseudonomas, Bacillus, Strepomyces, yeast, CHO, R1.1, B-W, L-M, COS1, COS7, BSC1, BSC40, BMT10, Sf9, and NIH 3T3 cells, to name only a few. Moreover, mammalian cells can be used as a unicellular host.

Naturally, the present invention extends to a method for producing an isolated and homogenous nuclear hormone receptor coactivator comprising an amino acid sequence of FIG. 2 (SEQ ID NO:2), conserved variants thereof, fragments thereof or analogs or derivatives thereof, Such a method of the invention comprises the steps of culturing unicellular host transformed or transfected with expression vector comprising an isolated nucleic acid molecule comprising a DNA sequence of FIG. 1 (SEQ ID NO:1), degenerate variants thereof, fragments thereof, or analogs or derivatives thereof, operatively associated with a promoter, under conditions that provide for expression of the isolated nucleic acid molecule, and recovering the nuclear hormone receptor coactivator, conserved variants thereof, fragments thereof, or analogs or derivatives thereof, from the unicellular host, the culture medium, or both.

An alternate method for producing an isolated and homogeneous nuclear hormone receptor coactivator comprising an amino acid sequence of FIG. 2 (SEQ ID NO:2), conserved variants thereof, fragments thereof, or analogs or derivatives thereof, comprises the steps of culturing a unicellular host transformed or transfected with an expression vector comprising an isolated nucleic acid molecule which is hybridizable under standard hybridization conditions to an isolated nucleic acid molecule comprising a DNA sequence of FIG. 1 (SEQ ID NO:1), degenerate variants thereof, fragments thereof, or analogs or derivatives thereof, and is operatively associated with a promoter, under conditions that provide for expression of the isolated nucleic acid molecule, and recovering the nuclear hormone receptor coactivator from the unicellular host, the culture medium, or both.

In another embodiment, the present invention extends to a method for producing an isolated and homogenous nuclear hormone receptor coactivator, conserved variants thereof, fragments thereof, or analogs or derivatives thereof, comprising an amino acid sequence of FIG. 4 (SEQ ID NO:4), conserved variants thereof, fragments thereof, or analogs or derivatives thereof. Such a method comprises the steps of culturing a unicellular host transformed or transfected with an expression vector comprising an isolated nucleic acid molecule comprising a DNA sequence of FIG. 3 (SEQ ID NO:3), degenerate variants thereof, fragments thereof, or analogs or derivatives thereof, operatively associated with a promoter, under conditions that provide for expression of the isolated nucleic acid molecule, and collecting the isolated and homogenous nuclear hormone receptor coactivator from the unicellular host, the culture medium, or both.

Alternatively, a method for producing an isolated and homogeneous regulatory coactivator comprising an amino acid sequence of FIG. 4 (SEQ ID NO:4), conserved variants thereof, fragments thereof, or analogs or derivatives thereof, comprises the steps of culturing a unicellular host transformed or transfected with an expression vector comprising an isolated nucleic acid molecule hybridizable under standard hybridization conditions to an isolated nucleic acid molecule comprising a DNA sequence of FIG. 3 (SEQ ID NO:3), degenerate variants thereof, fragments thereof, or analogs or derivatives thereof, under conditions that provide for expression of the isolated nucleic acid molecule, and recovering the nuclear hormone receptor coactivator from the unicellular host, the culture medium, or both.

Furthermore, the present invention extends to a pharmaceutical composition for modulating the activity of nuclear hormone receptors. As explained above, a complex comprising TRAPs binds to a nuclear hormone receptor in a ligand dependent manner. The resulting receptor-coactivator complex, when bound to hormone response elements of a particular gene, modulates the expression of the particular gene. Consequently, the present invention extends to a pharmaceutical composition for modulating gene expression, comprising a nuclear hormone receptor coactivator, conserved variants thereof, fragments thereof or analogs or derivatives thereof, and a pharmaceutically acceptable carrier. Examples of nuclear hormone receptor coactivators having applications in a pharmaceutical composition of the invention comprise an amino acid sequence of FIG. 2 (SEQ ID NO:2), conserved variants thereof, fragments thereof, or analogs or derivatives thereof, or an amino acid sequence of FIG. 4 (SEQ ID NO:4), conserved variants thereof, fragments thereof, or analogs or derivatives thereof, and their associated proteins. Such a pharmaceutical composition may increase the function of nuclear hormone receptors, which would modulate gene expression relative to gene expression in a standard that did not receive the pharmaceutical composition. Alternatively, such a composition of the invention may interfere with the binding of a coactivator to the nuclear hormone receptor, which also modulates expression of the specific gene.

The present invention further extends to a method for modulating the activity of a nuclear receptor in vivo, and consequently modulating gene expression. Such a method comprises administering a therapeutically effective amount of a pharmaceutical composition comprising a nuclear hormone receptor coactivator, conserved variants thereof, fragments thereof, analogs or derivatives thereof, and a pharmaceutically acceptable carrier thereof, such that levels of the coactivator, conserved variants thereof, fragments thereof, or analogs or derivatives thereof, are sufficient to modulate the function of a nuclear hormone receptor, i.e., decrease or increase the function of a nuclear hormone receptor. As a result, expression of the gene is modulated relative to expression of the gene in a standard, i.e. either increased or decreased relative to expression of the gene in a standard, depending upon whether the nuclear hormone receptor normally functions to increase or suppress expression of a particular gene.

Alternatively, the present invention further extends to a method for modulating the activity of a nuclear hormone receptor, comprising administering a pharmaceutical composition comprising a coactivator, conserved variants thereof, fragments thereof, or analogs or derivatives thereof, in an amount such that the coactivator, conserved variants thereof, fragments thereof, or analogs or derivatives thereof of the pharmaceutical composition binds to the nuclear hormone receptor and prevents endogenous TRAP complexes, or distinct nuclear hormone receptor-binding coactivators of the cell from binding to the receptor. Consequently, the function of the receptor is decreased relative to a standard, which modulates expression of the gene.

Examples of coactivators having applications in such methods of the invention include coactivators comprising an amino acid sequence of FIG. 2 (SEQ ID NO:2), conserved variants thereof, fragments thereof, or analogs or derivatives thereof, or an amino acid sequence of FIG. 4 (SEQ ID NO:4), conserved variants thereof, fragments thereof, or analogs or derivatives thereof.

Furthermore, the present invention extends to an assay system for screening potential drugs and other agents for ability to mimic or antagonize the function of corresponding hormones. Such a system comprises:

a) culturing an observable cellular test colony incubated with the potential drug or agent, wherein the cells of the cellular test colony contain a nuclear hormone receptor coactivator, conserved variants thereof, fragments thereof, or analogs or derivatives thereof, and a nuclear hormone receptor, which modulates the expression of a specific gene;

b) harvesting a cellular extract from the cellular test colony; and c) examining the extract to determine whether the expression of the gene was modulated relative to a standard, wherein such modulation is indicative of the ability of the potential drug or agent to mimic or antagonize the function of the corresponding hormone that binds to the nuclear hormone receptor.

In particular, if the nuclear hormone receptor and its corresponding hormone function to increase expression of the gene, and incubation of the potential drug or therapeutic agent along with the corresponding hormone results in decreased expression of the gene relative to expression in a standard, the potential drug or agent may be considered an antagonist of the corresponding hormone. In contrast, if incubation of the potential drug with the receptor in the absence of the corresponding hormone increases expression of the gene, the potential drug or agent may have applications as a mimic of the corresponding hormone.

Likewise, if the nuclear hormone receptor and its corresponding hormone function to repress expression of the gene, and incubation with the potential drug or therapeutic agent along with the hormone results in expression of the gene, the potential drug or agent may be considered an antagonist of the corresponding hormone. In contrast, if incubation with the potential drug in the absence of the corresponding hormone results in repression of expression the gene, the potential drug or agent may have applications as a mimic of the corresponding hormone.

In addition, the present invention extends to a cell free assay system, comprising incubating purified nuclear hormone receptor, purified coactivator, such as TRAP220, a corresponding hormone of the nuclear hormone receptor, and a potential drug or agent having the ability to mimic or antagonize the hormone. Such a method comprises the steps of incubating the purified nuclear receptor hormone with the coactivator, the corresponding hormone, and the potential drug or agent, and then determining whether the potential drug or agent and the coactivator have bound to receptor. If the drug or agent has bound to receptor, it is indicative that the potential drug or agent has a greater binding affinity for the receptor than does the hormone, and has applications as a potential mimic or antagonist of the hormone.

Examples of coactivators having applications in an assay system of the present invention include, TRAP220 comprising an amino acid sequence of FIG. 2 (SEQ ID NO:2), conserved variants thereof, fragments thereof, or analogs or derivatives thereof, or TRAP100, comprising an amino acid sequence of FIG. 4 (SEQ ID NO:4), conserved variants thereof, fragments thereof, or analogs or derivatives thereof.

Furthermore, examples of nuclear hormone receptors and their corresponding hormones that have applications in an assay system for screening potential drugs and other agents for ability mimic or antagonize the function of a corresponding hormones include, but are not limited to α and β isoforms of thyroid hormone receptor (TR), having thyroid hormone as a corresponding hormone, vitamin D receptor (VDR) having vitamin D as a corresponding hormone, isoforms α, β, and γ of retinoic acid receptor having trans-retinoic acid or 9-cis retinoic acid as a corresponding hormone, α, β, and γ isoforms of retinoid X receptor (RXR), having retinoids (compounds related to retinoate, the carboxylate form of vitamin $A_1$) as a corresponding hormone, α and β isoforms of estrogen receptor (ER), having estradiol or estriol as a corresponding hormone, progesterone receptor having progesterone as a corresponding hormone, androgen receptor having testosterone as a corresponding hormone, glucocorticoid receptor having cortisol as a corresponding hormone, mineralcorticoid receptor (MR) having aldosterone as a corresponding hormone, and α and γ isoforms of peroxisome proliferation-activated receptor (PPAR) having respectively Wy14643 and 15-deoxy-$D^{12,14}$-prostaglandin J2 as corresponding hormones.

In addition, the present invention extends to an assay system for screening drugs and other agents for ability to mimic or antagonize the function of hormones as explained above, wherein the potential drug or agent is a member of a library of compounds. Examples of libraries having applications in the present invention include, but are not limited to, a mixture of compounds, or a combinatorial library of compounds. Furthermore, examples of combinatorial compounds having applications in the present invention include, but are not limited to, a phage display library, or a synthetic peptide library, to name only a few.

In another embodiment, the present invention extends to a method for determining ligands that bind to a nuclear hormone receptor coactivator, conserved variants thereof, fragments thereof, or analogs or derivatives thereof. Such a method comprises the steps of culturing a suspected ligand with a nuclear hormone receptor coactivator, conserved variants thereof, fragments thereof, or analogs or derivatives thereof, removing the nuclear hormone receptor coactivator from the culture, and then determining whether the suspected ligand is bound to the nuclear hormone receptor coactivator. To a skilled artisan, many equivalent protocols are available for performing this method of the invention. For example, a nuclear hormone receptor coactivator, conserved variants thereof, fragments thereof or analogs or derivatives thereof can be immobilized onto a membrane, such as Polyvinylidenedifluoride (PVDF) or nitrocellulose. The membrane can then be cultured with the potential ligand, and then probed with a detectably labeled material which specifically binds to the ligand, such as an antibody having the ligand as an immunogen. In another example, the nuclear hormone receptor coactivator of the invention is immobilized onto beads, which are then placed into a column. A composition comprising a suspected ligand is then passed through the column so that the suspected ligand can contact the nuclear hormone receptor coactivator. The nuclear hormone receptor coactivator can then be removed from the bead, and assayed to determine whether the suspected ligand is bound thereto. Numerous other procedures that are well understood by the skilled artisan having applications in determining a ligand of a coactivator, and are encompassed by the present invention.

In addition, ligands of coactivators of the invention have applications as drugs or agents that modulate the binding of endogenous coactivator complexes to nuclear hormone receptors, and hence ultimately modulate expression of genes. In particular, some of the ligands bind a coactivator in a manner that prevents the binding of a complex comprising the coactivator from binding to a particular nuclear hormone receptor. Consequently, the function of the receptor is interrupted, resulting in a modulation of the expression of the specific gene relative to expression of the gene in a standard. Alternatively, some of the ligands bind to the coactivator in manner that increases the affinity of the complex for a nuclear hormone receptor. As a result, the function of the receptor is increased relative to function of the receptor in a standard, and modulates the expression of a specific gene. Consequently, the present invention extends to a pharmaceutical composition for modulating gene expression comprising a ligand of a nuclear receptor coactivator comprising an amino acid sequence of FIG. 2 (SEQ ID NO:2). conserved variants thereof, fragments thereof, or analogs or derivatives thereof, or an amino acid sequence of FIG. 4 (SEQ ID NO:4), conserved variants thereof, fragments thereof, or analogs or derivatives thereof, and a pharmaceutically acceptable carrier thereof.

In yet another embodiment, the present invention extends to the use of ligands of a coactivator of the invention for use in preventing the formation of a coactivator complex. As explained above, a coactivator complex comprising numerous coactivator proteins, binds to a receptor, and is involved in activating the receptor, and hence regulating expression of a particular gene. Consequently, if the formation of this complex is prevented, the receptor is not activated, and the expression of the gene can be modulated. Such prevention of the complex can involve a ligand binding to a nuclear hormone receptor coactivator, conserved variants thereof, fragments thereof, or analogs or derivatives thereof, in a manner that binds to the coactivator, and interrupts its binding to other coactivators of the complex. Hence, the present invention extends to a pharmaceutical composition comprising a ligand of a nuclear hormone receptor coactivator and a pharmaceutically acceptable carrier thereof.

Furthermore, the present invention extends to a method of modulating the function of a nuclear hormone receptor, comprising administering a therapeutically effective amount of a pharmaceutical composition comprising a ligand of a nuclear hormone receptor coactivator, conserved variants thereof, fragments thereof, or analogs or derivatives thereof, and a pharmaceutically acceptable carrier thereof.

Examples of nuclear hormone receptors whose function can be modulated with a pharmaceutical composition comprising a ligand of a nuclear hormone receptor coactivator and a pharmaceutically acceptable carrier thereof include, but are not limited to α and β isoforms of thyroid hormone receptor (TR), vitamin D receptor (VDR), isoforms α, β, and γ of retinoic acid receptor (RAR), α, β, and γ isoforms of retinoid X receptor (RXR), α and β isoforms of estrogen receptor (ER), progesterone receptor (PR), androgen receptor (AR), glucocorticoid receptor (GO), mineralcorticoid receptor (MR), and α and γ isoforms of peroxisome proliferation-activated receptor (PPAR).

Moreover, the invention extends to a method for screening drugs and other agents for ability to mimic or antagonize the function of a nuclear hormone receptor coactivator of the invention. Such a system comprises:

a) culturing an observable cellular test colony incubated with the potential drug or agent, wherein the cells of the cellular test colony contain a nuclear hormone receptor which can modulate the expression of a specific gene, and a corresponding hormone which binds to the nuclear hormone receptor;

b) harvesting a cellular extract from the cellular test colony; and c) examining the extract to determine whether the expression of the specific gene was modulated relative to expression of the specific gene in a standard, wherein the modulation of expression of the specific gene is indicative of the ability of the drug or agent to mimic or antagonize the nuclear hormone receptor coactivator.

More specifically, if the nuclear hormone receptor, corresponding hormone, and coactivator function to increase expression of the gene, and incubation of the potential drug or therapeutic agent with the nuclear hormone receptor, its corresponding hormone, and coactivator results in decreased expression of the gene relative to expression in a standard, and the effects are unrelated to effects on corresponding hormone-receptor interactions, the potential drug or agent may be considered an antagonist of the nuclear hormone receptor coactivator. In contrast, if incubation of the potential drug or agent with the nuclear hormone receptor, and its corresponding hormone in the absence of coactivator results in increased levels of expression of the gene relative to a standard, the potential drug or agent may have applications as a mimic of the nuclear hormone receptor coactivator.

Likewise, if the nuclear hormone receptor, corresponding hormone, and coactivator function to repress expression of the gene, and incubation with the potential drug or therapeutic agent with the nuclear hormone receptor and coactivator results in expression of the gene, and the effects can be shown to be unrelated to effects on hormone-receptor interactions, the potential drug or agent may be considered an antagonist of the nuclear hormone receptor coactivator. In constrast, if incubation of the potential drug with the receptor and corresponding hormone in the absence of the coactivator results in repression of expression of the gene, the potential drug or agent may have applications as a mimic of the the nuclear receptor coactivator.

Per the above, the potential drugs or agents may be considered as antagonists of, or have applications as a mimic to the nuclear receptor coactivator if the effects can also be shown to be unrelated to effects on corresponding hormone-nuclear hormone receptor interactions i.e., the potential drug or agent is not a conventional hormone antagonist or mimic. In these cases, the action of the potential drug or agent as a coactivator mimic or antagonist may involve effects on interactions between receptor and coactivator or on interactions between coactivator and components of the general transcription machinery, or on interactions between various TRAPS in the coactivator complex. The potential drug or agent of the invention has applications in interacting with the nuclear hormone receptor, other coactivators, or the general transcription machinery, thus manifesting their effects as antagonist or mimics of coactivator function.

Examples of nuclear hormone receptors and their corresponding hormones that have applications in an assay system for screening potential drugs and other agents for ability to mimic or antagonize the functions of a corresponding hormone include, but are not limited to α and β isoforms of thyroid hormone receptor (TR), having thyroid hormone as a corresponding hormone, vitamin D receptor (VDR) having vitamin D as a corresponding hormone, isoforms α, β, and γ of retinoic acid receptor (RAR) having trans-retinoic acid or 9-cis retinoic acid as a corresponding hormone, α, β, and γ isoforms of retinoid X receptor (RXR), having retinoids (compounds related to retinoate, the carboxylate form of vitamin $A_1$) as a corresponding hormone, α and β isoforms of estrogen receptor (ER), having estradiol or estriol as a corresponding hormone, progesterone receptor (PR) having progesterone as a corresponding hormone, androgen receptor (AR) having testosterone as a corresponding hormone, glucocorticoid receptor (GR) having cortisol as a corresponding hormone, mineralcorticoid receptor (MR) having aldosterone as a corresponding hormone, and α and γ isoforms of peroxisome proliferation-activated receptor (PPAR) having respectively Wy14643 and 15-deoxy-$D^{12,14}$-prostaglandin J2 as corresponding hormones.

Furthermore, examples of coactivators having applications in an assay system of the present invention include, but are not limited to TRAP220 or TRAP100, conserved variants thereof, fragments thereof, or analogs or derivatives thereof.

Accordingly, it a principal object of the present invention to provide isolated nucleic acid sequences that encode nuclear hormone receptor coactivators such as TRAP220 and TRAP100.

It is another object of the present invention to provide isolated and homogenous nuclear hormone receptor coactivators such as TRAP220 and TRAP100, along with conserved variants thereof, fragments thereof, or analogs or derivatives thereof.

It is yet another object of the present invention to provide antibodies having a nuclear hormone receptor coactivator as an immunogen. Such antibodies have numerous applications in screening cellular samples for the presence of a nuclear hormone receptor coactivator of the invention.

It is yet another object of the invention to provide cloning vectors which can replicate isolated nucleic acids that encode nuclear hormone receptor factors, conserved variants thereof, fragments thereof, or analogs or derivatives thereof.

It is yet another object of the invention to provide expression vectors to produce nuclear hormone receptor factors such as TRAP220 or TRAP100, conserved variants thereof, fragments thereof, or analogs or derivatives thereof, as well as unicellular hosts transformed or transfected with such expression vectors.

Furthermore, it is an object of the invention to provide a method of producing a nuclear hormone receptor factor such as TRAP220 or TRAP100, as well as conserved variants thereof, fragments thereof, or analogs or derivatives thereof, using unicellular hosts of the invention.

It is yet another object of the invention to provide pharmaceutical compositions which can modulate gene expression, and methods of modulating gene expression wherein a therapeutically effective amount of a pharmaceutical composition of the invention is administered to a subject.

Another object of the invention is to provide an assay system for determining whether a drug or agent potentially mimics the function of a hormone which binds to a nuclear hormone receptor.

It is yet another object of the invention to provide an assay system for determining whether a particular drug or agent mimics the function of a nuclear hormone receptor coactivator, such as TRAP220 or TRAP100.

These and other aspects of the present invention will be better appreciated by reference to the following drawings and Detailed Description.

BRIEF DESCRIPTION OF THE DRAWINGS

FIG. 1 is DNA sequence of an isolated nucleic acid molecule which encodes TRAP220.

FIG. 2 is the amino acid sequence of TRAP220.

FIG. 3 is the DNA sequence of an isolated nucleic acid molecule which encodes TRAP100.

FIG. 4 is the amino acid sequence of TRAP100.

FIG. 6. Gel filtration of purified TR-TRAP complex in the absence of $T_3$. (A) Silver staining. 1 mg of TR-TRAP complex was fractionated on Superose 6, resolved by SDS-PAGE with 6% (upper) and 8% (lower) acrylamide gels and detected by silver staining. The void volume was not collected. The bars on the right indicate the positions of individual TRAPs. (B) Western blot analysis. Proteins (molecular weight less than 85 kDa) in the bottom part of the SDS-PAGE analysis in (A) were transferred and probed with anti-TRα antibody. Proteins from an analysis equivalent to the SDS-PAGE analysis in (A) were probed with anti-TRAP220, TRAP150 and TRAP100 antibodies.

Figure 5B:
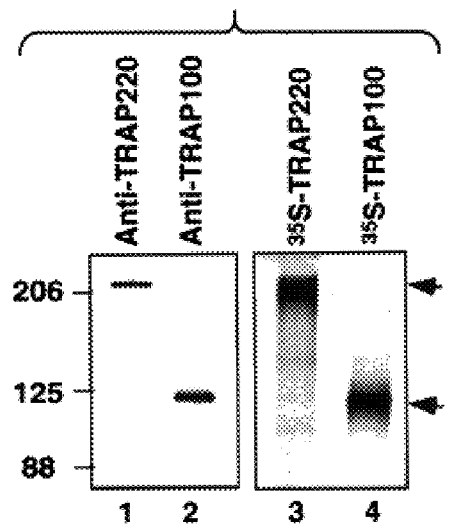
FIG. 5. Cloning and expression of TRAP220 and TRAP100. (A) Amino acid sequences of TRAP220 and TRAP100. Polypeptide microsequences are underlined. The circled glycine 216 indicates the point from which a truncated TRAP220 differs from full-length TRAP220 (see Example, Infra). LXXLL motifs are boxed. A C4 type zinc finger region is bracketed. The putative ATP/GTP binding site is underlined with a dashed line. (B) TRAP220 and TRAP100 expression. Lanes 1 and 2 show an immunoblot analysis of purified TR-TRAP complex probed with antibodies against recombinant TRAP220 and TRAP100. Lanes 3 and 4 show an SDS-PAGE autoradiographic analysis of $^{35}$S-labeled TRAP220 and TRAP100 generated by in vitro translation. (C) Northern blot. The upper panel shows TRAP220 and the lower one TRAP100.

Luciferase values have been normalized to b-galactosidase activity and corrected for the activity of the reporter in the absence of ectopic TRα expression. (C) Specificity of TRAP220 function. Cells were transfected with 2 µg of pG5-luc (19), 2 µg of pRSV-b-gal, 0.1 µg of pGAL-CTA (19) and 3 µg of pCIN4-TRAP220 or an empty pCIN4 vector. Open and closed bars indicate activities in the absence and presence, respectively, of $10^{-7}$ M 3,3',5-triodo-L-thyronine ($T_3$).

FIG. 10. TRAP220/2 inhibition of TR- and VDR-mediated transcription in vitro. (A) TRAP220/2 specifically inhibits TR-mediated transcriptional activation. Reactions (7) contained 5 µl of Namalwa nuclear extract (about 40 µg protein), $10^{-7}$ M 3,3',5-triiodothyroacetic acid, 100 ng of RXRα, 100 ng of pTRE4/130, 25 ng of pWtML200 as an internal control template, 5 ng of TRAP-associated TR and indicated amounts (mg) of GST or GST-TRAP220/2. (B) GST-TRAP220/2 also inhibits VDR-mediated transcriptional activation. Reactions contained 5 µl of Namalwa nuclear extract, 25 ng of RXRα, 14 ng of baculovirus expressed hVDR, $10^{-7}$ M 1α,25$(OH)_2D_3$, 100 ng of pVDRE4/130, 15 ng of pWtML200 and the indicated amounts (mg) of GST or GST fusion proteins.

DETAILED DESCRIPTION OF THE INVENTION

The present invention is based upon Applicants' discovery of heretofore unknown nucleic acid sequences which encode TRAP220 and TRAP100. Furthermore, the Applicants have discovered that surprisingly, the amino acid sequences of TRAP220 and TRAP100 share no obvious common motifs with other coactivators, except for the LXXLL motifs implicated in receptor-coactivator interactions, and described infra. Most importantly, Applicants have discovered that TRAP220 and TRAP100 bind their respective receptors in a ligand dependent manner, and that such binding is necessary to the activation of the receptors and their regulation of the expression of specific genes in the nucleus of a cell.

Furthermore, the present invention is based upon Applicant's discovery that surprisingly, coactivators of the present invention bind to numerous nuclear hormone receptors, and consequently have ability to activate the nuclear hormone receptor to regulate the expression of a particular gene in the presence of the receptor's corresponding hormone.

Accordingly, as used herein, the phrase "nuclear hormone receptor coactivator" refers to a protein which binds in a ligand dependent manner with a nuclear hormone receptor and acts in concert with a hormone to activate the receptor, which then regulates the expression of a particular gene in the nucleus of a eukaryotic cell. Examples of nuclear hormone receptors set forth herein include TRAP220 and TRAP100.

Furthermore, as used herein the phrase "nuclear hormone receptor" refers a receptor located in the nucleus of a eukaryotic cell which binds to its corresponding hormone and a complex comprising coactivators of the invention, and as a result of this binding is activated to regulate (either activate or suppress) expression of a specific gene. Examples of nuclear hormone receptors include, but are not limited to all isoforms of thyroid hormone receptor (TR), vitamin D receptor (VDR), retinoic acid receptor (RAR), retinoid X receptor (RXR), estrogen receptor (ER), progesterone receptor (PR), androgen receptor (AR), glucorticoid receptor (GR), mineral corticoid receptor (MR) and peroxisome proliferation-activated receptor (PPAR).

The term "ligand" as used herein refers to a small molecule that binds specifically to a larger one; for example, a hormone is the ligand for its specific protein receptor.

Also, the phrase "corresponding hormone" refers to a specific hormone that binds to, and in the presence of a coactivator, activates a specific nuclear hormone receptor to regulate expression of a specific gene. Examples of nuclear hormone receptors and their corresponding hormones that have applications in the present invention include, but are not limited to α and β isoforms of thyroid hormone receptor (TR), having thyroid hormone as a corresponding hormone, vitamin D receptor (VDR) having vitamin D as a corresponding hormone, isoforms α, β, and γ of retinoic acid receptor (RAR) having trans-retinoic acid or 9-cis retinoic acid as a corresponding hormone, α, β, and γ isoforms of retinoid X receptor (RXR), having retinoids (compounds related to retinoate, the carboxylate form of vitamin $A_1$) as a corresponding hormone, α and β isoforms of estrogen receptor (ER), having estradiol or estriol as a corresponding hormone, progesterone receptor (PR) having progesterone as a corresponding hormone, androgen receptor (AR) having testosterone as a corresponding hormone, glucocorticoid receptor (GR) having cortisol as a corresponding hormone, mineralcorticoid receptor (MR) having aldosterone as a corresponding hormone, and α and γ isoforms of peroxisome proliferation-activated receptor (PPAR) having respectively Wy14643 and 15-deoxy-$D^{12,14}$-prostaglandin J2 as corresponding hormones.

In accordance with the present invention there may be employed conventional molecular biology, microbiology, and recombinant DNA techniques within the skill of the art. Such techniques are explained fully in the literature. See, e.g., Sambrook, Fritsch & Maniatis, *Molecular Cloning: A Laboratory Manual,* Second Edition (1989) Cold Spring Harbor Laboratory Press, Cold Spring Harbor, New York (herein "Sambrook et al., 1989"); *DNA Cloning: A Practical Approach,* Volumes I and II (D. N. Glover ed. 1985); *Oligonucleotide Synthesis* (M. J. Gait ed. 1984); *Nucleic Acid Hybridization* [B. D. Hames & S. J. Higgins eds. (1985)]; *Transcription And Translation* [B. D. Hames & S. J. Higgins, eds. (1984)]; *Animal Cell Culture* [R. I. Freshney, ed. (1986)]; *Immobilized Cells And Enzymes* [IRL Press, (1986)]; B. Perbal, *A Practical Guide To Molecular Cloning* (1984); F. M. Ausubel et al. (eds.), *Current Protocols in Molecular Biology,* John Wiley & Sons, Inc. (1994).

Therefore, if appearing herein, the following terms shall have the definitions set out below.

A "vector" is a replicon, such as plasmid, phage or cosmid, to which another DNA segment may be attached so as to bring about the replication of the attached segment. A "replicon" is any genetic element (e.g., plasmid, chromosome, virus) that functions as an autonomous unit of DNA replication in vivo, i.e., capable of replication under its own control.

A "cassette" refers to a segment of DNA that can be inserted into a vector at specific restriction sites. The segment of DNA encodes a polypeptide of interest, and the cassette and restriction sites are designed to ensure insertion of the cassette in the proper reading frame for transcription and translation.

A cell has been "transfected" by exogenous or heterologous DNA when such DNA has been introduced inside the cell. A cell has been "transformed" by exogenous or heterologous DNA when the transfected DNA effects a phenotypic change. Preferably, the transforming DNA should be integrated (covalently linked) into chromosomal DNA making up the genome of the cell.

"Heterologous" DNA refers to DNA not naturally located in the cell, or in a chromosomal site of the cell. Preferably, the heterologous DNA includes a gene foreign to the cell.

A "nucleic acid molecule" refers to the phosphate ester polymeric form of ribonucleosides (adenosine, guanosine, uridine or cytidine; "RNA molecules") or deoxyribonucleosides (deoxyadenosine, deoxyguanosine, deoxythymidine, or deoxycytidine; "DNA molecules"), or any phosphoester analogs thereof, such as phosphorothioates and thioesters, in either single stranded form, or a double-stranded helix. Double stranded DNA-DNA, DNA-RNA and RNA-RNA helices are possible. The term nucleic acid molecule, and in particular DNA or RNA molecule, refers only to the primary and secondary structure of the molecule, and does not limit it to any particular tertiary forms. Thus, this term includes double-stranded DNA found, inter alia, in linear or circular DNA molecules (e.g., restriction fragments), plasmids, and chromosomes. In discussing the structure of particular double-stranded DNA molecules, sequences may be described herein according to the normal convention of giving only the sequence in the 5' to 3' direction along the nontranscribed strand of DNA (i.e., the strand having a sequence homologous to the mRNA). A "recombinant DNA molecule" is a DNA molecule that has undergone a molecular biological manipulation.

A nucleic acid molecule is "hybridizable" to another nucleic acid molecule, such as a cDNA, genomic DNA, or RNA, when a single stranded form of the nucleic acid molecule can anneal to the other nucleic acid molecule under the appropriate conditions of temperature and solution ionic strength (see Sambrook et al., supra). The conditions of temperature and ionic strength determine the "stringency" of the hybridization. For preliminary screening for homologous nucleic acids, low stringency hybridization conditions, corresponding to a $T_m$ of 55°, can be used, e.g., 5×SSC, 0.1% SDS, 0.25% milk, and no formamide; or 30% formamide, 5×SSC, 0.5% SDS). Moderate stringency hybridization conditions correspond to a higher $T_m$, e.g., 40% formamide, with 5× or 6×SSC. High stringency hybridization conditions correspond to the highest $T_m$, e.g., 50% formamide, 5× or 6×SSC. Hybridization requires that the two nucleic acids contain complementary sequences, although depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the greater the value of $T_m$ for hybrids of nucleic acids having those sequences. The relative stability (corresponding to higher $T_m$) of nucleic acid hybridizations decreases in the following order: RNA:RNA, DNA:RNA, DNA:DNA. For hybrids of greater than 100 nucleotides in length, equations for calculating $T_m$ have been derived (see Sambrook et al., supra, 9.50–0.51). For hybridization with shorter nucleic acids, i.e., oligonucleotides, the position of mismatches becomes more important, and the length of the oligonucleotide determines its specificity (see Sambrook et al., supra, 11.7–11.8). Preferably a minimum length for a hybridizable nucleic acid is at least about 10 nucleotides; preferably at least about 15 nucleotides; and more preferably the length is at least about 20 nucleotides; and most preferably 30 nucleotides.

In a specific embodiment, the term "standard hybridization conditions" refers to a $T_m$ of 55° C., and utilizes conditions as set forth above. In a preferred embodiment, the $T_m$ is 60° C.; in a more preferred embodiment, the $T_m$ is 65° C.

"Homologous recombination" refers to the insertion of a foreign DNA sequence of a vector in a chromosome. Preferably, the vector targets a specific chromosomal site for homologous recombination. For specific homologous recombination, the vector will contain sufficiently long regions of homology to sequences of the chromosome to allow complementary binding and incorporation of the vector into the chromosome. Longer regions of homology, and greater degrees of sequence similarity, may increase the efficiency of homologous recombination.

A DNA "coding sequence" is a double-stranded DNA sequence which is transcribed and translated into a polypeptide in a cell in vitro or in vivo when placed under the control of appropriate regulatory sequences. The boundaries of the coding sequence are determined by a start codon at the 5' (amino) terminus and a translation stop codon at the 3' (carboxyl) terminus. A coding sequence can include, but is not limited to, prokaryotic sequences, cDNA from eukaryotic MRNA, genomic DNA sequences from eukaryotic (e.g., mammalian) DNA, and even synthetic DNA sequences. If the coding sequence is intended for expression in a eukaryotic cell, a polyadenylation signal and transcription termination sequence will usually be located 3' to the coding sequence.

Transcriptional and translational control sequences are DNA regulatory sequences, such as promoters, enhancers, terminators, and the like, that provide for the expression of a coding sequence in a host cell. In eukaryotic cells, polyadenylation signals are control sequences.

A "promoter sequence" or "promoter" is a DNA regulatory region capable of binding RNA polymerase in a cell and initiating transcription of a downstream (3' direction) coding sequence. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site (conveniently defined for example, by mapping with nuclease S1), as well as protein binding domains (consensus sequences) responsible for the binding of RNA polymerase.

A coding sequence is "under the control" of transcriptional and translational control sequences in a cell when RNA polymerase transcribes the coding sequence into mRNA, which is then trans-RNA spliced and translated into the protein encoded by the coding sequence.

A "signal sequence" is included at the beginning of the coding sequence of a protein to be expressed on the surface of a cell. This sequence encodes a signal peptide, N-terminal to the mature polypeptide, that directs the host cell to translocate the polypeptide. The term "translocation signal sequence" is used herein to refer to this sort of signal sequence. Translocation signal sequences can be found associated with a variety of proteins native to eukaryotes and prokaryotes, and are often functional in both types of organisms.

As used herein, the term "sequence homology" in all its grammatical forms refers to the relationship between proteins that possess a "common evolutionary origin," including proteins from superfamilies (e.g., the immunoglobulin superfamily) and homologous proteins from different species (e.g., myosin light chain, etc.) (Reeck et al., 1987, Cell 50:667).

Accordingly, the term "sequence similarity" in all its grammatical forms refers to the degree of identity or correspondence between nucleic acid or amino acid sequences of proteins that do not share a common evolutionary origin (see Reeck et al., supra). However, in common usage and in the instant application, the term "homologous," when modified with an adverb such as "highly," may refer to sequence similarity and not a common evolutionary origin.

In a specific embodiment, two DNA sequences are "substantially homologous" or "substantially similar" when at least about 50% (preferably at least about 75%. and most preferably at least about 90 or 95%) of the nucleotides match over the defined length of the DNA sequences. Sequences that are substantially homologous can be identified by comparing the sequences using standard software available in sequence data banks, or in a Southern hybridization experiment under, for example, stringent conditions as defined for that particular system. Defining appropriate hybridization conditions is within the skill of the art. See, e.g., Maniatis et al., supra; DNA Cloning, Vols. I & II, supra; Nucleic Acid Hybridization, supra.

Similarly, in a particular embodiment, two amino acid sequences are "substantially homologous" or "substantially similar" when greater than 30% of the amino acids are identical, or greater than about 60% are similar (functionally identical). Preferably, the similar or homologous sequences are identified by alignment using, for example, the GCG (Genetics Computer Group, Program Manual for the GCG Package, Version 7, Madison, Wis.) pileup program.

The term "corresponding to" is used herein to refer similar or homologous sequences, whether the exact position is identical or different from the molecule to which the similarity or homology is measured. Thus, the term "corresponding to" refers to the sequence similarity, and not the numbering of the amino acid residues or nucleotide bases.

As used herein, the term "gene" refers to an assembly of nucleotides that encode a polypeptide, and includes cDNA and genomic DNA nucleic acids.

Isolated Nucleic Acid Molecules Encoding Nuclear Hormone Receptor Coactivators, Conserved Variants thereof, Fragments thereof, or Analogs or Derivatives thereof, and Isolated Nucleic Acid Molecules Hybridizable thereto Under Standard Hybridization Conditions The present invention contemplates isolation of a nucleic acid molecule, degenerate variants thereof, fragments thereof, or analogs or derivatives thereof, which encodes an isolated and homogenous nuclear hormone receptor coactivator, conserved variants thereof, fragments thereof, or analogs or derivatives thereof. Examples of such isolated nucleic acid molecules comprise a DNA sequence of FIG. 1 (SEQ ID NO:1). FIG. 3 (SEQ ID NO:3), degenerate variants of these sequences, fragments thereof, or analogs or derivatives thereof. These isolated nucleic acid molecules encode nuclear hormone receptor coactivators such as TRAP220 and TRAP100, including a full length, or naturally occurring form of these coactivators, and any antigenic fragments thereof from any animal, particularly mammalian, and more particularly human, source.

Furthermore, the present invention extends to isolated nucleic acid molecules hybridizable under standard hybridization conditions to an isolated nucleic acid molecule comprising a DNA sequence of FIG. 1 (SEQ ID NO:1), FIG. 3 (SEQ ID NO:3), degenerate variants thereof, fragments thereof, or analogs or derivatives thereof.

A gene comprising a DNA sequence of FIG. 1 (SEQ ID NO:1), or FIG. 3 (SEQ ID NO:3), which encodes a nuclear regulatory coactivator comprising an amino acid sequence of FIG. 2 (SEQ ID NO:2), FIG. 4 (SEQ ID NO:4) respectively, whether genomic DNA or cDNA, can be isolated from any source, particularly from a human cDNA or genomic library. Methods for obtaining gene are well known in the art, as described above (see, e.g., Sambrook et al., 1989, supra).

Accordingly, any animal cell potentially can serve as the nucleic acid source for the molecular cloning of a gene comprising a DNA sequence of FIG. 1 (SEQ ID NO:1), or FIG. 3 (SEQ ID NO:3). The DNA may be obtained by standard procedures known in the art from cloned DNA (e.g., a DNA "library"), and preferably is obtained from a cDNA library prepared from tissues with high level expression of a nuclear hormone receptor coactivator by chemical synthesis, by cDNA cloning, or by the cloning of genomic DNA, or fragments thereof, purified from the desired cell (See, for example, Sambrook et al., 1989, supra; Glover, D. M. (ed.), 1985, DNA Cloning: A Practical Approach, MRL Press, Ltd., Oxford, U.K. Vol. I, II). Clones derived from genomic DNA may contain regulatory and intron DNA regions in addition to coding regions; clones derived from cDNA will not contain intron sequences. Whatever the source, genes comprising a DNA sequence of FIG. 1 (SEQ ID NO:1), or FIG. 3 (SEQ ID NO:3) should be molecularly cloned into a suitable vector for propagation of the gene.

In the molecular cloning of the gene from genomic DNA, DNA fragments are generated, some of which will encode the desired gene. The DNA may be cleaved at specific sites using various restriction enzymes. Alternatively, one may use DNAse in the presence of manganese to fragment the DNA, or the DNA can be physically sheared, as for example, by sonication. The linear DNA fragments can then be separated according to size by standard techniques, including but not limited to, agarose and polyacrylamide gel electrophoresis and column chromatography.

Once the DNA fragments are generated, identification of the specific DNA fragment containing a gene comprising a DNA sequence of FIG. 1 (SEQ ID NO:1), or a sequence of FIG. 3 (SEQ ID NO:3) may be accomplished in a number of ways. For example, if an amount of a portion of a gene comprising a DNA sequence of FIG. 1 (SEQ ID NO:1) or FIG. 3 (SEQ ID NO:3), or their specific RNAs, or a fragment thereof, are available and can be purified and labeled, the generated DNA fragments may be screened by nucleic acid hybridization to the labeled probe (Benton and Davis, 1977, Science 196:180; Grunstein and Hogness, 1975, Proc. Natl. Acad. Sci. U.S.A. 72:3961). For example, a set of oligonucleotides corresponding to the partial amino acid sequence information obtained a nuclear hormone receptor coactivator comprising an amino acid sequence of FIG. 2 (SEQ ID NO:2), or FIG. 4 (SEQ ID NO:4) can be prepared and used as probes for DNA encoding a gene comprising a DNA sequence of FIG. 1 (SEQ ID NO:1) or FIG. 3 (SEQ ID NO:3), or as primers for cDNA or mRNA (e.g., in combination with a poly-T primer for RT-PCR). Preferably, a fragment is selected that is highly unique to an isolated nucleic acid molecule of the invention, wherein the isolated nucleic acid molecule comprises a DNA sequence of FIG. 1 (SEQ ID NO:1), or a DNA sequence of FIG. 3 (SEQ ID NO:3). Those DNA fragments with substantial homology to the probe will hybridize. As noted above, the greater the degree of homology, the more stringent hybridization conditions can be used. In a specific embodiment, stringency hybridization conditions are used to identify a nucleic acid molecule homologous to the DNA sequence of an isolated nucleic acid molecule of the invention, wherein the isolated nucleic acid molecule comprises a DNA sequence of FIG. 1 (SEQ ID NO:1) or FIG. 3 (SEQ ID NO:3).

Further selection can be carried out on the basis of the properties of the gene, e.g., if the gene encodes a protein product having the isoelectric, electrophoretic, amino acid composition, or partial amino acid sequence of a nuclear hormone receptor coactivator such as TRAP220 or TRAP100, comprising respectively an amino acid sequence of FIG. 2 (SEQ ID NO:2), FIG. 4 (SEQ ID NO:4) respectively, as disclosed herein. Thus, the presence of the gene may be detected by assays based on the physical, chemical, or immunological properties of its expressed product. For example, cDNA clones, or DNA clones which hybrid-select the proper mRNAs, can be selected which produce a protein that, e.g., has similar or identical electrophoretic migration, isoelectric focusing or non-equilibrium pH gel electrophoresis behavior, proteolytic digestion maps, or antigenic properties as known for TRAP220 or TRAP100. In another aspect, a protein that has an apparent molecular weight of approximately 125 kDa, and which is digested by a particular protease to form a defined ladder (rather than a smear) of lower molecular weight bands in a pattern that is unique to TRAP220 when digested by the particular protease, the protein is a good candidate for TRAP220. Likewise, a protein that has an apparent molecular weight of approximately 90 kDa. and which is digested with a particular protease to form a defined ladder (rather than a smear) of lower molecular weight bands in a pattern that is unique to TRAP100 when digested by the particular protease, the protein is a good candidate for TRAP100.

An isolated nucleic acid molecule of the invention comprising a DNA sequence of FIG. 1 (SEQ ID NO:1), or a DNA sequence of FIG. 3 (SEQ ID NO:3) can also be identified by mRNA selection, i.e., by nucleic acid hybridization followed by in vitro translation. In this procedure, nucleotide fragments are used to isolate complementary mRNAs by hybridization. Such DNA fragments may represent available, purified trap220 or trap100 DNA, or may be synthetic oligonucleotides designed from the partial amino acid sequence information. Immunoprecipitation analysis or functional assays (e.g., the ability of the coactivator to activate a thyroid hormone receptor in the presence of thyroid hormone) of the in vitro translation products of the products of the isolated mRNAs identifies the mRNA and, therefore, the complementary DNA fragments, that contain the desired sequences. In addition, specific mRNAs may be selected by adsorption of polysomes isolated from cells to immobilized antibodies specifically directed against TRAP220 or TRAP100, such as the anti-GST-TRAP220/2 and GST-TRAP100(1–253) made in rabbits.

A radiolabeled trap220 or trap100 cDNA can be synthesized using the selected mRNA (from the adsorbed polysomes) as a template. The radiolabeled mRNA or cDNA may then be used as a probe to identify homologous DNA fragments from among other genomic DNA fragments.

Moreover, due to degenerate nature of codons in the genetic code, a nuclear hormone receptor coactivator of the invention, such as TRAP220 and TRAP100 can be encoded by numerous degenerate variants of isolated nucleic acid molecules of the invention. "Degenerate nature" refers to the use of different three-letter codons to specify a particular amino acid pursuant to the genetic code. It is well known in the art that the following codons can be used interchangeably to code for each specific amino acid:

| | |
|---|---|
| Phenylalanine (Phe or F) | UUU or UUC |
| Leucine (Leu or L) | UUA or UUG or CUU or CUC or CUA or CUG |
| Isoleucine (Ile or I) | AUU or AUC or AUA |
| Methionine (Met or M) | AUG |
| Valine (Val or V) | GUU or GUC of GUA or GUG |
| Serine (Ser or S) | UCU or UCC or UCA or UCG or AGU or AGC |
| Proline (Pro or P) | CCU or CCC or CCA or CCG |
| Threonine (Thr or T) | ACU or ACC or ACA or ACG |
| Alanine (Ala or A) | GCU or GCG or GCA or GCG |
| Tyrosine (Tyr or Y) | UAU or UAC |
| Histidine (His or H) | CAU or CAC |
| Glutamine (Gln or Q) | CAA or CAG |
| Asparagine (Asn or N) | AAU or AAC |
| Lysine (Lys or K) | AAA or AAG |
| Aspartic Acid (Asp or D) | GAU or GAC |
| Glutamic Acid (Glu or E) | GAA or GAG |
| Cysteine (Cys or C) | UGU or UGC |
| Arginine (Arg or R) | CGU or CGC or CGA or CGG or AGA or AGG |
| Glycine (Gly or G) | GGU or GGC or GGA or GGG |
| Tryptophan (Trp or W) | UGG |
| Termination codon | UAA (ochre) or UAG (amber) or UGA (opal) |

It should be understood that the codons specified above are for RNA sequences. The corresponding codons for DNA have a T substituted for U.

Detectably Labeled Isolated Nucleic Acid Molecules Encoding a Nuclear Hormone Receptor Coactivator, Conserved Variants thereof, Fragments thereof, or Analogs or Derivatives thereof The present invention further extends to detectably labeled isolated nucleic acid molecules encoding a nuclear hormone receptor coactivator, conserved variants thereof, fragments thereof, or analogs or derivatives thereof, wherein the detectably labeled isolated nucleic acid molecule comprises a DNA sequence of FIG. 1 (SEQ ID NO:1), FIG. 3 (SEQ ID NO:3), degenerate variants thereof, fragments thereof, or analogs or derivatives thereof. Furthermore, the present invention extends to a detectably labeled isolated nucleic acid molecule hybridizable under standard hybridization conditions to an isolated nucleic acid comprising a DNA sequence of FIG. 1 (SEQ ID NO:1), FIG. 3 (SEQ ID NO:3), degenerate variants thereof, fragments thereof, or analogs or derivatives thereof. Detectably labeled isolated nucleic acid molecules have applications as probes for identify DNA fragments that are homologous to isolated nucleic acid molecules of the invention from among other genomic DNA fragments.

Numerous detectable labels have applications in the present invention. Examples include enzymes, fluorophores (e.g., fluorescene isothiocyanate (FITC), phycoerythrin (PE), Texas red (TR), rhodamine, free or chelated lanthanide series salts, especially $Eu^{3+}$, to name a few fluorophores), chromophores, radioisotopes, chelating agents, dyes, colloidal gold, latex particles, ligands (e.g., biotin), and chemiluminescent agents. When a control marker is employed, the same or different labels may be used for the receptor and control marker.

Furthermore, a detectable label can be a radioactive isotope. Examples of isotopes having applications as detectable labels in the invention include $^3H$, $^{14}C$, $^{32}P$, $^{35}S$, $^{36}Cl$, $^{51}Cr$, $^{57}Co$, $^{58}Co$, $^{59}Fe$, $^{90}Y$, $^{125}I$, $^{131}I$, and $^{186}Re$ to name only a few. In addition, when a radiolabel is used, known currently available counting procedures may be utilized.

In the instance where the label is an enzyme, detection may be accomplished by any of the presently utilized colorimetric, spectrophotometric, fluorospectrophotometric, amperometric or gasometric techniques known in the art.

Direct labels are one example of labels which can be used according to the present invention. A direct label has been defined as an entity, which in its natural state, is readily visible, either to the naked eye, or with the aid of an optical filter and/or applied stimulation, e.g. U.V. light to promote fluorescence. Among examples of colored labels, which can be used according to the present invention, include metallic sol particles, for example, gold sol particles such as those described by Leuvering (U.S. Pat. No. 4,313,734); dye sole particles such as described by Gribnau et al. (U.S. Pat. No. 4,373,932) and May et al. (WO 88/08534); dyed latex such as described by May, supra, Snyder (EP-A 0 280 559 and 0 281 327); or dyes encapsulated in liposomes as described by Campbell et al. (U.S. Pat. No. 4,703,017). Other direct labels include a radionucleotide, a fluorescent moiety or a luminescent moiety.

In addition to these direct labeling devices, indirect labels comprising enzymes can also be used according to the present invention. For example, alkaline phosphatase and horseradish peroxidase, lysozyme, glucose-6-phosphate dehydrogenase, lactate dehydrogenase, urease, these and others which have been discussed in detail by Eva Engvall in Enzyme Immunoassay ELISA and EMIT in *Methods in Enymology*, 70. 419–439, 1980 and in U.S. Pat. No. 4,857, 453, can be conjugated to an isolated nucleic acid molecule of the invention.

Other labels for use in the invention include magnetic beads or magnetic resonance imaging labels.

Cloning Vectors

The present invention also extends to cloning vectors comprising an isolated nucleic acid molecule of the present invention, or degenerate variants thereof, fragments thereof, analogs or derivatives thereof, and an origin of replication. For purposes of this Application, an "origin of replication" refers to those DNA sequences that participate in DNA synthesis.

As explained above, the present invention extends to a cloning vector comprising an isolated nucleic acid molecule comprising a DNA sequence of FIG. 1 (SEQ ID NO:1), degenerate variants thereof, fragments thereof, or analogs or derivatives thereof, which encodes a nuclear hormone receptor coactivator, conserved variants thereof, fragments thereof, or analogs or derivatives thereof, and an origin of replication. Furthermore, a cloning vector of the present invention comprises an isolated nucleic acid molecule hybridizable under standard hybridization conditions to an isolated nucleic acid molecule comprising a DNA sequence of FIG. 1 (SEQ ID NO:1), degenerate variants thereof, fragments thereof, or analogs or derivatives thereof, and an origin of replication. A large number of vector-host systems known in the art may be used. Possible vectors include, but are not limited to plasmids or modified viruses, but the vector system must be compatible with the host cell used.

In another embodiment, a cloning vector of the invention comprises an isolated nucleic acid molecule comprising a DNA sequence of FIG. 3 (SEQ ID NO:3), degenerate variants thereof, fragments thereof, or analogs or derivatives thereof. Moreover, a cloning vector of the invention may comprise an isolated nucleic acid molecule hybridizable under standard hybridization conditions to an isolated nucleic acid molecule comprising a DNA sequence of FIG. 3 (SEQ ID NO:3), degenerate variants thereof, fragments thereof, or analogs or derivatives thereof, operatively associated with a promoter.

Examples of vectors having applications in the present invention include, but are not limited to *E. coli.* bacteriophages such as lambda derivatives, or plasmids such as pBR322 derivatives or pUC plasmid derivatives, e.g., pGEX vectors, pmal-c, pFLAG, etc. The insertion an isolated nucleic acid molecule of the invention into a cloning vector can, for example, be accomplished by ligating the isolated nucleic acid molecule into a cloning vector which has complementary cohesive termini. However, if the complementary restriction sites used to fragment the isolated nucleic acid, degenerate variants thereof, fragments thereof, or analogs or derivatives thereof, or an isolated nucleic acid hybridizable thereto under standard hybridization conditions, are not present in the cloning vector, the ends of the isolated nucleic acid molecule, degenerate variants thereof, fragments thereof, or analogs or derivatives thereof, or an isolated nucleic acid molecule hybridizable thereto under standard hybridization conditions may be enzymatically modified. Alternatively, any site desired may be produced by ligating nucleotide sequences (linkers) onto the DNA termini; these ligated linkers may comprise specific chemically synthesized oligonucleotides encoding restriction endonuclease recognition sequences. Such recombinant molecules can then be introduced into host cells via transformation, transfection, infection, electroporation, etc., so that many copies of an isolated nucleic acid molecule of the present invention, degenerate variants thereof, fragments thereof, or analogs or derivatives thereof can be generated. The cloned isolated nucleic acid molecule may also be contained on a shuttle vector plasmid, which provides for expansion in a cloning cell, e.g., *E. coli,* and facile purification for subsequent insertion into an appropriate expression cell line, if such is desired. For example, a shuttle vector, which is a vector that can replicate in more than one type of organism, can be prepared for replication in both *E. coli* and *Saccharomyces cerevisiae* by linking sequences from an *E. coli* plasmid with sequences from the yeast 2μ plasmid.

In an alternative method, an isolated nucleic acid molecule of the present invention, degenerate variants thereof, fragments thereof, or analogs or derivatives thereof, or an isolated nucleic acid molecule hybridizable thereto under standard hybridization conditions, may be identified and isolated after insertion into a suitable cloning vector in a "shot gun" approach. Enrichment for an isolated nucleic acid molecule, for example, by size fractionation, can be done before insertion into the cloning vector.

Expression Vectors

As stated above, the present invention extends to an isolated nucleic acid molecule comprising a DNA sequence of FIG. 1 (SEQ ID NO:1) or FIG. 3 (SEQ ID NO:3), degenerate variants thereof, fragments thereof, or analogs or derivatives thereof, or an isolated nucleic acid molecule hybridizable thereto under standard hybridization conditions.

Isolated nucleic acid molecules of the present invention can be inserted into an appropriate expression vector, i.e., a vector which contains the necessary elements for the transcription and translation of the inserted protein-coding sequence. Such elements are termed herein a "promoter." Thus, an isolated nucleic acid molecule of the invention comprising a DNA sequence of FIG. 1 (SEQ ID NO:1), FIG.

3 (SEQ ID NO:3), degenerate variants thereof, fragments thereof, or analogs or derivatives thereof, which encode a nuclear hormone receptor coactivator such as TRAP220 or TRAP100, conserved variants thereof, fragments thereof, or analogs or derivatives thereof or an isolated nucleic acid molecules hybridizable thereto under standard hybridization conditions, is operatively associated with a promoter in an expression vector of the invention. A isolated nucleic acid molecule is "operatively associated" to an expression control sequence, such as a promoter, when the expression control sequence controls and regulates the transcription and translation of that nucleic acid molecule. The term "operatively associated" includes having an appropriate start signal (e.g., ATG) in front of the DNA sequence to be expressed and maintaining the correct reading frame to permit expression of the DNA sequence under the control of the expression control sequence and production of the desired product encoded by the DNA sequence. If an isolated nucleic acid molecule of the present invention does not contain an appropriate start signal, such a start signal can be inserted into the expression vector in front of (5' of) the isolated nucleic acid molecule.

Both cDNA and genomic sequences can be cloned and expressed under control of such regulatory sequences. An expression vector also preferably includes a replication origin.

The necessary transcriptional and translational signals can be provided on a recombinant expression vector, or they may be supplied by the native gene encoding TRAP220 or TRAP100, and/or its flanking regions.

Potential host-vector systems include but are not limited to mammalian cell systems infected with virus (e.g., vaccinia virus, adenovirus, etc.); insect cell systems infected with virus (e.g., baculovirus); microorganisms such as yeast containing yeast vectors; or bacteria transformed with bacteriophage, DNA, plasmid DNA, or cosmid DNA. The expression elements of vectors vary in their strengths and specificities. Depending on the host-vector system utilized, any one of a number of suitable transcription and translation elements may be used.

Moreover, an isolated nucleic acid molecule of the present invention may be expressed chromosomally, after integration of the coding sequence by recombination. In this regard, any of a number of amplification systems may be used to achieve high levels of stable gene expression (See Sambrook et al., 1989, supra).

Any of the methods previously described for the insertion of DNA fragments into a cloning vector may be used to construct expression vectors comprising an isolated nucleic acid molecule of the present invention, and appropriate transcriptional/translational control signals and the protein coding sequences. These methods may include in vitro recombinant DNA and synthetic techniques and in vivo recombination (genetic recombination).

Expression of an isolated nucleic acid molecule of the present invention, degenerate variants thereof, fragments thereof or analogs or derivatives thereof, or an isolated nucleic acid molecule hybridizable thereto under standard hybridization conditions, may be controlled by any promoter/enhancer element known in the art, but these regulatory elements must be functional in a unicellular host selected for expression. Promoters which may be used to control expression include, but are not limited to, the SV40 early promoter region (Benoist and Chambon, 1981, Nature 290:304–310), the promoter contained in the 3' long terminal repeat of Rous sarcoma virus (Yamamoto, et al., 1980, Cell 22:787–797), the herpes thymidine kinase promoter (Wagner et al., 1981, Proc. Natl. Acad. Sci. U.S.A. 78:1441–1445), the regulatory sequences of the metallothionein gene (Brinster et al., 1982, Nature 296:39–42); prokaryotic expression vectors such as the β-lactamase promoter (Villa-Kamaroff, et al., 1978, Proc. Natl. Acad. Sci. U.S.A. 75:3727–3731), or the tac promoter (DeBoer, et al., 1983, Proc. Natl. Acad. Sci. U.S.A. 80:21–25); see also "Useful proteins from recombinant bacteria" in Scientific American, 1980, 242:74–94; promoter elements from yeast or other fungi such as the Gal 4 promoter, the ADC (alcohol dehydrogenase) promoter, PGK (phosphoglycerol kinase) promoter, alkaline phosphatase promoter; and the animal transcriptional control regions, which exhibit tissue specificity and have been utilized in transgenic animals: elastase I gene control region which is active in pancreatic acinar cells (Swift et al., 1984, Cell 38:639–646; Ornitz et al., 1986, Cold Spring Harbor Symp. Quant. Biol. 50:399–409; MacDonald, 1987, Hepatology 7:425–515); insulin gene control region which is active in pancreatic beta cells (Hanahan, 1985, Nature 315:115–122), immunoglobulin gene control region which is active in lymphoid cells (Grosschedl et al., 1984. Cell 38:647–658: Adames et al., 1985, Nature 318:533–538; Alexander et al., 1987, Mol. Cell. Biol. 7:1436–1444), mouse mammary tumor virus control region which is active in testicular, breast, lymphoid and mast cells (Leder et al., 1986, Cell 45:485–495), albumin gene control region which is active in liver (Pinkert et al., 1987, Genes and Devel. 1:268–276), alpha-fetoprotein gene control region which is active in liver (Krumlauf et al., 1985, Mol. Cell. Biol. 5:1639–1648; Hammer et al., 1987, Science 235:53–58), alpha 1-antitrypsin gene control region which is active in the liver (Kelsey et al., 1987, Genes and Devel. 1:161–171), beta-globin gene control region which is active in myeloid cells (Mogram et al., 1985, Nature 315:338–340; Kollias et al., 1986, Cell 46:89–94), myelin basic protein gene control region which is active in oligodendrocyte cells in the brain (Readhead et al., 1987, Cell 48:703–712), myosin light chain-2 gene control region which is active in skeletal muscle (Sani, 1985, Nature 314:283–286), and gonadotropic releasing hormone gene control region which is active in the hypothalamus (Mason et al., 1986, Science 234:1372–1378).

Expression vectors comprising an isolated nucleic acid molecule comprising a DNA sequence of FIG. 1 (SEQ ID NO:1), FIG. 3 (SEQ ID NO:3), degenerate variants thereof, fragments thereof, or analogs or derivatives thereof, which encode a nuclear hormone receptor coactivator of the present invention, or an expression vector comprising an isolated nucleic acid molecule hybridizable under standard hybridization conditions to an isolated nucleic acid molecule of the present invention, can be identified by four general approaches: (a) PCR amplification of the desired plasmid DNA or specific mRNA, (b) nucleic acid hybridization, (c) presence or absence of selection marker gene functions, and (d) expression of inserted sequences. In the first approach, the nucleic acids can be amplified by PCR to provide for detection of the amplified product. In the second approach, the presence of a foreign gene inserted in an expression vector can be detected by nucleic acid hybridization using probes comprising sequences that are homologous to an inserted marker gene. In the third approach, the recombinant vector/host system can be identified and selected based upon the presence or absence of certain "selection marker" gene functions (e.g., β-galactosidase activity, thymidine kinase activity, resistance to antibiotics, transformation phenotype, occlusion body formation in baculovirus, etc.) caused by the insertion of foreign genes in the vector. In another example, if an isolated nucleic acid molecule comprising a DNA sequence of FIG. 1 (SEQ ID NO:1), FIG. 3 (SEQ ID NO:3), degenerate variants thereof, fragments thereof, or analogs or derivatives thereof, or an isolated nucleic acid molecule hybridizable thereto under standard hybridization conditions, which encode a nuclear hormone receptor coactivator comprising an amino acid sequence of FIG. 2 (SEQ ID NO:2), FIG. 4 (SEQ ID NO:4), conserved variants thereof, fragments thereof, or analogs or derivatives thereof is inserted within the "selection marker" gene sequence of the vector, recombinants containing the insert can be identified by the absence of the inserted gene function. In the fourth approach, recombinant expression vectors can be identified by assaying for the activity, biochemical, or immunological characteristics of the gene product expressed by the recombinant, provided that the expressed protein assumes a functionally active conformation.

Once a particular recombinant DNA molecule is identified and isolated, several methods known in the art may be used to propagate it. Moreover, once a suitable host system and growth conditions are established, expression vectors of the present invention can be propagated and prepared in quantity. As previously explained, the expression vectors which can be used include, but are not limited to, the following vectors or their derivatives: human or animal viruses such as vaccinia virus or adenovirus; and plasmid and cosmid DNA vectors, to name but a few.

In addition, a unicellular host cell strain may be chosen which modulates the expression of the inserted sequences, or modifies and processes the gene product in the specific fashion desired. Different host cells have characteristic and specific mechanisms for the translational and post-translational processing and modification (e.g., glycosylation, cleavage [e.g., of signal sequence]) of proteins. Unicellular host cells of the present invention, include, but are not limited to *E. coli,* Pseudonomas, Bacillus, Strepomyces, yeast, CHO, R1.1, B-W, L-M, COS1, COS7, BSC1, BSC40, BMT10, Sf9 cells, and NIH 3T3 cells.

Appropriate cell lines or host systems can be chosen to ensure the desired modification and processing of the foreign protein expressed. Expression in eukaryotic cells can increase the likelihood of "native" glycosylation and folding of a heterologous protein. Moreover, expression in mammalian cells can provide a tool for reconstituting, or constituting, activity of TRAP220 or TRAP100. Furthermore, different vector/host expression systems may affect processing reactions, such as proteolytic cleavages, to a different extent.

Expression and cloning vectors for that matter are introduced into desired unicellular hosts by methods known in the art, e.g., transfection, electroporation, microinjection, transduction, cell fusion, DEAE dextran, calcium phosphate precipitation, lipofection (lysosome fusion), use of a gene gun, or a DNA vector transporter (see, e.g., Wu et al., 1992, J. Biol. Chem. 267:963–967; Wu and Wu, 1988, J. Biol. Chem. 263:14621–14624; Hartmut et al., Canadian Patent Application No. 2,012,311, filed Mar. 15, 1990).

Production of TRAP220, TRAP100, or Conserved Variants thereof, Fragments thereof, or Analogs or Derivatives thereof Moreover, the present invention extends to a method for producing a gene regulatory coactivator comprising an amino acid sequence of FIG. 2 (SEQ ID NO:2), conserved variants thereof, fragments thereof, or analogs or derivatives thereof, comprising the steps of:

a) culturing a unicellular host transformed or transfected with an expression vector described above under conditions that provide for expression of the isolated nucleic acid molecule comprising a DNA sequence of FIG. 1 (SEQ ID NO:1), degenerate variants thereof, fragments thereof, or analogs or derivatives thereof, operatively associated with a promoter, or an expression vector comprising an isolated nucleic acid molecule hybridizable under standard hybridization conditions to an isolated nucleic acid molecule comprising a DNA sequence of SEQ ID NO:1, degenerate variants thereof, fragments thereof, or analogs or derivatives thereof, operatively associated with a promoter; and b) recovering from the unicellular host, the culture medium or both, a nuclear hormone receptor coactivator comprising an amino acid sequence of FIG. 2 (SEQ ID NO:2), conserved variants thereof, fragments thereof, or analogs or derivatives thereof, produced from such expression.

In another embodiment, the present invention extends to a method for producing a gene regulatory coactivator comprising an amino acid sequence of FIG. 4 (SEQ ID NO:4), conserved variants thereof, fragments thereof, or analogs or derivatives thereof, comprising the steps of:

a) culturing a unicellular host transformed or transfected with an expression vector described above under conditions that provide for expression of the isolated nucleic acid molecule comprising a DNA sequence of FIG. 3 (SEQ ID NO:3), degenerate variants thereof, fragments thereof, or analogs or derivatives thereof, operatively associated with a promoter, or an expression vector comprising an isolated nucleic acid molecule hybridizable under standard hybridization conditions to an isolated nucleic acid molecule comprising a DNA sequence of FIG. 3 (SEQ ID NO:3), degenerate variants thereof, fragments thereof, or analogs or derivatives thereof, operatively associated with a promoter; and b) recovering from the unicellular host, the culture medium or both, a nuclear hormone receptor coactivator comprising an amino acid sequence of FIG. 4 (SEQ ID NO:4), conserved variants thereof, fragments thereof, or analogs or derivatives thereof, produced from such expression.

As explained above, the conditions which provide for expression of an isolated nucleic acid molecule of the present invention are dependent upon the expression vector and promoter used to transform or transfect a unicellular host of the invention. Since the conditions required regarding the promoter used are within the knowledge of one of ordinary skill in this art, conditions for specific promoters are not repeated here.

Moreover, collection of a nuclear hormone receptor coactivator comprising an amino acid sequence of FIG. 2 (SEQ ID NO:2), or FIG. 4 (SEQ ID NO:4). conserved variants thereof, fragments thereof, or analogs or derivatives thereof, produced pursuant to the method described above, is also within the knowledge of a skilled artisan, and is not described in detail here.

Antibodies to an Isolated and Homogenous TRAP220, TRAP100, Conserved Variants thereof, Fragments thereof, or Analogs or Derivatives thereof As explained above, the present invention further extends to antibodies having as an immunogen an isolated nuclear hormone receptor coactivator comprising an amino acid sequence of FIG. 2 (SEQ ID NO:2), FIG. 4 (SEQ ID NO:4), conserved variants thereof, fragments thereof, or analogs or derivatives thereof. Such antibodies include but are not limited to polyclonal, monoclonal, chimeric, single chain, Fab fragments, and an Fab expression library. The anti-TRAP220 and anti-TRAP100 antibodies of the invention may be cross reactive, e.g., they may recognize TRAP220 and TRAP100 from different species.

Various procedures known in the art may be used for the production of polyclonal antibodies to an isolated and homogenous nuclear hormone receptor coactivator, conserved variants thereof, fragments thereof, or analogs or derivatives thereof. For the production of antibody, various host animals can be immunized by injection with a TRAP220, TRAP100, conserved variants thereof, fragments thereof, or analogs or derivatives thereof. Such animals include but are not limited to rabbits, mice, rats, sheep, goats, etc. Furthermore, a nuclear hormone receptor protein comprising an amino acid sequence of FIG. 2 (SEQ ID NO:2), FIG. 4 (SEQ ID NO:4), conserved variants thereof, fragments thereof, or analogs or derivatives thereof, may be conjugated to an immunogenic carrier, e.g., bovine serum albumin (BSA) or keyhole limpet hemocyanin (KLH). Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and *Corynebacterium parvum*. In a preferred embodiment, derivatives of TRAP220 and TRAP100 in the form of fusion proteins comprising sequences of TRAP 220 or 100, and glutathione-S-transferase (GST), are injected into rabbits which produce polyclonal anti-TRAP220 and anti-TRAP100. These antibodies are then collected from the rabbits and used as described infra.

For preparation of monoclonal antibodies against TRAP220, TRAP100, conserved variants thereof, fragments thereof, or analogs or derivatives thereof, any technique that provides for the production of antibody molecules by continuous cell lines in culture may be used. These include but are not limited to the hybridoma technique originally developed by Kohler and Milstein [*Nature* 256:495–497 (1975)], as well as the trioma technique, the human B-cell hybridoma technique [Kozbor et al., *Immunology Today* 4:72 1983); Cote et al., *Proc. Natl. Acad. Sci. U.S.A.* 80:2026–2030 (1983)], and the EBV-hybridoma technique to produce human monoclonal antibodies [Cole et al., in *Monoclonal Antibodies and Cancer Therapy*, Alan R. Liss, Inc., pp. 77–96 (1985)]. In an additional embodiment of the invention, monoclonal antibodies can be produced in germ-free animals utilizing recent technology [PCT/US90/02545]. In fact, according to the invention, techniques developed for the production of "chimeric antibodies" [Morrison et al., *J. Bacteriol.* 159:870 (1984); Neuberger et al., *Nature* 312:604–608 (1984); Takeda et al., *Nature* 314:452–454 (1985)] by splicing the genes from a mouse antibody molecule specific for an TRAP220, TRAP100, conserved variants thereof, fragments thereof, or analogs or derivatives thereof, together with a fragment of a human antibody molecule of appropriate biological activity can be used; such antibodies are within the scope of this invention.

According to the invention, techniques described for the production of single chain antibodies [U.S. Pat. Nos. 5,476, 786 and 5,132,405 to Huston; U.S. Pat. No. 4,946,778] can be adapted to produce single chain antibodies specific for isolated TRAP220, TRAP100, conserved variants thereof, fragments thereof, or analogs or derivatives thereof. An additional embodiment of the invention utilizes the techniques described for the construction of Fab expression libraries [Huse et al., *Science* 246:1275–1281 (1989)] to allow rapid and easy identification of monoclonal Fab fragments with the desired specificity for TRAP220, TRAP100. conserved variants thereof, fragments thereof, or analogs or derivatives thereof.

Antibody fragments which contain the idiotype of the antibody molecule can be generated by known techniques. For example, such fragments include but are not limited to: the $F(ab')_2$ fragment which can be produced by pepsin digestion of the antibody molecule; the Fab' fragments which can be generated by reducing the disulfide bridges of the $F(ab')_2$ fragment, and the Fab fragments which can be generated by treating the antibody molecule with papain and a reducing agent.

In the production of antibodies, screening for the desired antibody can be accomplished by techniques known in the art, e.g., radioirnmunoassay, ELISA (enzyme-linked immunosorbant assay), "sandwich" immunoassays, immunoradiometric assays, gel diffusion precipitin reactions, immunodiffusion assays, in situ immunoassays (using colloidal gold, enzyme or radioisotope labels, for example), western blots, precipitation reactions, agglutination assays (e.g., gel agglutination assays, hemagglutination assays), complement fixation assays, immunofluorescence assays, protein A assays, and immunoelectrophoresis assays, etc. In one embodiment, antibody binding is detected by detecting a label on the primary antibody. In another embodiment, the primary antibody is detected by detecting binding of a secondary antibody or reagent to the primary antibody. In a further embodiment, the secondary antibody is labeled. Many means are known in the art for detecting binding in an immunoassay and are within the scope of the present invention. For example, to select antibodies which recognize a specific epitope of an isolated TRAP220, TRAP100, conserved variants thereof, fragments thereof, or analogs or derivatives thereof, one may assay generated hybridomas for a product which binds to a fragment of an isolated TRAP220 or TRAP100, conserved variants thereof, fragments thereof, or analogs or derivatives thereof containing such epitope.

The foregoing antibodies can be used in methods known in the art relating to the localization and activity of TRAP220, TRAP100, conserved variants thereof, fragments thereof, or analogs or derivatives thereof, e.g., for Western blotting, imaging TRAP220 or TRAP100 in situ, measuring levels thereof in appropriate physiological samples, etc. using any of the detection techniques mentioned above or known in the art.

Detectably Labeled Antibodies of to TRAP220, TRAP100, Conserved Variants thereof, Fragments thereof, or Analogs or Derivatives thereof Moreover, the present invention extends to antibodies described above, detectably labeled. Suitable detectable labels include enzymes, radioactive isotopes, fluorophores (e.g., fluorescene isothiocyanate (FITC), phycoerythrin (PE), Texas red (TR), rhodamine, free or chelated lanthanide series salts, especially $Eu^{3+}$, to name a few fluorophores), chromophores, radioisotopes, chelating agents, dyes, colloidal gold, latex particles, ligands (e.g., biotin), and chemiluminescent agents. When a control marker is employed, the same or different labels may be used for the receptor and control marker.

In the instance where the detectable label is radioactive, isotopes such as $^3H$, $^{14}C$, $^{32}P$, $^{35}S$, $^{36}Cl$, $^{51}Cr$, $^{57}Co$, $^{58}Co$, $^{59}Fe$, $^{90}Y$, $^{125}I$, $^{131}I$, and $^{186}Re$ are used, and known currently available counting procedures may be utilized. In the instance where the label is an enzyme, detection may be accomplished by any of the presently utilized colorimetric, spectrophotometric, fluorospectrophotometric, amperometric or gasometric techniques known in the art.

Direct labels are one example of labels which can be used according to the present invention. A direct label has been defined as an entity, which in its natural state, is readily visible, either to the naked eye, or with the aid of an optical filter and/or applied stimulation, e.g. U.V. light to promote fluorescence. Among examples of colored labels, which can be used according to the present invention, include metallic sol particles, for example, gold sol particles such as those described by Leuvering (U.S. Pat. No. 4,313,734); dye sole particles such as described by Gribnau et al. (U.S. Pat. No. 4,373,932) and May et al. (WO 88/08534); dyed latex such as described by May, supra, Snyder (EP-A 0 280 559 and 0 281 327); or dyes encapsulated in liposomes as described by Campbell et al. (U.S. Pat. No. 4,703,017). Other direct labels include a radionucleotide, a fluorescent moiety or a luminescent moiety. In addition to these direct labeling devices, indirect labels comprising enzymes can also be used according to the present invention. Various types of enzyme linked immunoassays are well known in the art, for example, alkaline phosphatase and horseradish peroxidase, lysozyme, glucose-6-phosphate dehydrogenase, lactate dehydrogenase, urease, these and others have been discussed in detail by Eva Engvall in Enzyme Immunoassay ELISA and EMIT in Methods in Enzymology, 70. 419–439, 1980 and in U.S. Pat. No. 4,857,453.

Other labels for use in the invention include magnetic beads or magnetic resonance imaging labels.

Isolated and Homogenous Nuclear Hormone Receptor Coactivators, Conserved Variants thereof, Fragments thereof, or Analogs or Derivatives thereof As explained above, the present invention extends to an isolated and homogenous nuclear hormone receptor coactivator comprising an amino acid sequence of FIG. 2 (SEQ ID NO:2), FIG. 4 (SEQ ID NO:4), conserved variants thereof, fragments thereof, or analogs or derivatives thereof. In particular, isolated and homogenous nuclear hormone receptors of the present invention comprise TRAP220, TRAP100, conserved variants thereof, fragments thereof, or analogs or derivatives thereof. As used herein, the term "homogenous" indicates that in its isolated state, a nuclear hormone receptor coactivator of the invention is uniform and does not contain substantial amounts of other materials. Consequently, for purposes of the instant Application, TRAP220 or TRAP100, or conserved variants thereof, fragments thereof, or analogs or derivatives thereof isolated from other compositions in a discrete band within a separating material such as agarose or acrylamide, is not homogenous in that it contains the separating material. If the nuclear hormone receptor, conserved variant thereof, fragment thereof, or analog or derivative thereof is separated from the separating material, such as in an electroelution protocol, and then collected, then for purposes of the instant Application the nuclear hormone receptor coactivator, conserved variants thereof, fragments thereof, or analogs or derivatives thereof, is isolated and homogenous.

Furthermore, the present invention extends to conserved variants, fragments, analogs and derivatives of TRAP220 and TRAP100, comprising amino acid sequences of SEQ ID NO:2 and SEQ ID NO:4 respectively. Derivatives can be made by altering encoding nucleic acid sequences by substitutions, additions or deletions that provide for functionally equivalent molecules. Preferably, derivatives are made that have enhanced or increased functional activity relative to native TRAP220 or TRAP100. Methods of altering the encoding nucleic acid sequences, such as site directed mutagenesis are readily apparent to the skilled artisan.

With the use of such techniques, one of ordinary skill in the art can create an analog or derivative of an isolated nucleic acid molecule comprising a DNA sequence of FIG. 1 (SEQ ID NO:1), or FIG. 3 (SEQ ID NO:3), which can then be expressed to produce an analog or derivative of TRAP220 or TRAP 100.

The nomenclature used to define the polypeptides is that specified by Schroder & Lubke, "The Peptides", Academic Press (1965), wherein in accordance with conventional representation the amino group at the N-terminal appears to the left and the carboxyl group at the C-terminal to the right. $NH_2$ refers to the amide group present at the carboxy terminus when written at the right of a polypeptide sequence.

Accordingly, conserved variants of TRAP220 and TRAP100, displaying substantially equivalent activity to TRAP220 and TRAP100, are likewise contemplated for use in the present invention. These modifications can be obtained through peptide synthesis utilizing the appropriate starting material.

In keeping with standard polypeptide nomenclature, J. Biol. Chem., 243:3552–59 (1969), abbreviations for amino acid residues are shown in the following Table of Correspondence:

| TABLE OF CORRESPONDENCE | | |
|---|---|---|
| SYMBOL | | |
| 1-Letter | 3-Letter | AMINO ACID |
| Y | Tyr | tyrosine |
| G | Gly | glycine |
| F | Phe | phenylalanine |
| M | Met | methionine |
| A | Ala | alanine |
| S | Ser | serine |
| I | Ile | isoleucine |
| L | Leu | leucine |
| T | Thr | threonine |
| V | Val | valine |
| P | Pro | proline |
| K | Lys | lysine |
| H | His | histidine |
| Q | Gln | glutamine |
| E | Glu | glutamic acid |
| W | Trp | tryptophan |
| R | Arg | arginine |
| D | Asp | aspartic acid |
| N | Asn | asparagine |
| C | Cys | cysteine |

It should be noted that all amino-acid residue sequences are represented herein by formulae whose left and right orientation is in the conventional direction of amino-terminus to carboxy-terminus. Furthermore, it should be noted that a dash at the beginning or end of an amino acid residue sequence indicates a peptide bond to a further sequence of one or more amino-acid residues. The above Table is presented to correlate the three-letter and one-letter notations which may appear alternately herein.

Hence, an amino acid in TRAP220 or TRAP100 can be changed in a non-conservative manner (i.e., by changing an amino acid belonging to a grouping of amino acids having a particular size or characteristic to an amino acid belonging to another grouping) or in a conservative manner (i.e., by changing an amino acid belonging to a grouping of amino acids having a particular size or characteristic to an amino acid belonging to the same grouping). Such a conservative change generally leads to less change in the structure and function of the resulting polypeptide. The present invention should be considered to include analogs whose sequences contain conservative changes which do not significantly alter the activity or binding characteristics of the resulting polypeptide.

The following is one example of various groupings of amino acids:
Amino Acids with Nonpolar R Groups
Alanine
Valine
Leucine
Isoleucine
Proline
Phenylalanine
Tryptophan
Methionine
Amino Acids with Uncharged Polar R Groups
Glycine
Serine
Threonine
Cysteine
Tyrosine
Asparagine
Glutamine
Amino Acids with Charged Polar R Groups (Negatively Charged at pH 6.0)
Aspartic acid
Glutamic acid
Basic Amino Acids (Positively Charged at pH 6.0)
Lysine
Arginine
Histidine (at pH 6.0)

Another grouping may be those amino acids with aromatic groups:
Phenylalanine
Tryptophan
Tyrosine Another grouping may be according to molecular weight (i.e., size of R groups):

| | |
|---|---|
| Glycine | 75 |
| Alanine | 89 |
| Serine | 105 |
| Proline | 115 |
| Valine | 117 |
| Threonine | 119 |
| Cysteine | 121 |
| Leucine | 131 |
| Asparagine | 132 |
| Aspartic acid | 133 |
| Glutamine | 146 |
| Lysine | 146 |
| Glutamic acid | 147 |
| Methionine | 149 |
| Histidine (at pH 6.0) | 155 |
| Phenylalanine | 165 |
| Arginine | 174 |
| Tyrosine | 181 |
| Tryptophan | 204 |

Particularly preferred substitutions are:
Gln for Arg or Lys; and
His for Lys or Arg.

Amino acid substitutions may also be introduced to substitute an amino acid with a particularly preferable property. For example, a Cys may be introduced to provide a potential site for disulfide bridges with another Cys, or with a carrier of the present invention. A His may be introduced as a particularly "catalytic" site (i.e., His can act as an acid or base and is the most common amino acid in biochemical catalysis). Pro may be introduced because of its particularly planar structure, which induces β-turns in the polypeptide's structure. Alternately, D-amino acids can be substituted for the L-amino acids at one or more positions.

The isolated nucleic acid sequence encoding TRAP220 or TRAP100, conserved variants thereof, fragments thereof, or analogs or derivatives thereof can be produced by various methods known in the art. The manipulations which result in their production can occur at the gene or protein level. For example, the cloned gene sequence can be modified by any of numerous strategies known in the art (Sambrook et al., 1989, supra). The sequence can be cleaved at appropriate sites with restriction endonuclease(s), followed by further enzymatic modification if desired, isolated, and ligated in vitro. In the production of the gene encoding a derivative or analog, care should be taken to ensure that the modified gene remains within the same translational reading frame as the native gene, uninterrupted by translational stop signals, in the gene region where the desired activity is encoded.

Additionally, a nucleic acid sequence can be mutated in vitro or in vivo, to create and/or destroy translation, initiation, and/or termination sequences, or to create variations in coding regions and/or form new restriction endonuclease sites or destroy preexisting ones, to facilitate further in vitro modification. Preferably, such mutations enhance the functional activity of the mutated gene product. Any technique for mutagenesis known in the art can be used, including but not limited to, in vitro site-directed mutagenesis (Hutchinson, C., et al., 1978, J. Biol. Chem. 253:6551; Zoller and Smith, 1984, DNA 3:479–488; Oliphant et al., 1986, Gene 44:177; Hutchinson et al., 1986, Proc. Natl. Acad. Sci. U.S.A. 83:710), use of "TAB" linkers (Pharmacia), etc. PCR techniques are preferred for site directed mutagenesis (see Higuchi, 1989, "Using PCR to Engineer DNA", in *PCR Technology: Principles and Applications for DNA Amplification,* H. Erlich, ed., Stockton Press, Chapter 6, pp. 61–70).

Moreover, the present invention also includes derivatives or analogs TRAP220 and TRAP100 produced from a chemical modification. Isolated and homogenous TRAP220 or TRAP100 may be derivatized by the attachment of one or more chemical moieties to the protein moiety. The chemically modified derivatives may be further formulated for intraarterial, intraperitoneal, intramuscular, subcutaneous, intravenous, oral, nasal, pulmonary, topical or other routes of administration. Chemical modification of TRAP220 and TRAP100 may provide additional advantages under certain circumstances, such as increasing the stability and circulation time of the chemically modified TRAP220 and TRAP100 and decreasing immunogenicity. See U.S. Pat. No. 4,179,337, Davis et al., issued Dec. 18, 1979. For a review, see Abuchowski et al., in *Enzymes as Drugs* (J. S. Holcerberg and J. Roberts, eds. pp. 367–383 (1981)). A review article describing protein modification and fusion proteins is Francis, 1992, *Focus on Growth Factors* 3:4–10, Mediscript: Mountview Court, Friern Barnet Lane, London N20, OLD, UK.

Chemical Moieties For Derivatization. The chemical moieties suitable for derivatization may be selected from among water soluble polymers. The polymer selected should be water soluble so that a TRAP220 or TRAP 100 analog or derivative does not precipitate in an aqueous environment, such as a physiological environment. Preferably, for therapeutic use of the end-product preparation, the polymer will be pharmaceutically acceptable. One skilled in the art will be able to select the desired polymer based on such considerations as whether the polymer/component conjugate will be used therapeutically, and if so, the desired dosage, circulation time, resistance to proteolysis, and other considerations. For TRAP220 and TRAP100, these may be ascertained using the assays provided herein.

The water soluble polymer may be selected from the group consisting of, for example, polyethylene glycol, copolymers of ethylene glycol/propylene glycol, carboxymethylcellulose. dextran, polyvinyl alcohol, polyvinyl pyrrolidone, poly-1,3-dioxolane, poly-1,3,6-trioxane, ethylene/maleic anhydride copolymer, polyaminoacids (either homopolymers or random copolymers), and dextran or poly(n-vinyl pyrrolidone)polyethylene glycol, polypropylene glycol homopolymers, polypropylene oxide/ethylene oxide co-polymers, polyoxyethylated polyols and polyvinyl alcohol. Polyethylene glycol propionaldenhyde may have advantages in manufacturing due to its stability in water.

The polymer may be of any molecular weight, and may be branched or unbranched. For polyethylene glycol, the preferred molecular weight is between about 2 kDa and about 100 kDa (the term "about" indicating that in preparations of polyethylene glycol, some molecules will weigh more, some less, than the stated molecular weight) for ease in handling and manufacturing. Other sizes may be used, depending on the desired therapeutic profile (e.g., the duration of sustained release desired, the effects, if any on biological activity, the ease in handling, the degree or lack of antigenicity and other known effects of the polyethylene glycol to a therapeutic protein or analog).

The number of polymer molecules so attached to TRAP220 or TRAP100 may vary, and one skilled in the art will be able to ascertain the effect on function. One may mono-derivatize, or may provide for a di-, tri-, tetra- or some combination of derivatization, with the same or different chemical moieties (e.g., polymers, such as different weights of polyethylene glycols). The proportion of polymer molecules to TRAP220 or TRAP100 will vary, as will their concentrations in the reaction mixture. In general, the optimum ratio (in terms of efficiency of reaction in that there is no excess unreacted component or components and polymer) will be determined by factors such as the desired degree of derivatization (e.g., mono, di-, tri-, etc.), the molecular weight of the polymer selected, whether the polymer is branched or unbranched, and the reaction conditions.

The polyethylene glycol molecules (or other chemical moieties) should be attached to TRAP220 or TRAP100 with consideration of effects on functional or antigenic domains of TRAP220 or TRAP100. There are a number of attachment methods available to those skilled in the art, e.g., EP 0 401 384 herein incorporated by reference (coupling PEG to G-CSF), see also Malik et al., 1992, Exp. Hematol. 20:1028–1035 (reporting pegylation of GM-CSF using tresyl chloride). For example, polyethylene glycol may be covalently bound through amino acid residues via a reactive group, such as, a free amino or carboxyl group. Reactive groups are those to which an activated polyethylene glycol molecule may be bound. The amino acid residues having a free amino group include lysine residues and the N-terminal amino acid residues; those having a free carboxyl group include aspartic acid residues glutamic acid residues and the C-terminal amino acid residue. Sulfhydryl groups may also be used as a reactive group for attaching the polyethylene glycol molecule(s). Preferred for therapeutic purposes is attachment at an amino group, such as attachment at the N-terminus or lysine group.

One may specifically desire N-terminally chemically modified TRAP220 or TRAP100. Using polyethylene glycol as an illustration of the present compositions, one may select from a variety of polyethylene glycol molecules (by molecular weight, branching, etc.), the proportion of polyethylene glycol molecules to TRAP220, or TRAP100 molecules in the reaction mix, the type of pegylation reaction to be performed, and the method of obtaining the selected N-terminally pegylated protein. The method of obtaining the N-terminally pegylated preparation (i.e., separating this moiety from other monopegylated moieties if necessary) may be by purification of the N-terminally pegylated material from a population of pegylated protein molecules. Selective N-terminal chemically modification may be accomplished by reductive alkylation which exploits differential reactivity of different types of primary amino groups (lysine versus the N-terminal) available for derivatization of TRAP220 and TRAP100. Under the appropriate reaction conditions, substantially selective derivatization of TRAP220 and TRAP100 at the N-terminus with a carbonyl group containing polymer is achieved. For example, one may selectively N-terminally pegylate TRAP220 or TRAP100 by performing the reaction at pH which allows one to take advantage of the $pK_a$ differences between the e-amino groups of the lysine residues and that of the a-amino group of the N-terminal residue of TRAP220 or TRAP100. By such selective derivatization, attachment of a water soluble polymer to TRAP220 or TRAP100 is controlled: the conjugation with the polymer takes place predominantly at the N-terminus and no significant modification of other reactive groups, such as the lysine side chain amino groups, occurs. Using reductive alkylation, the water soluble polymer may be of the type described above, and should have a single reactive aldehyde for coupling to TRAP220 or TRAP100. Polyethylene glycol proprionaldehyde, containing a single reactive aldehyde, may be used.

Fusion Proteins

Another example of an analog or derivative of TRAP220 or TRAP100, which is encompassed by the present invention, is a TRAP220 or TRAP100 fusion protein comprising an amino acid sequence of FIG. 2 (SEQ ID NO:2), FIG. 4 (SEQ ID NO:4), conserved variants thereof, fragments thereof, or analogs or derivatives thereof, a TRAP220 or TRAP100 fusion protein comprises at least a functionally active portion of a non-TRAP220 or TRAP100 protein joined via a peptide bond to at least a functionally active portion of an TRAP220 or TRAP100. The non-TRAP220 or TRAP100 sequences can be amino- or carboxy-terminal to the TRAP220 or TRAP100 sequences. More preferably, for stable expression of a proteolytically inactive TRAP220 or TRAP100 fusion protein, the portion of the non-TRAP220 or TRAP100 fusion protein is joined via a peptide bond to the amino terminus of the TRAP220 or TRAP100 portion, a recombinant DNA molecule encoding such a fusion protein comprises a sequence encoding at least a functionally active portion of a non-TRAP220 or TRAP100 protein joined in-frame to the TRAP220 or TRAP100 coding sequence, and preferably encodes a cleavage site for a specific protease, e.g., thrombin or Factor Xa, preferably at the TRAP220-non-TRAP220, or TRAP100-non-TRAP100 juncture. In a specific embodiment, the fusion protein is expressed in *Escherichia coli*. Examples of fusion proteins described infra include GST-TRAP220 and GST-TRAP100 fusion proteins.

Assay System for Screening Drugs and Other Agents for an Ability to Mimic or Antagonize a Corresponding Hormone Furthermore, the present invention extends to an assay system for screening potential drugs and other agents for ability to mimic or antagonize the function of corresponding hormones. Such a system comprises:

a) culturing an observable cellular test colony incubated with the potential drug or agent, wherein the cells of the cellular test colony contain a nuclear hormone receptor coactivator, conserved variants thereof, fragments thereof, or analogs or derivatives thereof, and a nuclear hormone receptor, which modulates the expression of a specific gene;

b) harvesting a cellular extract from the cellular test colony; and c) examining the extract to determine whether the expression of the gene was modulated relative to a standard, wherein such modulation is indicative of the ability of the potential drug or agent to mimic or antagonize the function of the corresponding hormone that binds to the nuclear hormone receptor.

The present invention further extends to an assay system as described, wherein the cells of the cellular test colony further comprise the corresponding hormone. If the nuclear hormone receptor and its corresponding hormone function to increase expression of the gene, and incubation of the potential drug or therapeutic agent along with the corresponding hormone results in decreased expression of the gene relative to expression in a standard, it is indicative that the potential drug or agent is an antagonist of the corresponding hormone.

In constrast, if incubation of the potential drug with the receptor in the absence of the corresponding hormone increases expression of the gene, the potential drug or agent may have applications as a mimic of the corresponding hormone.

Likewise, if the nuclear hormone receptor and its corresponding hormone function to repress expression of the gene, and incubation with the potential drug or therapeutic agent along with the corresponding hormone results in expression of the gene, the potential drug or agent may be considered an antagonist of the corresponding hormone. In constrast, if incubation with the potential drug in the absence of the corresponding hormone results in repression of expression the gene, the potential drug or agent may have applications as a mimic of the corresponding hormone.

Examples of coactivators having applications in an assay system of the present invention include but are not limited to TRAP220 comprising an amino acid sequence of FIG. 2 (SEQ ID NO:2), conserved variants thereof, fragments thereof, or analogs or derivatives thereof, or TRAP100, comprising an amino acid sequence of FIG. 4 (SEQ ID NO:4), conserved variants thereof, fragments thereof, or analogs or derivatives thereof.

Furthermore, examples of nuclear hormone receptors and their corresponding hormones that have applications in an assay system for screening potential drugs and other agents for ability mimic or antagonize the function of a corresponding hormones include, but are not limited to α and β isoforms of thyroid hormone receptor (TR), having thyroid hormone as a corresponding hormone, vitamin D receptor (VDR) having vitamin D as a corresponding hormone, isoforms α, β, and γ of retinoic acid receptor having trans-retinoic acid or 9-cis retinoic acid as a corresponding hormone, 60 , β, and γ isoforms of retinoid X receptor (RXR), having retinoids (compounds related to retinoate, the carboxylate form of vitamin $A_1$) as a corresponding hormone, α and β isoforms of estrogen receptor (ER), having estradiol or estriol as a corresponding hormone, progesterone receptor having progesterone as a corresponding hormone, androgen receptor having testosterone as a corresponding hormone, glucocorticoid receptor having cortisol as a corresponding hormone, mineralcorticoid receptor (MR) having aldosterone as a corresponding hormone, and α and γ isoforms of peroxisome proliferation-activated receptor (PPAR) having respectively Wy14643 and 15-deoxy-$D^{12,14}$-prostaglandin J2 as corresponding hormones.

In addition, the present invention extends to a cell free assay system for screening drugs or other agents for ability to mimic or antagonize a corresponding hormone which binds to a nuclear hormone receptor. Such a system comprises incubating purified nuclear hormone receptor with purified nuclear hormone receptor coactivator comprising an amino acid sequence of SEQ ID NO:2, conserved variants thereof, fragments thereof, or analogs or derivatives thereof, or an amino acid sequence of SEQ ID NO:4, conserved variants thereof, fragments thereof, or analogs or derivatives thereof, corresponding hormone and the potential drug or agent. After incubation, a determination is made whether the potential drug or agent and coactivator have bound to the receptor. If the drug or agent has bound to the receptor, it is indicative that the potential drug or agent has a greater binding affinity for the receptor than does the hormone, indicating the drug or agent has potential as an antagonist or mimic of the corresponding hormone. Numerous methods are presently available to the skilled artisan to determine whether both the drug and the coactivator are bound to the receptor. For example, immunoassays utilizing antibodies of the invention, preferably detectably labeled can be used to detect binding. Furthermore, antibodies made against the drug or agent using procedures for making monoclonal or polyclonal antibodies as discussed above, preferably detectably labeled, have applications in this system of the invention. Furthermore, an example of a method for determining whether a nuclear hormone receptor is activated is set forth in the Example infra.

Furthermore, examples of nuclear hormone receptors and their corresponding hormones that have applications in an assay system for screening potential drugs and other agents for ability mimic or antagonize the function of a corresponding hormones include, but are not limited to α and β isoforms of thyroid hormone receptor (TR), having thyroid hormone as a corresponding hormone, vitamin D receptor (VDR) having vitamin D as a corresponding hormone, isoforms α, β, and γ of retinoic acid receptor having trans-retinoic acid or 9-cis retinoic acid as a corresponding hormone, α, β, and γ isoforms of retinoid X receptor (RXR), having retinoids (compounds related to retinoate, the carboxylate form of vitamin $A_1$) as a corresponding hormone, α and β isoforms of estrogen receptor (ER), having estradiol or estriol as a corresponding hormone, progesterone receptor having progesterone as a corresponding hormone, androgen receptor having testosterone as a corresponding hormone, glucocorticoid receptor having cortisol as a corresponding hormone, mineralcorticoid receptor (MR) having aldosterone as a corresponding hormone, and α and γ isoforms of peroxisome proliferation-activated receptor (PPAR) having respectively Wy14643 and 15-deoxy-$D^{12,14}$-prostaglandin J2 as corresponding hormones.

Assay for Ligands of Coactivators of the Invention

In another embodiment, the present invention extends to a method for determining ligands that bind to a nuclear hormone receptor coactivator, conserved variants thereof, fragments thereof, or analogs or derivatives thereof. Such a method comprises the steps of culturing a suspected ligand with a nuclear hormone receptor activator, conserved variants thereof, fragments thereof, or analogs or derivatives thereof, removing the nuclear hormone receptor coactivator from the culture, and then determining whether the suspected ligand is bound to the nuclear hormone receptor coactivator. To a skilled artisan, many protocols are available for performing this method of the invention. For example, a nuclear hormone receptor coactivator, conserved variants thereof, fragments thereof or analogs or derivatives thereof can be immobilized onto a membrane, such as Polyvinylidenedifluoride (PVDF) or nitrocellulose. The membrane can then be cultured with the potential ligand, and then probed with a detectably labeled material which specifically binds to the ligand, such as an antibody having the ligand as an immunogen. In another example, the nuclear hormone receptor coactivator of the invention is immobilized onto beads, which are then placed into a column. A composition comprising a suspected ligand is then passed through the column so that the suspected ligand can contact the nuclear hormone receptor coactivator. The nuclear hormone receptor coactivator can then be removed from the bead, and assayed to determine whether the suspected ligand is bound thereto.

Alternatively, one can readily immobilize a suspected ligand onto a substrate, such as PVDF or nitrocellulose. and then probe the substrate with a nuclear hormone receptor coactivator, conserved variants thereof, fragments thereof, or analogs or derivatives thereof, optionally detectably labeled, to determine whether the nuclear hormone receptor coactivator binds to the potential ligand.

Numerous other procedures that are well understood by the skilled artisan having applications in determining a ligand of a coactivator, and are encompassed by the present invention.

Method for Screening Drugs for Ability to Mimic or Antagonize Nuclear Hormone Receptor Coactivators The present invention further extends to a method for screening drugs and other agents for ability mimic or antagonize the function of a nuclear hormone receptor coactivator of the invention. It is contemplated that such potential drugs can be used to modulate the activation of nuclear hormone receptors, and consequently modulate the expression of genes controlled by nuclear hormone receptors. Hence, the present invention extends to a method for screening drugs and other agents for ability to mimic or antagonize the function of a nuclear hormone receptor coactivator of the invention, comprising the steps of:
 a) culturing an observable cellular test colony incubated with the potential drug or agent, wherein the cells of the cellular test colony contain a nuclear hormone receptor which can modulate the expression of a specific gene, and a corresponding hormone which binds to the nuclear hormone receptor;
 b) harvesting a cellular extract from the cellular test colony; and
 c) examining the extract to determine whether the expression of the specific gene was modulated relative to expression of the specific gene in a standard, wherein the modulation of expression of the specific gene is indicative of the ability of the drug or agent to mimic or antagonize the nuclear hormone receptor coactivator.

In another embodiment, the present invention extends to the method for screening drugs or other agents for ability to mimic or antagonize the function of a nuclear hormone receptor coactivator as described above, wherein the cells of the test colony further comprise a corresponding hormone to the nuclear hormone receptor.

More specifically, if the nuclear hormone receptor, corresponding hormone, and coactivator function to increase expression of the gene, and incubation of the potential drug or therapeutic agent with the nuclear hormone receptor, its corresponding hormone, and coactivator results in decreased expression of the gene relative to expression in a standard, and the effects are unrelated to effects on corresponding hormone-receptor interactions, the potential drug or agent may be considered an antagonist of the nuclear hormone receptor coactivator. In constrast, if incubation of the potential drug or agent with the nuclear hormone receptor, and its corresponding hormone in the absence of coactivator results in increased levels of expression of the gene relative to a standard, the potential drug or agent may have applications as a mimic of the the nuclear hormone receptor coactivator.

Likewise, if the nuclear hormone receptor, corresponding hormone, and coactivator function to repress expression of the gene, and incubation with the potential drug or therapeutic agent with the nuclear hormone receptor and coactivator results in expression of the gene, and the effects can be shown to be unrelated to effects on hormone-receptor interactions, the potential drug or agent may be considered an antagonist of the nuclear hormone receptor coactivator. In constrast, if incubation of the potential drug with the receptor and corresponding hormone in the absnece of the coactivator results in repression of expression of the gene, the potential drug or agent may have applications as a mimic of the the nuclear receptor coactivator.

Per the above, the potential drugs or agents may be considered as antagonists of, or have applications as a mimic of the nuclear receptor coactivator if the effects can also be shown to be unrelated to effects on corresponding hormone-nuclear hormone receptor interactions i.e., the potential drug or agent is not a conventional hormone antagonist or mimic. In these cases, the action of the potential drug or agent as a coactivator mimic or antagonist may involve effects on interactions between receptor and coactivator or on interactions between coactivator and components of the general transcription machinery, or on interactions between various TRAPS in the coactivator complex. The potential drug or agent of the invention has applications in interacting with the nuclear hormone receptor, other coactivators, or the generaly transcription machinery, thus manifesting their effects as antagonist or mimics of coactivator function.

Examples of nuclear hormone receptors and their corresponding hormones that have applications in an assay system for screening potential drugs and other agents for ability to mimic or antagonize the functions of a corresponding hormone include, but are not limited to α and β isoforms of thyroid hormone receptor (TR), having thyroid hormone as a corresponding hormone, vitamin D receptor (VDR) having vitamin D as a corresponding hormone, isoforms α, β, and γ of retinoic acid receptor (RAR) having trans-retinoic acid or 9-cis retinoic acid as a corresponding hormone, α, β, and γ isoforms of retinoid X receptor (RXR), having retinoids (compounds related to retinoate, the carboxylate form of vitamin $A_1$) as a corresponding hormone, α and β isoforms of estrogen receptor (ER), having estradiol or estriol as a corresponding hormone, progesterone receptor (PR) having progesterone as a corresponding hormone, androgen receptor (AR) having testosterone as a corresponding hormone, glucocorticoid receptor (GR) having cortisol as a corresponding hormone, mineralcorticoid receptor (MR) having aldosterone as a corresponding hormone, and α and γ isoforms of peroxisome proliferation-activated receptor (PPAR) having respectively Wy14643 and 15-deoxy-$D^{12,14}$-prostaglandin J2 as corresponding hormones.

Furthermore, examples of coactivators having applications in an assay system of the present invention include, but are not limited to TRAP220 or TRAP100, conserved variants thereof, fragments thereof, or analogs or derivatives thereof.

Pharmaceutical Compositions of Modulating Expression of Genes

As explained above, the present invention extends to a pharmaceutical composition for modulating the activity of a nuclear hormone receptor comprising a nuclear hormone receptor coactivator, conserved variants thereof, fragments thereof or analogs or derivatives thereof, and a pharmaceutically acceptable carrier.

Furthermore, the present invention extends to a pharmaceutical composition for modulating gene expression comprising a ligand of a nuclear receptor coactivator comprising an amino acid sequence of FIG. 2 (SEQ ID NO:2), FIG. 4 (SEQ ID NO:4), conserved variants thereof, fragments thereof, or analogs or derivatives thereof, and a pharmaceutically acceptable carrier.

In another embodiment, ligands of coactivators of the present invention have applications as drugs or agents within a pharmaceutical composition. In particular, some of the ligands bind a coactivator in a manner that prevents the binding of a complex comprising the coactivator from binding to a particular nuclear hormone receptor. As a result, the function of the receptor is interrupted, resulting in a modulation of expression of relative to expression of the specific gene in a standard. Alternatively, some ligands of a coactivator of the invention bind to the coactivator in a manner that increases the affinity of the complex for a nuclear hormone receptor. Consequently, the function of the receptor is increased relative to a standard, which modulates the expression of the specific gene relative to expression of the specific gene in a standard.

In yet another embodiment, ligands of a coactivator of the invention have applications in preventing the formation of a coactivator complex. As described above, a coactivator complex comprising numerous coactivator proteins binds to a nuclear hormone receptor, and is involved in activating the receptor, which in turn regulates the expression of a specific gene. However, if a ligand of a coactivator of the invention binds the coactivator in a manner that prevents its binding with other coactivators so that the complex is not formed, the nuclear hormone receptor can not be activated, and expression of the specific gene is modulated relative to expression of the specific gene in the standard.

The phrase "pharmaceutically acceptable" as used herein refers to molecular entities and compositions that are physiologically tolerable and do not typically produce an allergic or similar untoward reaction, such as gastric upset, dizziness and the like, when administered to a human.

Such pharmaceutical compositions may be for administration for injection, or for oral, pulmonary, nasal or other forms of administration. In general, comprehended by the invention are pharmaceutical compositions comprising effective amounts of a nuclear receptor hormone coactivator, conserved variants thereof, fragments thereof, or analogs or derivatives thereof, or a ligand of a nuclear hormone receptor coactivator, conserved variants thereof, fragments thereof, or analogs or derivatives thereof, together with pharmaceutically acceptable diluents, preservatives, solubilizers, emulsifiers, adjuvants and/or carriers. Such compositions include diluents of various buffer content (e.g., Tris-HCl, acetate, phosphate), pH and ionic strength; additives such as detergents and solubilizing agents (e.g., Tween 80, Polysorbate 80), anti-oxidants (e.g., ascorbic acid, sodium metabisulfite), preservatives (e.g., Thimersol, benzyl alcohol) and bulking substances (e.g., lactose, mannitol); incorporation of the material into particulate preparations of polymeric compounds such as polylactic acid, polyglycolic acid, etc. or into liposomes. Hyaluronic acid may also be used. Such compositions may influence the physical state, stability, rate of in vivo release, and rate of in vivo clearance of the present proteins and derivatives. See, e.g., Remington's Pharmaceutical Sciences, 18th Ed. (1990, Mack Publishing Co., Easton, Pa. 18042) pages 1435–1712 which are herein incorporated by reference. The compositions may be prepared in liquid form, or may be in dried powder, such as lyophilized form.

Oral Delivery

Contemplated for use herein are oral solid dosage forms, which are described generally in Remington's Pharmaceutical Sciences, 18th Ed. 1990 (Mack Publishing Co. Easton Pa. 18042) at Chapter 89, which is herein incorporated by reference. Solid dosage forms include tablets, capsules, pills, troches or lozenges, cachets or pellets. Also, liposomal or proteinoid encapsulation may be used to formulate the present compositions (as, for example, proteinoid microspheres reported in U.S. Pat. No. 4,925,673). Liposomal encapsulation may be used and the liposomes may be derivatized with various polymers (e.g., U.S. Pat. No. 5,013,556). A description of possible solid dosage forms for the therapeutic is given by Marshall, K. In: *Modern Pharmaceutics* Edited by G. S. Banker and C. T. Rhodes Chapter 10, 1979, herein incorporated by reference. In an embodiment of the invention, the formulation will generally include a nuclear hormone receptor comprising an amino acid sequence of SEQ ID NO:2, conserved variants thereof, fragments thereof, or analogs or derivatives thereof, or an amino acid sequence of SEQ ID NO:4, conserved variants thereof, fragments thereof, or analogs or derivatives thereof, and inert ingredients which allow for protection against the stomach environment, and release of the biologically active material in the intestine. In another embodiment of the invention, the formation will generally include a ligand of a nuclear hormone receptor coactivator comprising an amino acid sequence of SEQ ID NO:2, SEQ ID NO:4, conserved variants thereof, fragments thereof, or analogs or derivatives thereof, and inert ingredients which allow for protection against the stomach environment, and release of the biologically active material in the intestine.

Also specifically contemplated are oral dosage forms of a nuclear hormone receptor coactivator, conserved variants thereof, fragments thereof, or analogs or derivatives thereof, or a ligand thereof. The nuclear hormone receptor coactivator or ligand thereof may be chemically modified so that oral delivery is efficacious. Generally, the chemical modification contemplated is the attachment of at least one moiety to the nuclear hormone receptor coactivator, or ligand thereof of a pharmaceutical composition of the invention, where the moiety permits (a) inhibition of proteolysis; and (b) uptake into the blood stream from the stomach or intestine. Also desired is the increase in overall stability of a nuclear hormone receptor coactivator or a ligand thereof, and increase in circulation time in the body. Examples of such moieties include: polyethylene glycol, copolymers of ethylene glycol and propylene glycol, carboxymethyl cellulose, dextran, polyvinyl alcohol, polyvinyl pyrrolidone and polyproline. Abuchowski and Davis, 1981, "Soluble Polymer-Enzyme Adducts" In: *Enzymes as Drugs,* Hocenberg and Roberts, eds., Wiley-Interscience, New York, N.Y., pp. 367–383; Newmark, et al., 1982, J. Appl. Biochem. 4:185–189. Other polymers that could be used are poly-1,3-dioxolane and poly-1,3,6-tioxocane. Preferred for pharmaceutical usage, as indicated above, are polyethylene glycol moieties.

For a nuclear hormone receptor coactivator, or a ligand thereof, the location of release a pharmaceutical composition of the invention may be the stomach, the small intestine (the duodenum, the jejunum, or the ileum), or the large intestine. One skilled in the art has available formulations which will not dissolve in the stomach, yet will release the material in the duodenum or elsewhere in the intestine. Preferably, the release will avoid the deleterious effects of the stomach environment, either by protection of the the nuclear hormone receptor coactivator, or by release from the pharmaceutical composition beyond the stomach environment, such as in the intestine.

To ensure full gastric resistance, a coating impermeable to at least pH 5.0 is essential. Examples of the more common inert ingredients that are used as enteric coatings are cellulose acetate trimellitate (CAT), hydroxypropylmethylcellulose phthalate (HPMCP), HPMCP 50, HPMCP 55, polyvinyl acetate phthalate (PVAP), Eudragit L30D, Aquateric, cellulose acetate phthalate (CAP), Eudragit L, Eudragit S, and Shellac. These coatings may be used as mixed films.

A coating or mixture of coatings can also be used on tablets, which are not intended for protection against the stomach. This can include sugar coatings, or coatings which make the tablet easier to swallow. Capsules may consist of a hard shell (such as gelatin) for delivery of dry therapeutic i.e. powder; for liquid forms, a soft gelatin shell may be used. The shell material of cachets could be thick starch or other edible paper. For pills, lozenges, molded tablets or tablet triturates, moist massing techniques can be used.

The pharmaceutical composition can be included in the formulation as fine multi-particulates in the form of granules or pellets of particle size about 1 mm. The formulation of the pharmaceutical composition for capsule administration could also be as a powder, lightly compressed plugs or even as tablets. The pharmaceutical composition could be prepared by compression.

Colorants and flavoring agents may all be included. For example, a nuclear hormone receptor, conserved variants thereof, fragments thereof, or analogs or derivatives thereof, or a ligand of a nuclear hormone receptor coactivator, conserved variants thereof, fragments thereof, or analogs or derivatives thereof, may be formulated (such as by liposome or microsphere encapsulation) and then further contained within an edible product, such as a refrigerated beverage containing colorants and flavoring agents.

One may dilute or increase the volume of a pharmaceutical composition of the invention with an inert material. These diluents could include carbohydrates, especially mannitol, a-lactose, anhydrous lactose, cellulose, sucrose, modified dextrans and starch. Certain inorganic salts may be also be used as fillers including calcium triphosphate, magnesium carbonate and sodium chloride. Some commercially available diluents are Fast-Flo, Emdex, STA-Rx 1500, Emcompress and Avicell.

Disintegrants may be included in the formulation of a pharmaceutical composition of the invention into a solid dosage form. Materials used as disintegrates include but are not limited to starch, including the commercial disintegrant based on starch, "EXPLOTAB." Sodium starch glycolate, Amberlite, sodium carboxymethylcellulose, ultramylopectin, sodium alginate, gelatin, orange peel, acid carboxymethyl cellulose, natural sponge and bentonite may all be used. Another form of the disintegrants are the insoluble cationic exchange resins. Powdered gums may be used as disintegrants and as binders and these can include powdered gums such as agar, Karaya or tragacanth. Alginic acid and its sodium salt are also useful as disintegrants.

Binders may be used to hold a pharmaceutical composition of the invention together to form a hard tablet and include materials from natural products such as acacia, tragacanth, starch and gelatin. Others include methyl cellulose (MC), ethyl cellulose (EC) and carboxymethyl cellulose (CMC). Polyvinyl pyrrolidone (PVP) and hydroxypropylmethyl cellulose (HPMC) could both be used in alcoholic solutions to granulate the therapeutic.

An anti-frictional agent may be included in the formulation of a pharmaceutical composition of the invention to prevent sticking during the formulation process. Lubricants may be used as a layer between the pharmaceutical composition and the die wall, and these can include but are not limited to; stearic acid including its magnesium and calcium salts, polytetrafluoroethylene (PTFE), liquid paraffin, vegetable oils and waxes. Soluble lubricants may also be used such as sodium lauryl sulfate, magnesium lauryl sulfate, polyethylene glycol of various molecular weights, Carbowax 4000 and 6000.

Glidants that might improve the flow properties of a pharmaceutical composition of the invention during formulation and to aid rearrangement during compression might be added. The glidants may include starch, talc, pyrogenic silica and hydrated silicoaluminate.

To aid dissolution of a pharmaceutical composition of the invention into the aqueous environment a surfactant might be added as a wetting agent. Surfactants may include anionic detergents such as sodium lauryl sulfate, dioctyl sodium sulfosuccinate and dioctyl sodium sulfonate. Cationic detergents might be used and could include benzalkonium chloride or benzethomium chloride. The list of potential non-ionic detergents that could be included in the formulation as surfactants are lauromacrogol 400, polyoxyl 40 stearate, polyoxyethylene hydrogenated castor oil 10, 50 and 60, glycerol monostearate, polysorbate 40, 60, 65 and 80, sucrose fatty acid ester, methyl cellulose and carboxymethyl cellulose. These surfactants could be present in the formulation of a nuclear hormone receptor coactivator, conserved variants thereof, fragments thereof, or analogs or derivatives thereof, either alone or as a mixture in different ratios.

Additives which potentially enhance uptake of a nuclear hormone receptor coactivator are for instance the fatty acids oleic acid, linoleic acid and linolenic acid.

Controlled release oral formulation may be desirable,. a pharmaceutical composition of the invention could be incorporated into an inert matrix which permits release by either diffusion or leaching mechanisms, e.g., gums. Slowly degenerating matrices may also be incorporated into the formulation. Some enteric coatings also have a delayed release effect.

Another form of a controlled release of a pharmaceutical composition of the present invention is by a method based on the "OROS" therapeutic system (Alza Corp.), i.e. the pharmaceutical composition is enclosed in a semipermeable membrane which allows water to enter and push drug out through a single small opening due to osmotic effects.

Other coatings may be used for the formulation. These include a variety of sugars which could be applied in a coating pan. The therapeutic agent could also be given in a film coated tablet and the materials used in this instance are divided into 2 groups. The first are the nonenteric materials and include methyl cellulose, ethyl cellulose, hydroxyethyl cellulose, methylhydroxy-ethyl cellulose, hydroxypropyl cellulose, hydroxypropyl-methyl cellulose, sodium carboxymethyl cellulose, providone and the polyethylene glycols. The second group consists of the enteric materials that are commonly esters of phthalic acid.

A mix of materials might be used to provide the optimum film coating. Film coating may be carried out in a pan-coater or in a fluidized bed or by compression coating.

Pulmonary Delivery. Also contemplated herein is pulmonary delivery of a pharmaceutical composition comprising a nuclear hormone receptor coactivator, conserved variants thereof, fragments thereof, or analogs or derivatives thereof, or a ligand of a nuclear hormone receptor, conserved variants thereof, fragments thereof, or analogs or derivatives thereof, which is delivered to the lungs of a mammal while inhaling and traverses across the lung epithelial lining to the blood stream. Other reports of this include Adjei et al., 1990, Pharmaceutical Research, 7:565–569; Adjei et al., 1990, International Journal of Pharmaceutics, 63:135–144 (leuprolide acetate); Braquet et al., 1989, Journal of Cardiovascular Pharmacology, 13 (suppl. 5):143–146 (endothelin-1); Hubbard et al., 1989, Annals of Internal Medicine, Vol. III, pp. 206–212 (a1-antitrypsin); Smith et al., 1989, J. Clin. Invest. 84:1145–1146 (a-1-proteinase); Oswein et al., 1990, "Aerosolization of Proteins", Proceedings of Symposium on Respiratory Drug Delivery II, Keystone, Colo., March, (recombinant human growth hormone); Debs et al., 1988, J. Immunol. 140:3482–3488 (interferon-g and tumor necrosis factor alpha) and Platz et al., U.S. Pat. No. 5,284,656 (granulocyte colony stimulating factor), a method and composition for pulmonary delivery of drugs for systemic effect is described in U.S. Pat. No. 5,451,569, issued Sep. 19, 1995 to Wong et al.

Contemplated for use in the practice of this invention are a wide range of mechanical devices designed for pulmonary delivery of therapeutic products, including but not limited to nebulizers, metered dose inhalers, and powder inhalers, all of which are familiar to those skilled in the art.

Some specific examples of commercially available devices suitable for the practice of this invention are the "ULTRAVENT" nebulizer, manufactured by Mallinckrodt, Inc., St. Louis, Mo.; the "ACORN II" nebulizer, manufactured by Marquest Medical Products, Englewood, Colo.; the "VENTOLIN" metered dose inhaler, manufactured by Glaxo Inc., Research Triangle Park, N.C.; and the "SPINHALER" powder inhaler, manufactured by Fisons Corp., Bedford, Mass.

All such devices require the use of formulations suitable for the dispensing of a nuclear hormone receptor coactivator comprising an amino acid sequence of SEQ ID NO:2, SEQ ID NO:4, conserved variants thereof, fragments thereof, or analogs or derivatives thereof, or ligands thereof. Typically, each formulation is specific to the type of device employed and may involve the use of an appropriate propellant material, in addition to the usual diluents, adjuvants and/or carriers useful in therapy. Also, the use of liposomes, microcapsules or microspheres, inclusion complexes, or other types of carriers is contemplated. Chemically modified nuclear hormone receptor coactivator, or a ligand thereof may also be prepared in different formulations depending on the type of chemical modification or the type of device employed.

Formulations suitable for use with a nebulizer, either jet or ultrasonic, will typically comprise a nuclear hormone receptor coactivator or a ligand thereof, dissolved in water at a concentration of about 0.1 to 25 mg of biologically active molecule per mL of solution. The formulation may also include a buffer and a simple sugar (e.g., for protein stabilization and regulation of osmotic pressure). The nebulizer formulation may also contain a surfactant, to reduce or prevent surface induced aggregation of a nuclear hormone receptor coactivator caused by atomization of the solution in forming the aerosol.

Formulations for use with a metered-dose inhaler device will generally comprise a finely divided powder containing a nuclear hormone receptor coactivator, conserved variants thereof, fragments thereof, or analogs or derivatives thereof, or a ligand thereof, suspended in a propellant with the aid of a surfactant. The propellant may be any conventional material employed for this purpose, such as a chlorofluorocarbon, a hydrochlorofluorocarbon, a hydrofluorocarbon, or a hydrocarbon, including trichlorofluoromethane, dichlorodifluoromethane, dichlorotetrafluoroethanol, and 1,1,1,2-tetrafluoroethane, or combinations thereof. Suitable surfactants include sorbitan trioleate and soya lecithin. Oleic acid may also be useful as a surfactant.

Formulations for dispensing from a powder inhaler device will comprise a finely divided dry powder containing a nuclear hormone receptor coactivator, conserved variants thereof, fragments thereof, or analogs or derivatives thereof, or a ligand thereof, and may also include a bulking agent, such as lactose, sorbitol, sucrose, or mannitol in amounts which facilitate dispersal of the powder from the device, e.g., 50 to 90% by weight of the formulation. A nuclear hormone receptor coactivator, or a ligand of a nuclear hormone receptor of a pharmaceutical composition of the invention should most advantageously be prepared in particulate form with an average particle size of less than 10 mm (or microns), most preferably 0.5 to 5 mm, for most effective delivery to the distal lung.

Nasal Delivery. Nasal delivery of a pharmaceutical composition of the present invention is also contemplated. Nasal delivery allows the passage of a nuclear hormone receptor coactivator comprising an amino acid sequence of SEQ ID NO:2. SEQ ID NO:4, conserved variants thereof, fragments thereof, or analogs or derivatives thereof, or a ligand thereof, to the blood stream directly after administering the pharmaceutical composition to the nose, without the necessity for deposition of the product in the lung. Formulations for nasal delivery include those with dextran or cyclodextran.

Methods for Modulating Gene Expression

Pharmaceutical compositions discussed above have applications in methods for modulating gene expression in an animal. In an embodiment, the present invention naturally extends to a method for modulating gene expression, comprising administering a therapeutically effective amount of a pharmaceutical composition comprising a nuclear hormone receptor coactivator comprising an amino acid sequence of SEQ ID NO:2, SEQ ID NO:4, conserved variants thereof, fragments thereof, analogs or derivatives thereof, and a pharmaceutically acceptable carrier thereof, such that levels of the coactivator, conserved variants thereof, fragments thereof, or analogs or derivatives thereof, are sufficient to modulate the function of a nuclear hormone receptor. Hence, the expression of the gene is modulated relative to expression of the gene in a standard, i.e., either increased or decreased relative to expression of the gene in a standard.

The phrase "therapeutically effective amount" is used herein to mean an amount sufficient to increase of decrease expression of a particular gene by at least about 30 percent, more preferably by at least 50 percent, most preferably by at least 90 percent, as compared to a standard, or preferably compared to levels expression of the particular gene prior to administration of a pharmaceutical composition of the invention to an animal.

In another embodiment, the present invention extends to a method for modulating activity of a nuclear hormone receptor, comprising administering a pharmaceutical composition comprising a coactivator comprising an amino acid sequence of SEQ ID NO:2, or SEQ ID NO:4, conserved variants thereof, fragments thereof, or analogs or derivatives thereof, in an amount such that the coactivator, conserved variants thereof, fragments thereof, or analogs or derivatives thereof binds to the nuclear hormone receptor and prevents endogenous TRAP complexes, or distinct nuclear hormone receptor-binding coactivators from binding to the receptor, so that the function of the receptor is modulated relative to its function in a standard. In this way, there is an excess amount of a coactivator comprising the amino acid sequence of SEQ ID NO:2, SEQ ID NO:4, conserved variants thereof, fragments thereof, or analogs or derivatives thereof, which bind to the nuclear hormone receptor so that endogenous TRAP coactivator complexes, or other distinct nuclear hormone receptor-binding coactivators are unable to bind to the receptor. Hence, the receptor is not activated, and gene expression is modulated.

Dosages. For all of the above pharmaceutical compositions, as further studies are conducted, information will emerge regarding appropriate dosage levels for treatment of various conditions in various patients, and the ordinary skilled worker, considering the therapeutic context, age and general health of the recipient, will be able to ascertain proper dosing.

Examples of nuclear hormone receptors having applications in a method for modulating gene expression comprise an amino acid sequence of SEQ ID NO:2, conserved variants thereof, fragments thereof, or analogs or derivatives thereof, or an amino acid sequence of SEQ ID NO:4, conserved variants thereof, fragments thereof, or analogs or derivatives thereof.

Examples of coactivators having applications in such methods of the invention include coactivators comprising an amino acid sequence of FIG. 2 (SEQ ID NO:2), conserved variants thereof, fragments thereof, or analogs or derivatives thereof, or an amino acid sequence of FIG. 4 (SEQ ID NO:4), conserved variants thereof, fragments thereof, or analogs or derivatives thereof.

Furthermore, examples of nuclear hormone receptors having applications in a method for modulating activity of a nuclear hormone receptor, and hence gene expression include, but are not limited to α and β isoforms of thyroid hormone receptor (TR), having thyroid hormone as corresponding particular hormone, vitamin D receptor (VDR) having vitamin D as a corresponding hormone, isoforms α, β, and γ of retinoic acid receptor having trans-retinoic acid or 9-cis retinoic acid as a corresponding hormone, α, β, and γ isoforms of retinoid X receptor (RXR), having retinoids (compounds related to retinoate, the carboxylate form of vitamin $A_1$) as a corresponding hormone, α and β isoforms of estrogen receptor (ER), having estradiol or estriol as a corresponding hormone, progesterone receptor having progesterone as a corresponding hormone, androgen receptor having testosterone as a corresponding hormone, glucocorticoid receptor having cortisol as a corresponding hormone, mineralcorticoid receptor (MR) having aldosterone as a corresponding hormone, and α and β isoforms of peroxisome proliferation-activated receptor (PPAR) having respectively Wy14643 and 15-deoxy-$D^{12,14}$-prostaglandin J2 as corresponding hormones.

The present invention may be better understood by reference to the following non-limiting Examples, which are provided as exemplary of the invention. The following examples are presented in order to more fully illustrate the preferred embodiments of the invention. They should in no way be construed, however, as limiting the broad scope of the invention.

EXAMPLE

The TRAP220 Component of a Thyroid Hormone Receptor-associated Protein (TRAP) Coactivator Complex Interacts Directly with Nuclear Hormone Receptors in a Ligand-Dependent Fashion Most ligand-dependent nuclear hormone receptor-interacting proteins that represent established or candidate cofactors have been identified and/or cloned by biochemical interaction or yeast two hybrid assays (reviewed in 4,5). Coactivators thus identified include (i) members of the SRC family (SRC-1/NCoA-1, TIF-2/GRIP-1/NCoA-2 and PCIP/ACTR/RAC-3/AIB-1 reviewed in (4–6), (ii) the more general coactivators p300/CBP and the interacting coactivator PCAF (reviewed in 4–6) and (iii) a group of unrelated factors that include RIP140, TIF-1, Trip-1 and ARA70 (reviewed in 4–6) and the more recently-described PBP (8), TRIP230 (9) and p120 (10). Most of these factors show ligand-dependent receptor interactions that depend upon the integrity of the AF-2 domain; and demonstrations of AF-2-dependent coactivator functions have involved assays in living cells (yeast and mammalian) with ectopically expressed coactivators or micro-injected antibodies (reviewed in 4–6). Although mechanisms of action are unknown for most of these coactivactors, the presence of histone acetyltransferase activities in CBP/p300 (11), PCAF (12) and some members of the SRC family (13,14) suggest a role in chromatin structural modifications prior to formation of a preinitiation complex.

In another approach, thyroid hormone receptor-associated proteins (TRAPs) were isolated by affinity purification of an epitope-tagged thyroid hormone receptor from cells grown in the presence of a cognate ligand (7). The coactivator function of the TRAPs was demonstrated in a cell free system reconstituted with purified DNA templates and components of the general transcription machinery, indicating that they act more directly to facilitate preinitiation complex formation or function (7). More recent studies have shown that the general coactivators PC4 and PC2, but apparently not the TAFs, are required for activation by the TR-TRAP complex (unpublished observations). The present study reports the cloning and further characterization of individual TRAP components, which appear to play a broader role in nuclear hormone receptor function.

Materials and Methods cDNA Cloning and Northern Blot Analysis

An immunopurified TR-TRAP complex from ligand-treated α-2 cells (7) was subjected to SDS-PAGE and peptides derived from TRAP220 and TRAP100 were subjected to microsequence analysis. An EST clone (EST33696) containing a TRAP220 peptide was used to screen a Jurkat cDNA library (Stratagene). Positive clones were sequenced and ligated to construct the full-length TRAP220. The N-terminal sequence of TRAP100 matched that of a protein specified by human KIAA0130 gene cDNA (15) and gene-specific primers were used to PCR-amplify the N- and C-terminal halves of TRAP100 from α-2 cell-derived cDNA. The resulting fragments were ligated to create a full-length TRAP100 cDNA that was verified by DNA sequencing. a 0.7 kb cDNA encoding residues 405–644 of TRAP220 and a 1.5 kb cDNA encoding residues 1–489 of TRAP100 were used to probe a human multiple tissue Northern blot (Clontech).

Plasmid Constructions

All primer sequences used in subcloning in the Example are set forth below:

```
Primers for TRAP220 and receptors;

TRAP220/1
GCGGATCCCCTCTTATCCTAAATCTGATC                                                (SEQ ID NO:5)

GGAATTCATCGGGTGGTTCTTGGTGTTGC                                                (SEQ ID NO:6)

TRAP220/2
GATACGTCGACGATGGCCGGCAACACCAAGAA                                             (SEQ ID NO:7)

GATGCAGATCTTCTGGTGCTTTGGTTTCTCAG                                             (SEQ ID NO:8)

TRAP220 mutant c
CATGCCATGGATGGGGAGGACTTCAGCAAGGTG                                            (SEQ ID NO:9)

GCGGATCCTCACTGGTGCTTTGGTTTCTCAGGTG                                           (SEQ ID NO:10)

PPAR α
GGAATTCCATATGGTGGACACGGAAAGCCCAC                                             (SEQ ID NO:11)

GCGGATCCTCAGTACATGTCCCTGTAGATC                                               (SEQ ID NO:12)

VDR
GGAATTCCATATGGAGGCAATGGCGGCCAG                                               (SEQ ID NO:13)

GCGGATCCTCAGGAGATCTCATTGCCAAAC                                               (SEQ ID NO:14)

Erα (amino acid 302–595)
GGAATTCCATATGAAGAAGAACAGCCTGGCCTTGTCCC                                       (SEQ ID NO:15)

CGGGATCCTCAGACTGTGGCAGGGAAACCCTCTGC                                          (SEQ ID NO:16)

Primers for vectors used herein:

TRE-NX-up       CTAGCCAGGTCACAGCAGGTCAGC                                     (SEQ ID NO:17)

TRE-NX-down     TCGAGCTGACCTGCTGTGACCTGG                                     (SEQ ID NO:18)

5'G-Xho         GACTACTCGAGTCGCCCCGGGTGTTCCTGAA                              (SEQ ID NO:19)

3'G-Hind(290)   ATGCAAGCTTCGGGGATGAAGATGATAGGG                               (SEQ ID NO:20)

3'G-130-Hind    ATGCAAGCTTATGAGAGTGAATGATGATAGA                              (SEQ ID NO:21)

5VDRE/Nhe       CTAGCGAGCTCGGGTGAACGGGGCAGAGCTCGGGTGAACGGGGCAGAGCTCC         (SEQ ID NO:22)

3VDRE/Xho       TCGAGGGAGCTCTGCCCCCGTTCACCCGAGCTCTGCCCCCGTTCACCCGAGCTCG      (SEQ ID NO:23)

hVDRE-up        CGGGTGAACGGGGCAGAGCT                                         (SEQ ID NO:24)

hVDRE-down      CTGCCCCCGTTCACCCGAGCT                                        (SEQ ID NO:25)

TRE-Sac-up      CCAGGTCACAGCAGGTCAGGAGCT                                     (SEQ ID NO:26)

TRE-Sac-down    CCTGACCTGCTGTGACCTGGAGCT                                     (SEQ ID NO :27)

Primers for TRAP100

110M-Sal        GACTACGTCGACCCTCATGGACCCCCCGGGCAC                            (SEQ ID NO:28)

110N-Bam        TGCGGATCCGTCCAGGGGGAAGAGGCTGA                                (SEQ ID NO:29)
```

-continued

| | | |
|---|---|---|
| 110/1950 | GCCAGCTGGCAGGGCCACTG | (SEQ ID NO:30) |
| 110/1250 | CTCCGGGCGGAGCCACTGT | (SEQ ID NO:31) |
| 110/400 | CCTCCACTGGCTGCTGCGCT | (SEQ ID NO:32) |
| 110K-Sal | GACTACGTCGACCACCCTGCTGCACATGGGCGG | (SEQ ID NO:33) |
| 110L-Bam | TGCGGATCCGCCGCCCATGTGCAGCAGGGT | (SEQ ID NO:34) |
| 110I | CTGAAATCCTTCGCCCGGAA | (SEQ ID NO:35) |
| 110J | CCACTGCGGCCATGCCAAGC | (SEQ ID NO:36) |
| 110F-Bam | TGCGGATCCGGCCGGTTTGGTGCTTTCTT | (SEQ ID NO:37) |
| 110E-Sal | GACTACGTCGACCAAGACCGGCTTCCCCACTGT | (SEQ ID NO:38) |
| 110C-Bam | TGCGGATCCGGTGCCCTCGAGCAGGATCA | (SEQ ID NO:39) |
| 110A-Sal | GACTACGTCGACCATGAAGGTGGTCAACCTGAA | (SEQ ID NO:40) |
| 110E | CAAGACCGGCTTCCCCACTG | (SEQ ID NO:41) |
| 110F | GAGGCCGGTTTGGTGCTTTC | (SEQ ID NO:42) |
| 110G | TTGAATGAATTCACAACCTA | (SEQ ID NO:43) |
| 110H | TCAGAGTGCAGCAATGGCTT | (SEQ ID NO:44) |
| 110A | ATGGAAGGTGGTCAACCTGAA | (SEQ ID NO:45) |
| 110B | GATCCTGCTCGAGGGCACCA | (SEQ ID NO:46) |
| 110C | TGGTGCCCTCGAGCAGGATC | (SEQ ID NO:47) |
| 110D | TAGGTTGTGAATTCATTCAA | (SEQ ID NO:48) | a TATA box and 130 bp G-less region (−53 to +130) from Δ53 ML (7) were inserted in pGL3-Basic (Promega) to generate pTATA/130. Four TRE (one site sequence, AGGTCACAGCAGGTCA (SEQ ID NO:49)) (16) sites, all with the same head-to-tail orientation, were cloned into pTATA/130 to create pTRE4/130. Similarly, two TRE sites were inserted into an alkaline phosphatase minimum promoter-luciferase reporter (LBK-Basic; S. Stevens, unpublished) to generate pTRE2-LBK-luc. Four human VDR binding sites (17) were ligated into pTATA/130 to create pVDRE4/130. TRAP220 was subcloned into pGEM5Z for in vitro translation (Promega). Point mutations were introduced into TRAP220 cDNA by using the Altered Sites II in vitro Mutagenesis System (Promega). Intact and mutated TRAP220 cDNA segments were then subcloned into pCIN4 (18) to create pCIN4-TRAP220 constructs, and human TRα was subcloned into pNT7-SB (19) to generate pNT7-TRα, for expression in transfected cells. For expression of GST fusion proteins, cDNAs encoding TRAP220/1 (residues 405 to 644), TRAP220/2 (residues 622 to 701), TRAP100(1-253), human TRα, human PPARα (obtained by RT-PCR), mouse PPARγ2 (20), human VDR (21) and human ERα (302-595) were subcloned into pGEX vectors (Pharmacia). Human VDR was FLAG-tagged and further subcloned to create pVL1392-FLAG-hVDR.

Antibody Production and Western Blot

GST-TRAP220/2 and GST-TRAP100(1-253) were expressed in and purified from *E. coli* strain BL21(DE3), and 10 mg of each were gel-isolated for antibody production in rabbits (Covance, Denver, Pa). Mouse monoclonal antibodies against human TRα-1 (Santa Cruz Biotechnology) were used as specified. Western blots were visualized by enhanced chemiluminescence (ECL, Amersham).

In vitro Protein-protein Interaction and Far Western Analyses

Proteins were synthesized and labeled with $^{35}$S-methionine in a coupled transcription-translation system (TNT kit; Promega). 1.5 μg of immobilized GST-fusion protein and 2 μl of $^{35}$S-labeled input proteins were used in GST pull-down assays. For coimmunoprecipitation (7), 2 μl of anti-FLAG M2 affinity gel (Kodak) and 3 μl of $^{35}$S-labeled input proteins were used. For Far Western analyses, 500 ng of purified TR-TRAP complex was resolved by SDS-PAGE and transferred onto a nitrocellulose membrane. The blots were probed with in vitro translated, $^{35}$S-labeled human TRα-1 or TRα-1 C-terminus (residues 122–410) in the presence and absence of $10^{-7}$ M $T_3$.

Gel Filtration. 1 μg of purified TR-TRAP complex was fractionated on Superose 6 (SMART, Pharmacia) in buffer BC300 (7) containing 0.1% NP40 in the absence of $T_3$. Fractionated proteins were resolved by SDS-PAGE and visualized either by silver staining or by Western blot.

Transient Transfection

NIH 3T3 cells were maintained in DMEM with 10% calf serum. 12 hours before transfection, confluent cells were split (1:5) into 6 well plates with DMEM plus 10% dialyzed calf serum (Sigma). Calcium phosphate precipitation plus CalPhos Maximizer (Clontech) were used in transfections (19). After 36 hour incubation with DNA precipitates, the cells were harvested and luciferase activities were measured with Luciferase Assay System with Reporter Lysis Buffer (Promega). pRSV-β-gal was employed as an internal control for normalization of transfection efficiency.

Baculovirus-mediated Expression of VDR, TR and RXR and In vitro Transcription pVL1392-FLAG-VDR, -TRα and -RXRα were cotransfected into Sf9 cells with BacVector-3000 (Novagen). Expressed human VDR, TRα and RXRα were purified (to 99% homogeneity) on anti-FLAG M2 agarose. In vitro transcription assays were performed as described (7).

Results

TRAP220 and TRAP100 cDNA clones cDNAs encoding TRAP220 and TRAP100 were isolated (Materials and Methods) on the basis of amino acid sequences (underlined in FIG. 5A) derived from cognate polypeptides in the immuno-purified TR-TRAP complex. The open reading frame of TRAP220 (FIG. 5A) encodes a novel human protein containing 1581 residues, including a region (residues 635–703) nearly identical to that specified by a short cDNA (Trip 2) isolated in a yeast two hybrid screen with rat TRβ1 as bait (22). Although the cDNA-encoded protein has a calculated mass of only 168 kDa, the in vitro translated product has an electrophoretic mobility equivalent to that of TRAP220 (detected by immunoblot) in the natural TR-TRAP complex (FIG. 5B) and thus appears to be a full length protein with an aberrant mobility (possibly due to the high serine content). TRAP220 contains two of the LXXLL domains previously implicated in nuclear hormone receptor interactions (reviewed in 6) and one is found in the Trip 2 fragment (boxed residues in FIG. 5A). cDNA sequence analyses also revealed a spliced mRNA variant containing a frame shift after glycine 216 and a stop codon at position 263 (data not shown), suggesting the possibility of a truncated TRAP220 (lacking a receptor interaction domain) that might have a distinct regulatory function.

The TRAP100 cDNA encodes a 989 amino acid residue protein (FIG. 5A) with a calculated mass of 110 kDa and an electrophoretic mobility similar to that of the TRAP100 in the natural TR-TRAP complex (FIG. 5B). TRAP100 has a presumptive zinc finger in the N-terminal region (residues 83–117), a putative ATP/GTP binding site in the central region (residues 436–448) and six dispersed LXXLL motifs (boxed residues) (FIG. 5A).

Figure 5C:
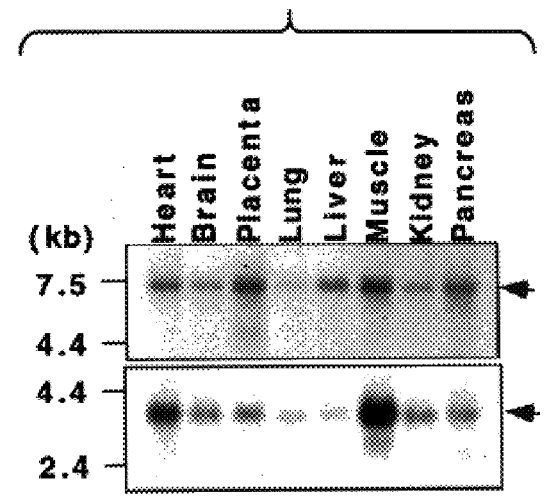

Northern blot analysis of multiple human tissues showed that TRAP220 and TRAP100 are expressed ubiquitously, although at varying levels (FIG. 5C). Both transcripts are relatively abundant in skeletal muscle, heart and placenta.

TRAPs Remain in a Multiprotein Complex in the Absence of TR

To further investigate the nature of the TR-TRAP complex, including the possibility of heterogeneity and the existence of a TRAP complex in the absence of TR and ligand, an immunopurified TR-TRAP complex isolated from ligand-treated cells (7) was subjected to gel filtration (Superose 6) in the absence of ligand. Analysis by silver stain (FIG. 6A) and by immunoblot (FIG. 6B) with antibodies to TRα and selected recombinant TRAPs (220, 150 and 100) showed a peak in the 1.5 MDa range that contained essentially all TRAPs, but no TRα, and a peak in the 660 kDa range that contained all detectable TRα and a small fraction (<5%) of TRAPs. These results, demonstrating a persistent association of TRAPs in vitro in the absence of TRα and ligand, suggests the possibility that the formation of the TR-TRAP complex in vivo may result from a ligand-induced association of TRα with a preformed (ligand independent) TRAP complex.

Interactions of TRAP220 and TRAP100 with Nuclear Hormone Receptors

Figure 7A:
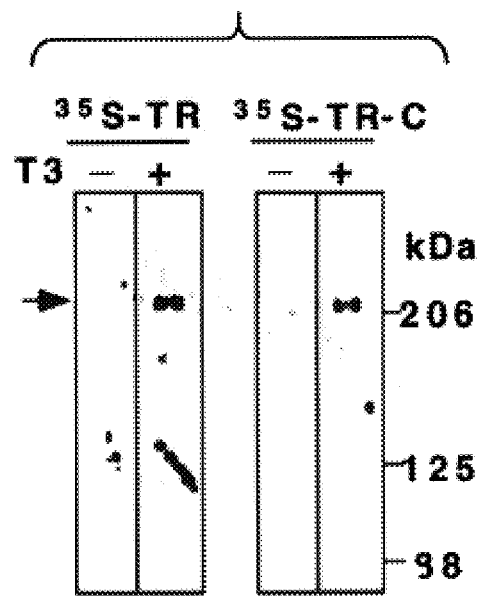
FIG. 7. Ligand-dependent interaction between TRα and TRAP220. (A) Far Western. 500 ng of purified TR-TRAP complex was separated by SDS-PAGE (8% gel), blotted and probed with $^{35}$S-labeled full length (TR) and C-terminal (TRα-C) hTRα in the presence and absence of $10^{-7}$ M 3,3',5-triiodothyroacetic acid ($T_3$). The arrow head indicates the position of the TRAP220 band. (B) Co-immunoprecipitation of TR-TRAP220 from in vitro translated products. The indicated combinations of $^{35}$S-labeled TRAP220, TRAP100 and FLAG-TRα were incubated in the presence and absence of 3,3',5-triiodothyroacetic acid ($T_3$), and subjected to immunoprecipitation with anti-FLAG antibodies (M2 agarose) that recognizes only FLAG-tagged TRα.
Figure 7B:
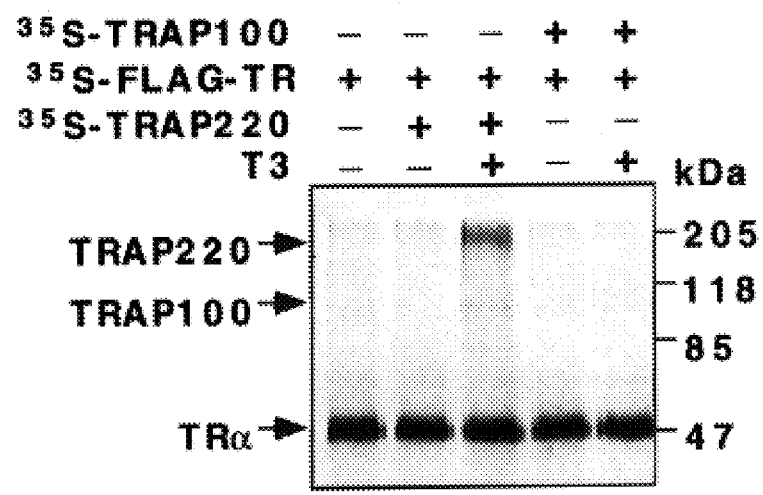
Figure 8A:
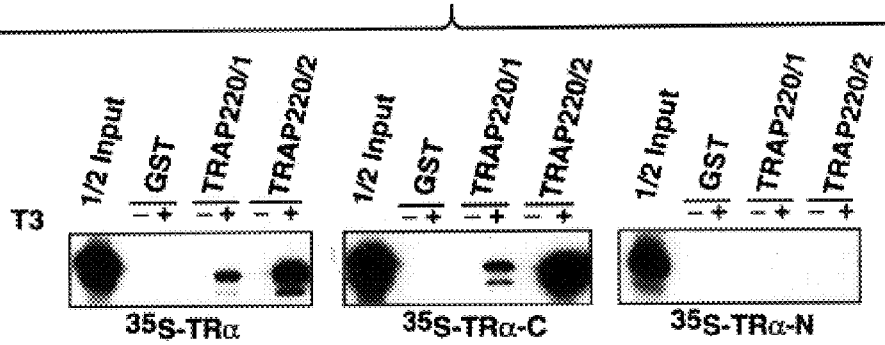
FIG. 8. Nuclear hormone receptor interactions with TRAP200 and TRAP100. (A) Ligand-dependent interactions of GST-TRAP220/1 and 2 with $^{35}$S-labeled TRα. 1.5 mg of GST or GST-TRAP220/1 and 2 fusion proteins were incubated with $^{35}$S-labeled TRα, TRα-C, or TRα-N in the presence and absence of $10^{-7}$ M 3,3',5-triiodothyroacetic acid. (B) Interactions between GST-receptors and $^{35}$S-labeled TRAP220 and TRAP100. GST and GST-nuclear hormone receptor fusion proteins (1.5=μg) were immobilized and incubated with 35S-TRAP220 or $^{35}$S-TRAP100 at either 300 mM KCl (TRα, VDR, RARα and ERα) or at 100 mM KCl (RXR, PPARα and mPPARg). The cognate ligands were $10^{-7}$ M 3,3',5-triiodothyroacetic acid (TRα), $10^{-6}$ M all-trans retinoic acid (RARα), $10^{-6}$ M 9-cis retinoic acid (RXRα), $10^{-7}$ M 1a,25(OH)2D3 (VDR), $10^{-4}$ M Wy14643 (PPARα) and $10^{-5}$ M 15-deoxy-D12,14-prostaglandin J2 (mPPARg).

To test which TRAPs interact with TRα, the entire complement of TRAPs (in the natural TR-TRAP complex) were initially probed by a Far Western analysis. Intact TRα and a C-terminal fragment (TRα-C, residues 122–410) containing the ligand-binding and AF-2 domains interacted with TRAP220, but not with the other TRAPs, in a ligand (T$_3$)-dependent manner (FIG. 7A). This interaction was confirmed by co-immunoprecipitation of in vitro translated, $^{35}$S-labeled recombinant proteins. As shown in FIG. 7B, anti-FLAG monoclonal antibodies that recognize FLAG-tagged TRα co-immunoprecipitate TRAP220, but not TRAP100, in a ligand-dependent fashion. To analyze domains in TRAP220 involved in receptor interactions, regions containing the first LXXLL motif (TRAP220/1, residues 405–644) and the second LXXLL motif (TRAP220/2, residues 622–701) were expressed as GST fusion proteins. As shown in FIG. 8A, intact TRα and TRα-C, but not an N-terminal fragment (TRα-N) containing the AF-1 and DNA-binding domains, were bound in a ligand-dependent manner to both GST-TRAP220/1 and GST-TRAP220/2, but not to GST alone. However, the binding affinity is much stronger for TRAP220/2. Thus, TRAP220/2 and the TRα C-terminus containing the ligand-binding and AF-2 domains provide the major interface for the ligand-dependent TRα-TRAP220 interaction.

Given the conservation of various motifs in the ligand-binding domains of nuclear hormone receptors, and the common interaction with other coactivators through LXXLL domains (reviewed in 6), interactions of TRAP220 and TRAP100 with other receptors were tested for with GST pull-down assays. As shown in FIG. 7A, in vitro-translated TRAP220 showed significant ligand-dependent binding not only to TRα but also to VDR, RARα and ERα under moderately stringent binding conditions (300 mM KCl). Under less stringent conditions (100 mM KCl) TRAP220 showed interactions with RXRα, PPARα, and PPARg that were enhanced significantly by cognate ligands. In contrast, and despite the presence of six LXXLL motifs, TRAP100 showed only marginal (ligand-dependent) interactions with ERα, RXRα, PPARα and PPARg.

In vivo Function of TRAP220

Figure 9A:
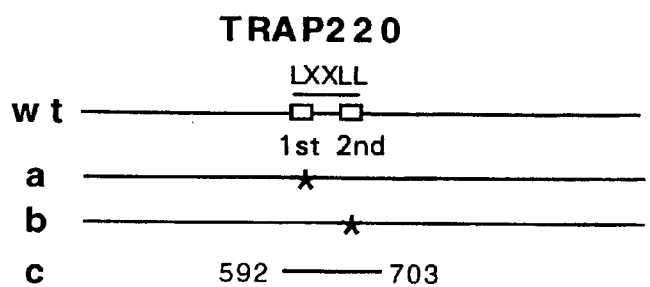
FIG. 9. In vivo function of TRAP220 in transfected NIH 3T3 cells. (A) Diagram of TRAP220 constructs. The two LXXLL motif-containing regions are represented by rectangles and corresponding mutations (LXXLL to LXXAA) by asterisks. (B) Effects of TRAP220 on TR-mediated activation of the TRE-containing reporter. Cells were transfected with 2 μg of pTRE2-LBK-luc, 2 μg of pRSV-b-gal (internal control), 0.1 μg of pNT7-TRα and either 3 μg of pCIN4-TRAP220 or an empty vector pCIN4 as indicated.

In order to test the functional role of TRAP220 in vivo, the influence of TRAP220 mutants on a T$_3$/TRα-responsive, TRE-containing luciferase reporter was tested by cotransfection of NIH3T3 and COS7 cells. Since similar results were obtained for both cell lines, only those for NIH3T3 cells are shown. To help overcome limitations due to endogenous TRAPs, the TRα and TRAP220 expression vectors (FIG. 9A) were driven by the strong CMV promoter and the dosages were optimized.

Figure 9B:
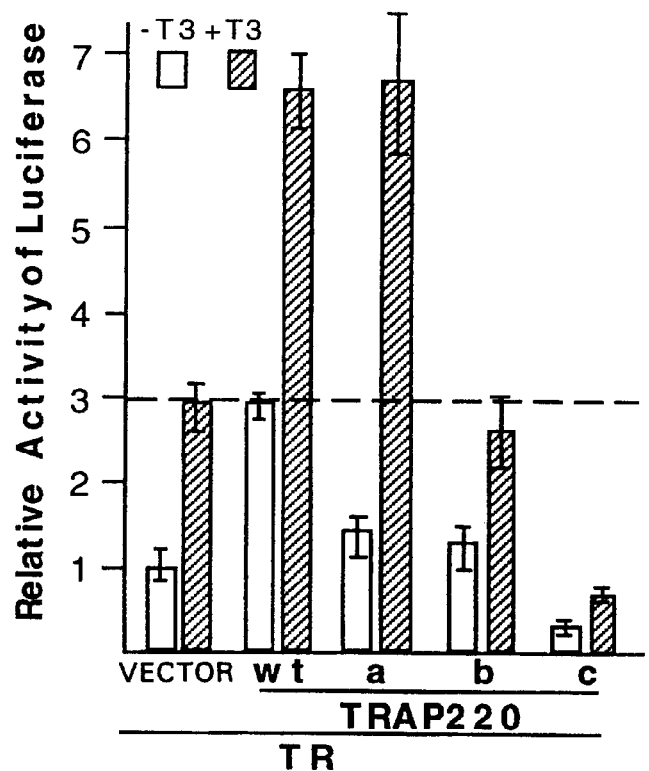

In the presence of T$_3$, intact (wt) TRAP220 moderately and reproducibly (in three experiments) enhanced TRα-mediated activation (FIG. 9B), consistent with results observed with a mouse homologue (PBP) of TRAP220 (8). The weak activation may reflect the normal function of TRAP220 within a larger TRAP complex, but also suggests that TRAP220 could be a limiting component. A mutation in the first LXXLL domain (mutant a) had no effect on the coactivator function of TRAP220 in the presence of ligand, whereas the same mutation in the second LXXLL domain (mutant b) completely abolished the observed coactivator function (FIG. 9B). This result indicates the primary importance of the second motif and is consistent with indications of a stronger receptor interaction of this motif in the direct binding assay (FIG. 7A). Given the likelihood that TRAP220 may function optimally only in conjunction with other TRAPs (7), an attempt was made to create a dominant negative mutant that would provide more compelling evidence for TRAP220 function in this context. As shown in FIG. 9B, and consistent with the results of the PBP study (8), a 112-residue TRAP220 fragment containing both LXXLL domains dramatically reduced the ligand-dependent TR-mediated activity.

TRAP220 mutants a and b showed no effects on ligand-independent activity, whereas, unexpectedly, intact TRAP220 stimulated and TRAP220 mutant c inhibited this activity (FIG. 9B). These latter effects may reflect weak ligand-independent interactions between TRAP220 and TRα that are driven by high levels of TRAP220. Similar ligand-independent interactions and corresponding effects on transcription have been reported for other receptors and over-expressed coactivators in yeast (6,8). Although under no obligation to explain such results, and not intending to be bound by any explanation set forth herein, Applicants postulate that a possible explanation for the enhanced ligand-independent basal activity is that overexpressed levels of intact TRAP220 result in the release of TR-associated co-repressors such as NCoR and SMRT (reviewed in 4,5). However, the anti-repression function of TRAP220 appears to require not only both LXXLL domains, but also the coactivator activity; the latter is indicated by the fact that TRAP220 mutant c failed to show anti-repression and, instead, further inhibited the (ligand-independent) basal activity of the TR-driven promoter. In this case the dominant negative mutant may be blocking the activity of endogenous TRAP220 (or TRAP complex) on a distinct (activated) population of the transfected reporter genes.

Figure 9C:
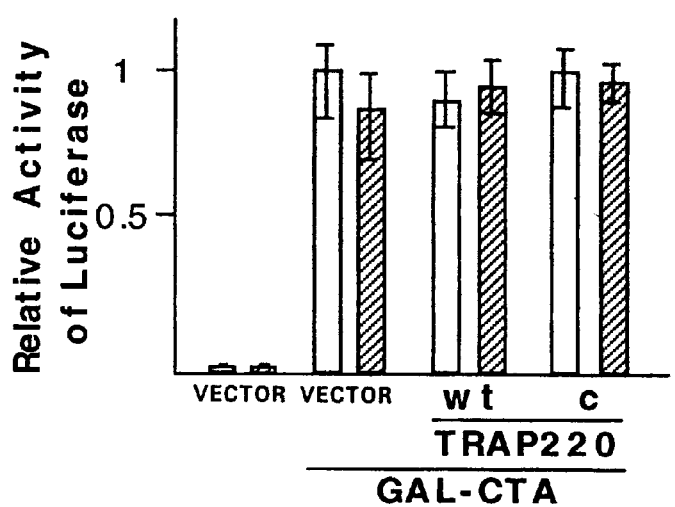

Since both intact and mutant c forms of TRAP220 had effects on transcription of the TR-responsive promoter in the absence of ligand, it was essential to eliminate the possibility of general effects of these factors on transcription. As shown in FIG. 9C, neither intact TRAP220 nor mutant c had any significant effect, in the presence or absence of $T_3$, on either the basal activity or the activator-enhanced (over 100 fold) activity of a reporter (pG5-luc) that contains 5 Gal4 sites upstream of the luciferase reporter. The activator (pGAL-CTA) in this case consisted of the Gal4 DNA binding domain fused to the C-terminal activation domain of human heat shock factor (19). These results provide further support for the significance and specificity of the coactivator activity of the dominant negative derivative (mutant c).

In vitro Function of TRAP220

Figure 10A:
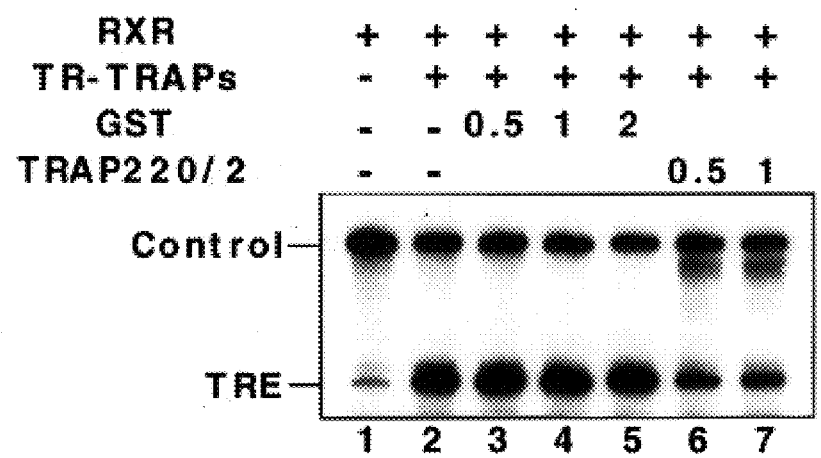

Previous study has shown that the TR-TRAP complex could significantly activate a TRE-containing promoter both in nuclear extracts and in a system reconstituted with purified factors (7). As shown in FIG. 10A, the GST-TRAP220/2 fusion protein (containing the LXXLL domain that most strongly interacts with TRα) showed a significant (5 fold) inhibition of the TR-TRAP enhanced activity on the TRE-containing promoter, with no effect on the control promoter, whereas GST alone had no effect on either promoter. These in vitro effects of TRAP220/2 parallel the effects of the dominant negative mutant c in vivo, and further support the notion that TRAP220 is (or is part of) a bona ride coactivator.

Figure 8B:
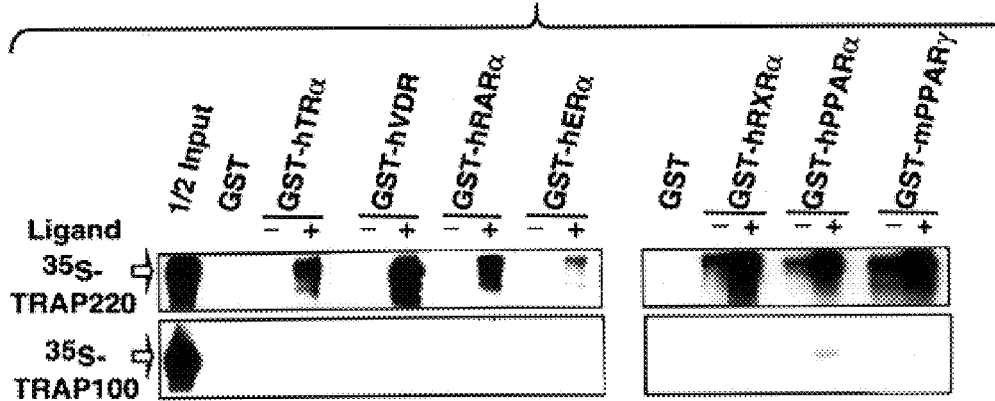
Figure 10B:
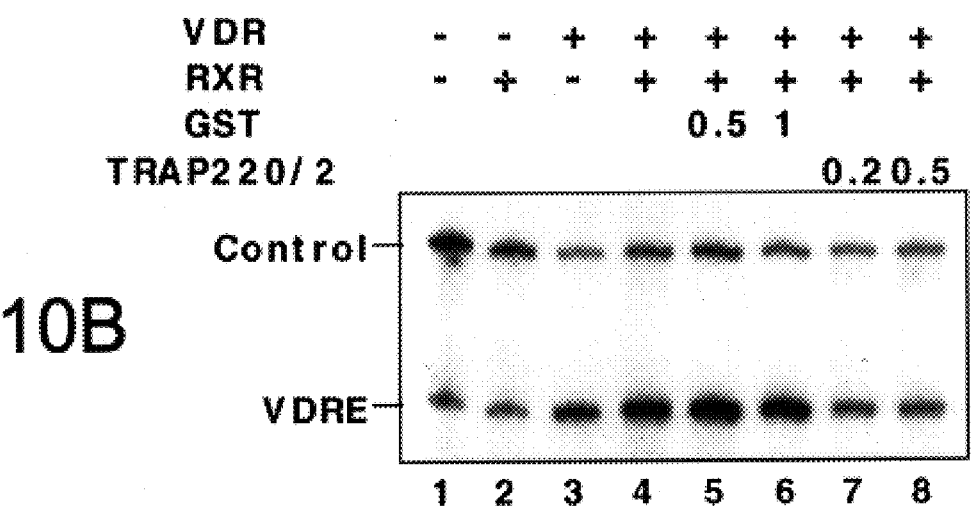

In view of the suggestion from the receptor interaction data (FIG. 8B) that TRAP220 might be involved in VDR function, and given the ability of VDR to activate VDRE-containing promoters in nuclear extracts (23), the effect of TRAP220/2 on VDR-dependent transcription was tested in vitro. As shown in FIG. 10B, a VDRE-containing promoter was modestly and selectively (relative to the control promoter) activated in response to VDR and RXR; and GST-TRAP220/2 selectively abolished the VDR-mediated activity, with no effect on the control template, while GST alone had no effect. These functional data support the idea that TRAP220 is a more general coactivator for nuclear hormone receptors.

Discussion

Transcriptional coactivators, broadly defined as factors essential for the function of DNA-binding activators, but not for transcription initiation from core promoter elements by basal factors, provide an increasingly important level of regulation and fall into several groups: (i) those whose primary interactions are with specific DNA-bound activators, such as the early-described B cell-specific OCA-B (24) and ubiquitous CBP (25), (ii) those which are intimately associated with the general transcriptional machinery, including the TAF components of TFIID (reviewed in 26) and the SRB/MED components associated with polymerase II (reviewed in 27) and (iii) potentially more general factors, such as the human USA-derived positive cofactors (28) and nucleosome remodeling factors (29). Such cofactors may function either to relieve the effects of negative constraints (chromatin structure, specific negative cofactors) or as adapters between activators and the general transcriptional machinery. In the case of nuclear hormone receptors, many of the best studied coactivators fall into the first category and interact with receptors in a ligand-dependent fashion through the C-terminal AF-2 containing domain (Introduction). The present study shows that the human TRAPs represent a novel group of cofactors, provides insights into their mechanism of action and suggests a more global role in the function or regulation of a variety of nuclear hormone receptors.

Structure and Function of TRAPs

On the basis of cognate cDNA cloning and sequence analyses TRAP220 and TRAP100 are distinct from other nuclear hormone receptor coactivators, with the exception of a recently reported mouse homologue of TRAP220 (8). Sequence analysis of most of the other TRAPs also confirms their novelty with respect to other coactivators (unpublished observations). In support of this finding, and the idea of distinct functions, most or all of the TRAPs (including TRAP220 and 100) appear to reside in a single complex. TRAPs 220 and 100 show no obvious common motifs with other coactivators, except for the LXXLL motifs implicated in receptor-coactivator interactions (reviewed in 6). In conjunction with this finding, and in support of a major role for TRAP220 in anchoring other TRAPs to the receptor, TRAP220 showed strong ligand-dependent receptor interactions that were mediated by the C-terminal ligand-binding domain and dependent upon an intact LXXLL domain. However, while no other TRAP showed comparably strong TR interactions, including TRAP100 with six LXXLL domains, the possibility of additional TRAP-receptor interactions in the context of the TR-TRAP complex is not excluded. That TRAP220 and associated TRAPs are involved in the function of the nuclear hormone receptor AF-2 domain is suggested by the loss of receptor interactions in a mutated mouse homologue (PBP) of TRAP220 (8).

In further support of a nuclear hormone receptor coactivator function for TRAP220, ectopically expressed TRAP220 moderately enhanced TRα function in transfected cells, while a truncated form of TRAP220 containing the LXXLL motifs acted as a dominant negative inhibitor of TRα function both in transfected cells and in a cell free system containing the TR-TRAP complex. The latter observation indicates that regions outside the receptor-interaction domain are also required for coactivator function. In addition, however, an apparent derepression effect of TRAP220 on ligand-independent TR function was dependent on both LXXLL-containing domains and the capability for coactivator function, suggesting that multiple TRAP220 domains may be required for dissociation of presumptive receptor-bound (co)repressors (below).

Mechanism of Action of TRAPs in Relation to Other Nuclear Hormone Receptor-Interacting Cofactors The fact that TRAPs enhance TRα function in cell free systems reconstituted with general transcription factors and naked DNA templates suggests that they are involved directly in preinitiation complex assembly or function. This could involve interactions with general initiation factors or with general coactivators such as PC4 and PC2 (28) that enhance the intrinsic activity of these factors. At the same time, a possible role for TRAPs in reversing the action of specific negative cofactors (28) that might also be present in the partially purified reconstituted system is not excluded.

The currently available information on both TRAPs and other nuclear hormone receptor-interacting cofactors suggests a general model for nuclear hormone receptor function. Major features include (i) the ligand-independent binding of nuclear hormone receptors (to target DNA sites within chromatin) along with co-repressors (SMRT/NCoA, Sin3, and histone deacetylases) that help maintain a repressed state by deacetylation of nucleosomal histones (30,31). (ii) ligand-mediated dissociation of (co)repressors plus concomitant binding of coactivators (SRC-1 related factors, p300/CBP and PCAF) that contain, or interact with factors that contain, histone acetyltransferase activity (reviewed in 4–6), with resulting acetylation of nucleosomal histones or possibly other factors (32), and (iii) binding of TRAPs (or a receptor-TRAP complex), perhaps with displacement of other coactivators (or receptor-coactivator complex), and subsequent interactions (above) with general initiation factors or coactivators. This latter step could also involve direct (ligand-independent) interactions of nuclear hormone receptors with general initiation factors (reviewed in 6).

Complexity, Specificity, and Potential Regulation of TRAPs and other Nuclear Hormone Receptor Coactivators Although the receptor binding and coactivator functions for TRAPs were originally demonstrated for TRα, the present study also shows ligand-dependent binding of TRAP220 to RARα, RXRα, VDR, PPARα, PPARg, and ERα. This suggests a much broader receptor specificity for TRAPs, and functional studies showed that a dominant negative form of TRAP220 can inhibit both TRα and VDR function. Other nuclear hormone receptor-interacting coactivators also function broadly with nuclear hormone receptors (reviewed in 4–6) and, in the case of p300/CBP, with many unrelated activators as well (reviewed in 33).

Given the target gene DNA-binding and activation specificity intrinsic to the various nuclear hormone receptors and their cognate ligands, as well as the enormous complexity of the general transcriptional machinery (containing the ultimate receptor targets), the question arises as to the reason for the unexpected complexity of the nuclear hormone receptor coactivators. This may relate to the extreme diversity of physiological processes (in growth, differentiation, and homeostasis) that involve nuclear hormone receptor function and the need for secondary regulatory events that are mediated through other signaling pathways that affect the abundance or activity of the cofactors. Cell- or cell-state specific variations in coactivators, as originally observed for the B cell-specific OCA-B (24) could help explain various cell- and promoter-specific effects of nuclear hormone receptor/ligand function. Finally, the complexity of receptor interacting coactivators, most notably the 9–10 subunit TRAP complex, may also reflect a functional redundancy with other coactivators such as those associated with the general transcriptional machinery; and recent studies in fact suggest that the TAF components of TFIID may be dispensable for TR-TRAP function in vitro (unpublished observations).

References

1. Mangelsdorf, D. J. & Evans, R. M. (1995) Cell 83, 841–850.
2. Roeder, R. G. (1996) Trends Biochem. Sci. 21, 327–335.
3. Meyer, M. E., Gronemeyer, H., Turcotte, B., Bocquel, M. T., Tasset, D. & Chambon, P. (1989) Cell 57, 433–442.
4. Glass, C. K., Rose, D. W. & Rosenfeld, M. G. (1997) Curr. Opin. Cell Biol. 9, 222–232.
5. Shibata, H., Spencer, T. E., Onate, S. A., Jenster, G., Tsai, S. Y., Tsai, M. J. & O'Malley, B. W. (1997) Recent Prog. Horm. Res. 52, 141–164.
6. Voegel, J. J., Heine, M. J. S., Tini, M., Vivat, V., Chambon, P. & Gronemeyer, H. (1998) EMBO J. 17, 507–519.
7. Fondell, J. D., Ge, H. & Roeder, R. G. (1996) Proc. Natl. Acad. Sci. USA 93, 8329–8333.
8. Zhu, Y., Qi, C., Jain, S., Rao, M. S. & Reddy, J. K. (1997) J. Biol. Chem. 272, 25500–25506.
9. Chang, K.-H., Chen, Y., Chen, T.-T., Chou, W.-H., Chen, P.-L., Ma, Y.-Y., Yang-Feng, T. L., Leng, X.-H., Tsai, M.-J., O'Malley, B. W. & Lee, W.-H. (1997) Proc. Natl. Acad. Sci. USA 94, 9040–9045.
10. Monden, T., Wondisford, F. E. & Hollenberg, A. N. (1997) J. Biol. Chem. 272, 29834–29841.
11. Ogryzko, V. V., Schiltz, R. L., Russanova, V., Howard, B. H. & Nakatani, Y. (1996) Cell 87, 953–959.
12. Yang, X. J., Ogryzko, V. V., Nishikawa, J., Howard, B. H. & Nakatani, Y. (1996) Nature 382, 319–324.
13. Spencer, T. E., Jenster, G., Burcin, M. M., Allis, C. D., Zhou, J., Mizzen, C. A., McKenna, N. J., Onate, S. A., Tsai, S. Y., Tsai, M. J. & O'Malley, B. W. (1997) Nature 389, 194–198.
14. Chen, H., Lin, R. J., Schiltz, R. L., Chakravarti, D., Nash, A., Nagy, L., Privalsky, M. L., Nakatani, Y. & Evans, R. M. (1997) Cell 90, 569–580.
15. Nagase, T., Seki, N., Tanaka, A., Ishikawa, K. & Nomura, N. (1995) DNA Res. 2, 167–174.
16. Katz, R. W. & Koenig, R. J. (1994) J. Biol. Chem. 269, 18915–18920.
17. Ozono, K., Liao, J., Kerner, S. A., Scott, R. A. & Pike, J. W. (1990) J. Biol. Chem. 265, 21881–21888.
18. Rees, S., Coote, J., Stables, J., Goodson, S., Harris, S. & Lee, M. G. (1996) BioTechniques 20, 102–110.
19. Yuan, C.-X., Verner, E. C. & Gurley, W. B. (1997) Cell Stress & Chaperones 2, 263–275.
20. Brun, R. P. & Spiegelman, B. M. (1997) J. Endocrinol. 155, 217–218.
21. Koszewski, N. J., Reinhardt, T. A. & Horst, R. L. (1996) J. Steroid Biochem. Mol. Biol. 59, 377–388.
22. Lee, J. W., Choi, H.-S., Gyuris, J., Brent, R. & Moore, D. D. (1995) Mol. Endocrinol. 9, 243–254.
23. Lemon, B. D., Fondell, J. D. & Freedman, L. P. (1997) Mol. Cell. Biol. 17, 1923–1937.
24. Luo, Y., Fujii, H., Gerster, T. & Roeder, R. G. (1992) Cell 71, 231–241.
25. Kwok, R. P., Lundblad, J. R., Chrivia, J. C., Richards, J. P., Bachinger, H. P., Brennan, R. G., Roberts, S. G., Green, M. R. & Goodman, R. H. (1994) Nature 370, 223–226.
26. Burley, S. K. & Roeder, R. G. (1996) Annu. Rev. Biochem. 65, 769–799.
27. Myers, L. C., Gustafsson, C. M., Bushnell, D. A., Liu, M., Erdjument-Bromage, H., Tempst, P. & Kornberg, R. D. (1998) Genes Dev. 12, 45–54.

28. Kaiser, K. & Meisterernst, M. (1996) Trends Biochem. Sci. 21, 342–345.
29. Wu, C. (1997) J. Biol. Chem. 272, 28171–28174.
30. Nagy, L., Kao, H.-Y., Chakravarti, D., Lin, R. J., Hassig, C. A., Ayer, D. E., Schreiber, S. L. & Evans, R. M. (1997) Cell 89, 373–380.
31. Heinzel, T., Lavinsky, R. M., Mullen, T.-M., Soderstrom, M., Laherty, C. D., Torchia, J., Yang, W.-M., Brard, G., Ngo, S. D., Davie, J. R., Seto, E., Eisenman, R. N., Rose, D. W., Glass, C. K. & Rosenfeld, M. G. (1997) Nature 387, 43–48.
32. Gu, W. & Roeder, R. G. (1997) Cell 90, 595–606.
33. Goldman, P. S., Tran, V. K. & Goodman, R. H. (1997) Recent Prog. Horm. Res. 52, 103–119.

The present invention is not to be limited in scope by the specific embodiments describe herein. Indeed, various modifications of the invention in addition to those described herein will become apparent to those skilled in the art from the foregoing description and the accompanying figures. Such modifications are intended to fall within the scope of the appended claims.

It is further to be understood that all base sizes or amino acid sizes, and all molecular weight or molecular mass values, given for nucleic acids or polypeptides are approximate, and are provided for description.

Various publications are cited herein, the disclosures of which are incorporated by reference in their entireties.

What is claimed is:

1. An isolated nucleic acid molecule consisting of a DNA sequence of SEQ ID NO:1, degenerate variants thereof, or fragments thereof, said fragments at least 10 nucleotides in size.

2. The isolated nucleic acid molecule of claim 1, which encodes a Thyroid Receptor-associated protein (TRAP) 220, comprising an amino acid sequence of SEQ ID NO:2, conserved variants thereof, fragments thereof.

3. An isolated molecule of claim 1, wherein said fragments are at least 20 nucleotides in length.

4. An isolated nucleic acid molecule hybridizable in 50% formamide, 6×SSC at 55° C. to an isolated nucleic acid molecule consisting of a DNA sequence of SEQ ID NO:1, degenerate variants of said isolated nucleic acid molecule, or fragments of said isolated nucleic acid molecule, said fragments at least 10 nucleotides in size.

5. An isolated molecule of claim 4, wherein said fragments are at least 20 nucleotides in length.

6. The isolated nucleic acid molecule of claim 4, detectably labeled.

7. An isolated molecule of claim 3, wherein said fragments are at least 30 nucleotides in length.

8. The isolated nucleic acid molecule of claim 4, which encodes a Thyroid Receptor-associated protein (TRAP) 220, comprising an amino acid sequence of SEQ ID NO:2, conserved variants thereof, fragments thereof.

9. An isolated nucleic acid molecule consisting of a DNA sequence of SEQ ID NO:3, degenerate variants thereof, or fragments thereof, said fragments at least 10 nucleotides in size.

10. An isolated molecule of claim 5, wherein said fragments are at least 30 nucleotides in length.

11. The isolated nucleic acid molecule of claim 10, said molecule further comprising a detectable label.

12. An isolated nucleic acid molecule hybridizable in 50% formamide, 6×SSC at 55° C. to an isolated nucleic acid molecule consisting of a DNA sequence of SEQ ID NO:3, degenerate variants of said isolated nucleic acid molecule, or fragments of said isolated nucleic acid molecule, said fragments at least 10 nucleotides in size.

13. The isolated nucleic acid molecule of claim 12, detectably labeled.

14. The isolated nucleic acid molecule of claim 13, wherein said detectable label comprises a radioactive element, a chemical which fluoresces, or an enzyme.

15. The isolated nucleic acid molecule of claim 9, which encodes a Thyroid Receptor-associated protein (TRAP) 100 nuclear hormone receptor coactivator comprising an amino acid sequence of SEQ ID NO:4, conserved variants thereof, fragments thereof.

16. The isolated nucleic acid molecule of claim 12, which encodes a Thyroid Receptor-associated protein (TRAP) 100 nuclear hormone receptor coactivator comprising an amino acid sequence of SEQ ID NO:4, conserved variants thereof, fragments thereof.

17. A cloning vector comprising the isolated molecule comprising a DNA sequence of SEQ ID NO:1, degenerate variants thereof, or fragments thereof, said fragments at least 30 nucleotides in size and further comprising an origin of replication.

18. A cloning vector comprising the isolated nucleic acid molecule hybridizable in 50% formamide, 6×SSC at 55° C. to an isolated nucleic acid molecule comprising a DNA sequence of SEQ ID NO:1, degenerate variants of said isolated nucleic acid molecule, or fragments of said isolated nucleic acid molecule, said fragments at least 30 nucleotides in size and further comprising an origin of replication.

19. A cloning vector comprising the isolated molecule comprising a DNA sequence of SEQ ID NO:3, degenerate variants thereof, or fragments thereof, said fragments at least 30 nucleotides in size and further comprising an origin of replication.

20. A cloning vector comprising the isolated nucleic acid molecule hybridizable under in 50% formamide, 6×SSC at 55° C. to an isolated nucleic acid molecule comprising a DNA sequence of SEQ ID NO:3, degenerate variants of said isolated nucleic acid molecule, or fragments of said isolated nucleic acid molecule, said fragments at least 30 nucleotides in size and further comprising an origin of replication.

21. The cloning vector of any of claims 17–20, wherein said cloning vector is selected from the group consisting of E. coli, bacteriophages, plasmids, and pUC plasmid derivatives.

22. The cloning vector of claim 21, wherein bacteriophages further comprise lambda derivatives, plasmids further comprise pBR322 derivatives, and pUC plasmid derivatives further comprise pGEX vectors, or pmal-c, pFLAG.

23. An expression vector comprising an isolated nucleic acid molecule comprising a DNA sequence of SEQ ID NO:1, degenerate variants thereof, or fragments thereof, said fragments at least 30 nucleotides in size, operatively associated with a promoter.

24. An expression vector comprising an isolated nucleic acid molecule hybridizable in 50% formamide, 6×SSC at 55° C. to an isolated nucleic acid comprising a DNA sequence of SEQ ID NO:1, degenerate variants thereof, or fragments thereof, said fragments at least 30 nucleotides in size, operatively associated with a promoter.

25. An expression vector comprising an isolated nucleic acid molecule comprising a DNA sequence of SEQ ID NO:1, degenerate variants thereof, or fragments thereof, said fragments at least 30 nucleotides in size, operatively associated with a promoter.

26. An expression vector comprising an isolated nucleic acid molecule hybridizable in 50% formamide, 6×SSC at 55° C. to an isolated nucleic acid comprising a DNA sequence of SEQ ID NO:1, degenerate variants thereof, or fragments thereof, said fragments at least 30 nucleotides in size, operatively associated with a promoter.

27. The expression vector of any of claims 23–26, wherein said wherein said promoter is selected from the group consisting of the immediate early promoters of hCMV, early promoters of SV40, early promoters of adenovirus, early promoters of vaccinia, early promoters of polyoma, late promoters of SV40, late promoters of adenovirus, late promoters of vaccinia, late promoters of polyoma, the lac the trp system, the TAC system, the TRC system, the major operator and promoter regions of phage lambda, control regions of fd coat protein, 3-phosphoglycerate kinase promoter, acid phosphatase promoter, and promoters of yeast α mating factor.

28. A unicellular host transformed or transfected with an expression vector of claim 23.

29. A unicellular host transformed or transfected with an expression vector of claim 24.

30. A unicellular host transformed or transfected with an expression vector of claim 25.

31. A unicellular host transformed or transfected with an expression vector of claim 26.

32. The unicellular host of any of claims 28–31, wherein said host comprises E. coli, Pseudonomas, Bacillus, Strepomyces, yeast, CHO, R1.1, B-W, L-M, COS1, COS7, BSC1, BSC40, BMT10, Sf9, or NIH3T3 cells.

33. The isolated nucleic acid molecule of claim 7, said molecule further comprising a detectable label.

34. The isolated nucleic acid molecule of claim 33, wherein said detectable label comprises a radioactive element, a chemical which fluoresces, or an enzyme.

35. An isolated molecule of claim 7, wherein said fragments are at least 100 nucleotides in length.

36. An isolated molecule of claim 35, wherein said molecule comprises a DNA sequence of SEQ ID NO:1 and not a fragment thereof.

37. The isolated nucleic acid molecule of claim 6, wherein said detectable label comprises a radioactive element, a chemical which fluoresces, or an enzyme.

38. The isolated nucleic acid molecule of claim 11, wherein said detectable label comprises a radioactive element, a chemical which fluoresces, or an enzyme.

39. An isolated molecule of claim 10, wherein said fragments are at least 100 nucleotides in length.

40. An isolated molecule of claim 39, wherein said molecule comprises a DNA sequence of SEQ ID NO:1 and not a fragment thereof.

41. An isolated molecule of claim 9, wherein said fragments are at least 20 nucleotides in length.

42. An isolated molecule of claim 41 wherein said fragments are at least 30 nucleotides in length.

43. An isolated molecule of claim 42, wherein said fragments are at least 100 nucleotides in length.

44. An isolated molecule of claim 43, wherein said molecule comprises a DNA sequence of SEQ ID NO:3 and not a fragment thereof.

45. An isolated molecule of claim 12, wherein said fragments are at least 20 nucleotides in length.

46. An isolated molecule of claim 45, wherein said fragments are at least 30 nucleotides in length.

47. An isolated molecule of claim 46, wherein said fragments are at least 100 nucleotides in length.

48. An isolated molecule of claim 47, wherein said molecule comprises a DNA sequence of SEQ ID NO:3 and not a fragment thereof.

49. A cloning vector of claim 17 wherein said fragments are at least 100 nucleotides in size.

50. A cloning vector of claim 18 wherein said fragments are at least 100 nucleotides in size.

51. A cloning vector of claim 19 wherein said fragments are at least 100 nucleotides in size.

52. A cloning vector of claim 20 wherein said fragments are at least 100 nucleotides in size.

53. An expression vector of claim 23 wherein said fragments are at least 100 nucleotides in size.

54. An expression vector of claim 24 wherein said fragments are at least 100 nucleotides in size.

55. An expression vector of claim 25 wherein said fragments are at least 100 nucleotides in size.

56. An expression vector of claim 26 wherein said fragments are at least 100 nucleotides in size.

* * * * *